US012617845B2

(12) United States Patent
Yadav et al.

(10) Patent No.: US 12,617,845 B2
(45) Date of Patent: May 5, 2026

(54) SMC1A ANTIBODIES AND USES THEREOF

(71) Applicant: CITY OF HOPE, Duarte, CA (US)

(72) Inventors: Sushma Yadav, Duarte, CA (US); Arthur Riggs, Duarte, CA (US); David Horne, Duarte, CA (US); John C. Williams, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 782 days.

(21) Appl. No.: 17/998,795

(22) PCT Filed: May 14, 2021

(86) PCT No.: PCT/US2021/032633
§ 371 (c)(1),
(2) Date: Nov. 14, 2022

(87) PCT Pub. No.: WO2021/231982
PCT Pub. Date: Nov. 18, 2021

(65) Prior Publication Data
US 2023/0340089 A1      Oct. 26, 2023

Related U.S. Application Data

(60) Provisional application No. 63/024,991, filed on May 14, 2020.

(51) Int. Cl.
*C07K 16/18* (2006.01)
*G01N 33/575* (2026.01)
(52) U.S. Cl.
CPC ........... *C07K 16/18* (2013.01); *G01N 33/575* (2026.01); *C07K 2317/31* (2013.01); *C07K 2317/565* (2013.01)
(58) Field of Classification Search
USPC ...................................................... 424/136.1
See application file for complete search history.

(56) References Cited

U.S. PATENT DOCUMENTS

| | | |
|---|---|---|
| 2011/0250203 A1 | 10/2011 | Klitgaard et al. |
| 2012/0177664 A1 | 7/2012 | Yokoseki et al. |
| 2015/0030600 A1 | 1/2015 | Marks et al. |
| 2015/0284452 A1 | 10/2015 | Bremel et al. |
| 2016/0251418 A1 | 9/2016 | Liu et al. |
| 2017/0073428 A1 | 3/2017 | Pittman et al. |
| 2018/0086836 A1 | 3/2018 | Lissilaa et al. |
| 2018/0200354 A1* | 7/2018 | Wu ......................... A61P 35/04 |

FOREIGN PATENT DOCUMENTS

| WO | WO-2013/055404 A1 | 4/2013 |
|---|---|---|
| WO | WO-2019/028190 A1 | 2/2019 |

OTHER PUBLICATIONS

International Search Report mailed on Sep. 22, 2021, for PCT Application No. PCT/US2021/032633, filed May 14, 2021, 3 pages.
Written Opinion mailed on Sep. 22, 2021, for PCT Application No. PCT/US2021/032633, filed May 14, 2021, 6 pages.

* cited by examiner

*Primary Examiner* — Sean E Aeder
(74) *Attorney, Agent, or Firm* — Mintz Levin Cohn Ferris Glovsky and Popeo PC

(57) ABSTRACT

Provided herein are, inter alia, antibodies capable of binding Structural Maintenance of Chromosome-1 (SMC1). The antibodies provided herein include novel light chain and heavy chain sequences and bind SMC1 (e.g., SMC1A or SMC1B) with high efficiency and specificity. The SMC1 antibodies provided herein including embodiments thereof may be used for diagnostic and therapeutic purposes, for example, as humanized SMC1 antibodies, antibody drug conjugates or they may form part of bispecific antibodies or chimeric antigen receptors.

10 Claims, 53 Drawing Sheets

Specification includes a Sequence Listing.

SDS-PAGE of Chimeric-antibodies

SDS-PAGE of ALPHA4

SMC1-BETA 92.5%

SMC1A1

5.7%

SMC1A4

78.7%

IgG only 0.3%

SMC1A(IGHV5)

90.8%

SMC1A(IGHV1-15)

78.3%

Cell line: Prostate (PC3)

IgG only

SMC1A1

SMC1A4

Cell Line:HCT116

IgG only

SMC1A1

ALPHA4

Cell Line:U251

MCF7 Breast Cancer)

U87 (Glioblastoma)

U251                                   T98G

MCF7                        PancN

FIG. 26

SMC1A ANTIBODIES AND USES THEREOF

CROSS-REFERENCES TO RELATED APPLICATIONS

This application is a national stage filing under USC 371 of International Application No. PCT/US2021/032633, filed May 14, 2021, which claims priority to U.S. Application No. 63/024,991 filed May 14, 2020, the disclosure of which are incorporated by reference herein in their entirety.

REFERENCE TO A "SEQUENCE LISTING," A TABLE, OR A COMPUTER PROGRAM LISTING APPENDIX SUBMITTED AS AN ASCII FILE

The Sequence Listing written in file 048440-766001WO_Sequence Listing_ST25.TXT, created on May 13, 2021, 29,483 bytes, machine format IBM-PC, MS Windows operating system, is incorporated herein by reference.

BACKGROUND OF THE INVENTION

Although tremendous progress has been made in the field of cancer immunotherapy for both hematological and solid tumors, lack of cancer-specific cell surface markers in aggressive cancers has resulted in a death of targeted therapies and poor patient outcomes. The compositions and methods provided herein address these and other needs in the art.dea

BRIEF SUMMARY OF THE INVENTION

In a first aspect is provided a Structural Maintenance of Chromosome-1 (SMC1) antibody including a light chain variable domain and a heavy chain variable domain, wherein the light chain variable domain includes: a CDR L1 as set forth in SEQ ID NO:1, a CDR L2 as set forth in SEQ ID NO:2 and a CDR L3 as set forth in SEQ ID NO:3; and wherein the heavy chain variable domain includes: a CDR H1 as set forth in SEQ ID NO:4, a CDR H2 as set forth in SEQ ID NO:5, and a CDR H3 as set forth in SEQ ID NO:6.

In another aspect is provided a Structural Maintenance of Chromosome-1 (SMC1) antibody including a light chain variable domain and a heavy chain variable domain, wherein the light chain variable domain includes: a CDR L1 as set forth in SEQ ID NO:7, a CDR L2 as set forth in SEQ ID NO:8 and a CDR L3 as set forth in SEQ ID NO:9; and wherein the heavy chain variable domain includes: a CDR H1 as set forth in SEQ ID NO:10, a CDR H2 as set forth in SEQ ID NO:11, and a CDR H3 as set forth in SEQ ID NO:12.

In another aspect is provided a Structural Maintenance of Chromosome-1 (SMC1) antibody including a light chain variable domain and a heavy chain variable domain, wherein the light chain variable domain includes: a CDR L1 as set forth in SEQ ID NO:13, a CDR L2 as set forth in SEQ ID NO:14 and a CDR L3 as set forth in SEQ ID NO: 15; and wherein the heavy chain variable domain includes: a CDR H1 as set forth in SEQ ID NO:16, a CDR H2 as set forth in SEQ ID NO:17, and a CDR H3 as set forth in SEQ ID NO:18.

In another aspect is provided a Structural Maintenance of Chromosome-1 (SMC1) antibody including a light chain variable domain and a heavy chain variable domain, wherein the light chain variable domain includes: a CDR L1 as set forth in SEQ ID NO:19, a CDR L2 as set forth in SEQ ID NO:20 and a CDR L3 as set forth in SEQ ID NO:21; and wherein the heavy chain variable domain includes: a CDR H1 as set forth in SEQ ID NO:22, a CDR H2 as set forth in SEQ ID NO:23, and a CDR H3 as set forth in SEQ ID NO:24; or a CDR H1 as set forth in SEQ ID NO:25, a CDR H2 as set forth in SEQ ID NO:26, and a CDR H3 as set forth in SEQ ID NO:27.

In another aspect is provided a Structural Maintenance of Chromosome-1 (SMC1) antibody including a light chain variable domain and a heavy chain variable domain, wherein the light chain variable domain includes: a CDR L1 as set forth in SEQ ID NO:39, a CDR L2 as set forth in SEQ ID NO:40 and a CDR L3 as set forth in SEQ ID NO:41; and wherein the heavy chain variable domain includes: a CDR H1 as set forth in SEQ ID NO:42, a CDR H2 as set forth in SEQ ID NO:43, and a CDR H3 as set forth in SEQ ID NO:44.

In another aspect is provided a recombinant protein including: (i) a first antibody region capable of binding an effector cell ligand; and (ii) a second antibody region, including: (a) a second light chain variable domain including a CDR L1 as set forth in SEQ ID NO: 1, a CDR L2 as set forth in SEQ ID NO:2 and a CDR L3 as set forth in SEQ ID NO: 3; a CDR L1 as set forth in SEQ ID NO:7, a CDR L2 as set forth in SEQ ID NO:8 and a CDR L3 as set forth in SEQ ID NO: 9; a CDR L1 as set forth in SEQ ID NO:13, a CDR L2 as set forth in SEQ ID NO:14 and a CDR L3 as set forth in SEQ ID NO:15; or a CDR L1 as set forth in SEQ ID NO:19, a CDR L2 as set forth in SEQ ID NO:20 and a CDR L3 as set forth in SEQ ID NO:21; and (b) a second heavy chain variable domain including a CDR H1 as set forth in SEQ ID NO:4, a CDR H2 as set forth in SEQ ID NO:5, and a CDR H3 as set forth in SEQ ID NO:6; a CDR H1 as set forth in SEQ ID NO:10, a CDR H2 as set forth in SEQ ID NO:11, and a CDR H3 as set forth in SEQ ID NO:12; a CDR H1 as set forth in SEQ ID NO:16, a CDR H2 as set forth in SEQ ID NO:17, and a CDR H3 as set forth in SEQ ID NO: 18; a CDR H1 as set forth in SEQ ID NO:22, a CDR H2 as set forth in SEQ ID NO:23, and a CDR H3 as set forth in SEQ ID NO:24; or a CDR H1 as set forth in SEQ ID NO:25, a CDR H2 as set forth in SEQ ID NO:26, and a CDR H3 as set forth in SEQ ID NO:27.

In another aspect is provided a recombinant protein including: (i) a first antibody region capable of binding an effector cell ligand; and (ii) a second antibody region, including: (a) a second light chain variable domain including a CDR L1 as set forth in SEQ ID NO:1, a CDR L2 as set forth in SEQ ID NO:2 and a CDR L3 as set forth in SEQ ID NO: 3; and (b) a second heavy chain variable domain including a CDR H1 as set forth in SEQ ID NO:4, a CDR H2 as set forth in SEQ ID NO:5, and a CDR H3 as set forth in SEQ ID NO: 6.

In another aspect is provided a recombinant protein including: (i) a first antibody region capable of binding an effector cell ligand; and (ii) a second antibody region, including: (a) a second light chain variable domain including a CDR L1 as set forth in SEQ ID NO:7, a CDR L2 as set forth in SEQ ID NO:8 and a CDR L3 as set forth in SEQ ID NO: 9; and (b) a second heavy chain variable domain including a CDR H1 as set forth in SEQ ID NO: 10, a CDR H2 as set forth in SEQ ID NO:11, and a CDR H3 as set forth in SEQ ID NO: 12.

In another aspect is provided a recombinant protein including: (i) a first antibody region capable of binding an effector cell ligand; and (ii) a second antibody region, including: (a) a second light chain variable domain including a CDR L1 as set forth in SEQ ID NO:13, a CDR L2 as set forth in SEQ ID NO:14 and a CDR L3 as set forth in SEQ ID NO:15; and (b) a second heavy chain variable domain including a CDR H1 as set forth in SEQ ID NO: 16, a CDR H2 as set forth in SEQ ID NO:17, and a CDR H3 as set forth in SEQ ID NO: 18.

In another aspect is provided a recombinant protein including: (i) a first antibody region capable of binding an effector cell ligand; and (ii) a second antibody region, including: (a) a second light chain variable domain including a CDR L1 as set forth in SEQ ID NO: 19, a CDR L2 as set forth in SEQ ID NO:20 and a CDR L3 as set forth in SEQ ID NO:21; and (b) a second heavy chain variable domain including a CDR H1 as set forth in SEQ ID NO:22, a CDR H2 as set forth in SEQ ID NO:23, and a CDR H3 as set forth in SEQ ID NO:24.

In another aspect is provided a recombinant protein including: (i) a first antibody region capable of binding an effector cell ligand; and (ii) a second antibody region, including: a CDR H1 as set forth in SEQ ID NO:25, a CDR H2 as set forth in SEQ ID NO:26, and a CDR H3 as set forth in SEQ ID NO:27.

In another aspect is provided a pharmaceutical composition including (i) a therapeutically effective amount of a SMC1 antibody as provided herein including embodiments thereof, or a therapeutically effective amount of a recombinant protein as provided herein including embodiments thereof and (ii) a pharmaceutically acceptable excipient.

In another aspect is provided a pharmaceutical composition including a therapeutically effective amount of a SMC1 antibody as provided herein including embodiments thereof.

In another aspect is provided a pharmaceutical composition including a therapeutically effective amount of a recombinant protein as provided herein including embodiments thereof and a pharmaceutically acceptable excipient.

In another aspect is provided a method of treating cancer in a subject in need thereof, the method including administering to a subject a therapeutically effective amount of a SMC1 antibody as provided herein including embodiments thereof or a therapeutically effective amount of a recombinant protein as provided herein including embodiments thereof, thereby treating cancer in the subject.

In another aspect is provided a method of treating cancer in a subject in need thereof, the method including administering to a subject a therapeutically effective amount of a SMC1 antibody as provided herein including embodiments thereof.

In another aspect is provided a method of treating cancer in a subject in need thereof, the method including administering to a subject a therapeutically effective amount of a recombinant protein as provided herein including embodiments thereof, thereby treating cancer in the subject.

In another aspect is provided an isolated nucleic acid encoding a SMC1 antibody as provided herein including embodiments thereof.

In another aspect a cell including a SMC1 antibody as provided herein including embodiments thereof.

In another aspect is provided a method of detecting a cancer cell the method including contacting a cancer cell with a SMC1 antibody as provided herein including embodiments thereof, thereby forming an antibody-cell conjugate and detecting the antibody-cell conjugate.

BRIEF DESCRIPTION OF THE DRAWINGS

FIG. 1A is an SDS-PAGE of chimeric antibodies in Non-reducing or Native (N) or Reducing (R) conditions. FIG. 1B is an SDS-page of ALPHA4. Integrity of the chimeric antibodies was checked via Coomassie Blue staining.

Figure 1A:
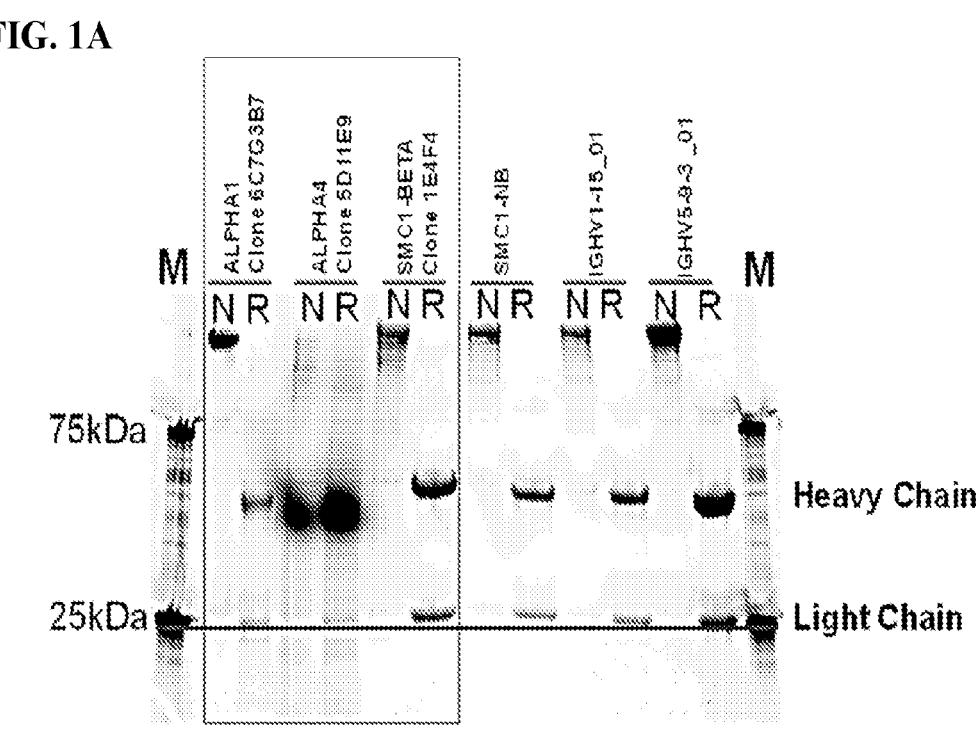
FIGS. 1A-1B present two SDS-PAGE experiments showing the development of SMC1-chimeric antibodies.
Figure 1B:
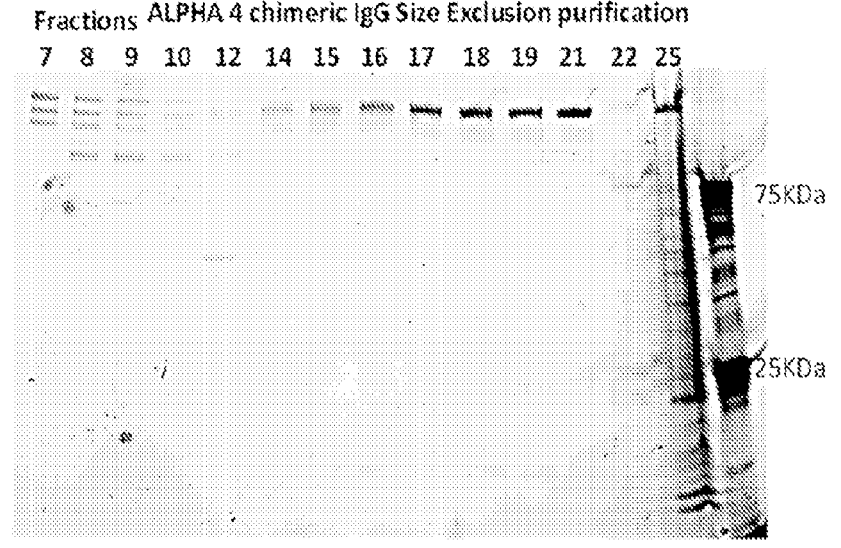
Figure 2:
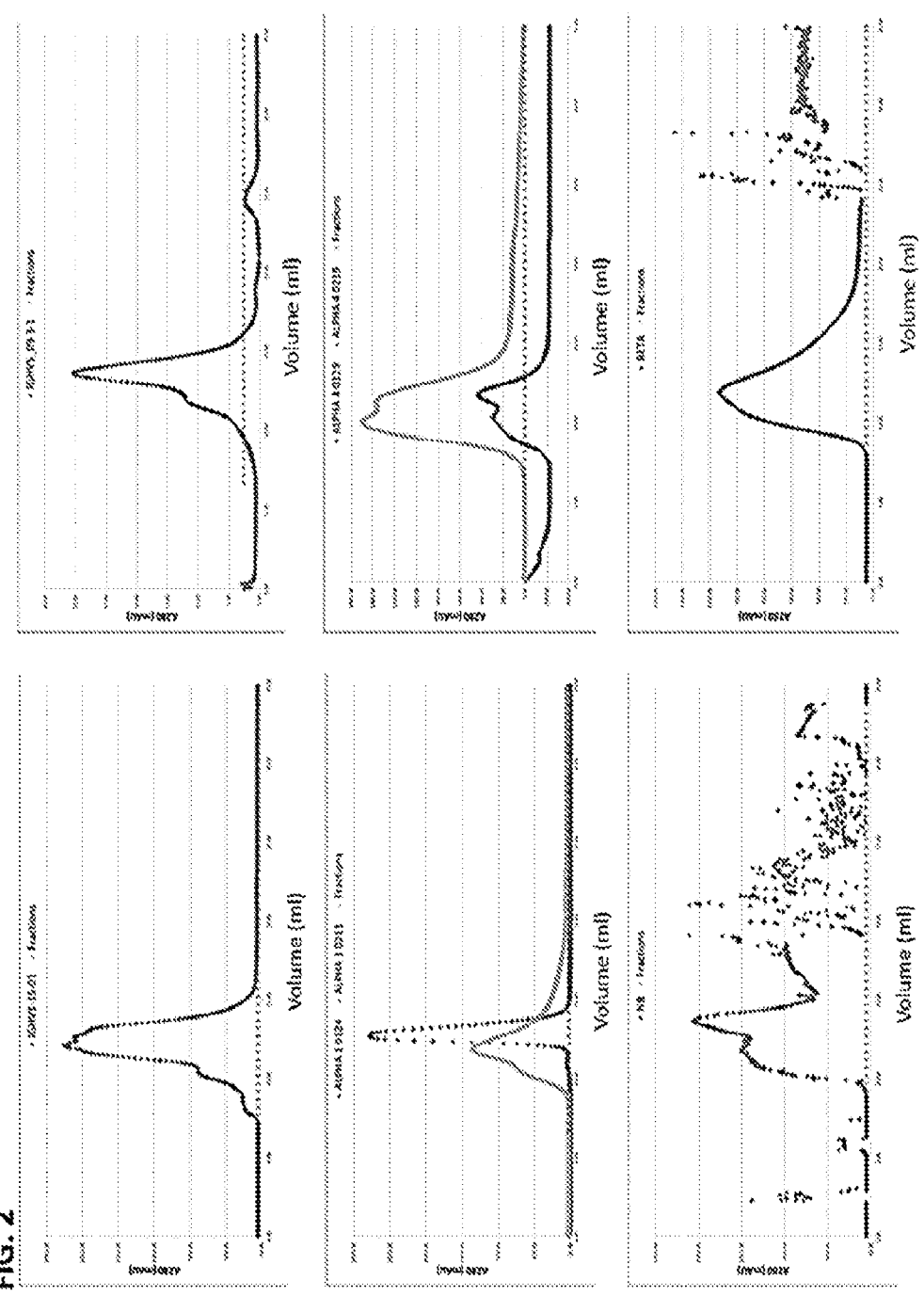

FIG. 2 presents FPLC traces for size exclusion chromatography for different chimeric IgGs.

Figure 3A:
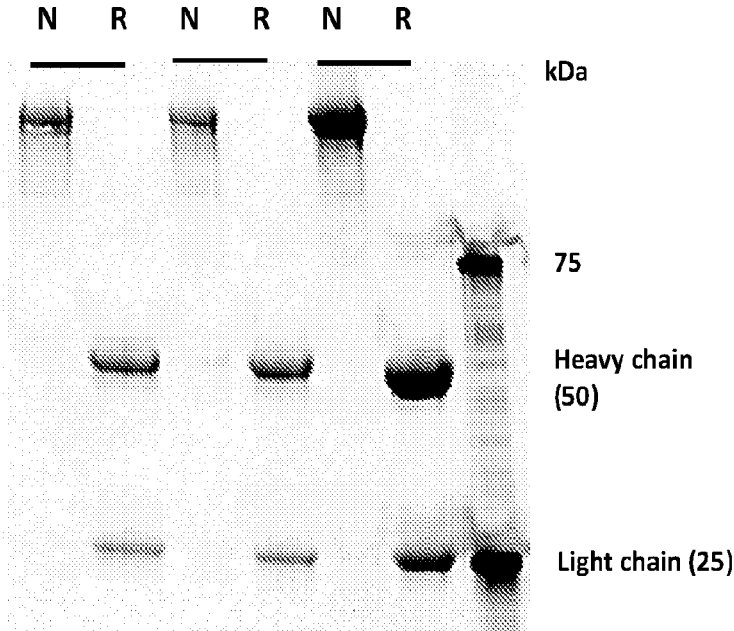
Figure 3B:
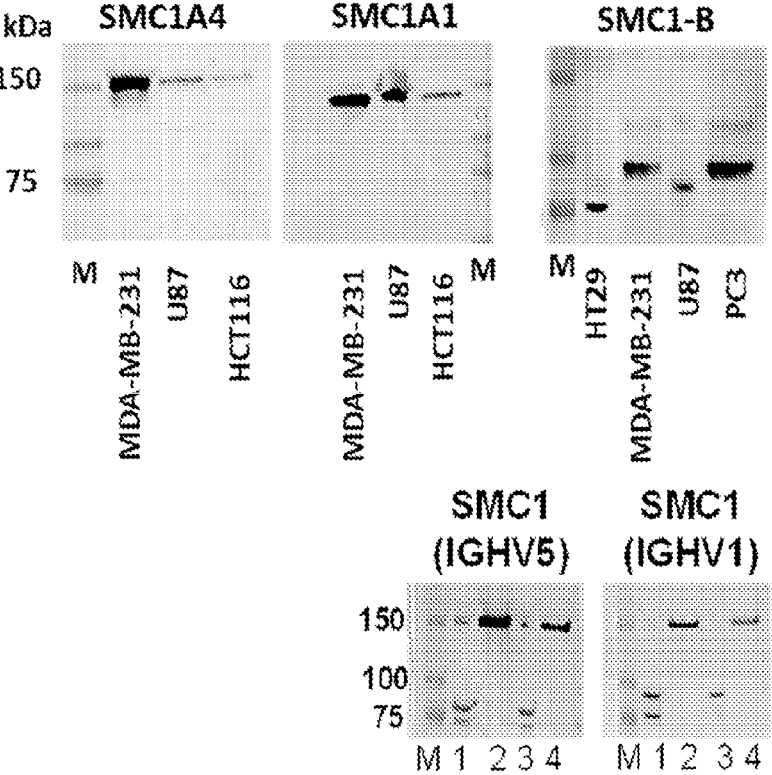

FIGS. 3A-3B show that SMC1-chimeric antibody detected SMC1A antigen in cancer cells. FIG. 3A is an SDS-PAGE of chimeric antibodies, in which chimeric antibodies (~5 µg) were run on SDS-PAGE in native (N) and reducing conditions (R), stained with Coomassie Blue to check the integrity of the antibodies. FIG. 3B shows specificity assessment of chimeric antibodies by Western blot, in which cell lysates (~10 µg protein) were resolved over Criterion™ TGX precast gels and then transferred onto polyvinylidenedifluoride (PDVF) membrane. The blots were blocked using 5% nonfat dry milk in Tris-buffered saline containing 0.1% Tween 20 (TBST) for 2 hr at RT and probed using SMC1-chimeric antibodies in 5% bovine serum albumin (BSA) in TBST buffer for overnight at 4° C. The membranes were then incubated with horseradish peroxidase (HRP) conjugated anti-human secondary antibody followed by detection using chemiluminescence ECL kit (Bio-Rad) and scanned by Image Quant LAS 500 chemiluminescence system (GE). Antibody: SMC1-chimeric (1 µg/ml); overnight, 4° C.; Sec antibody: Anti-human-HRP (1:3000; hr, RT)

Figure 4A:
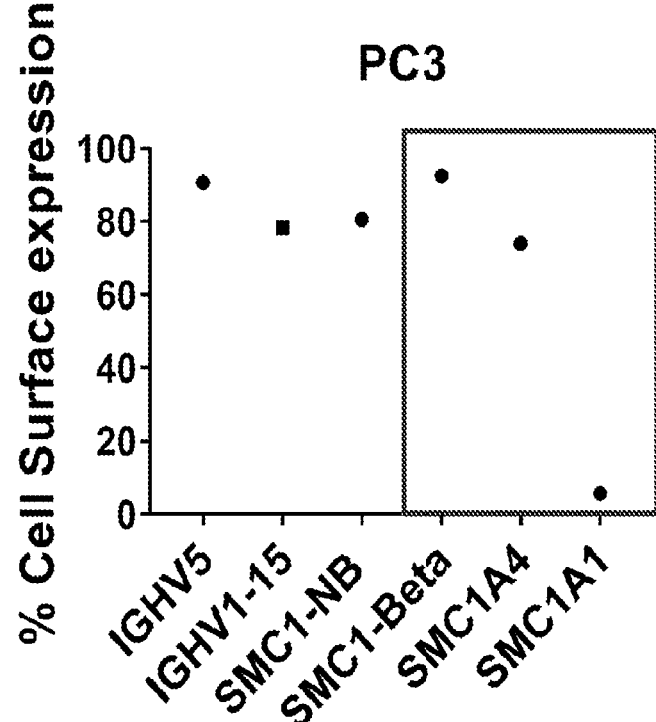
Figure 4B:
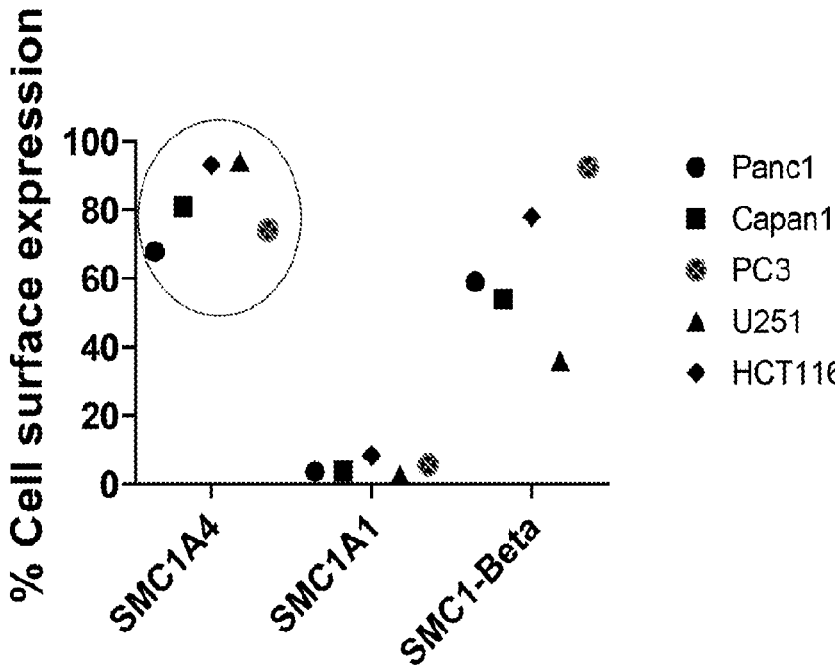
Figure 4C:
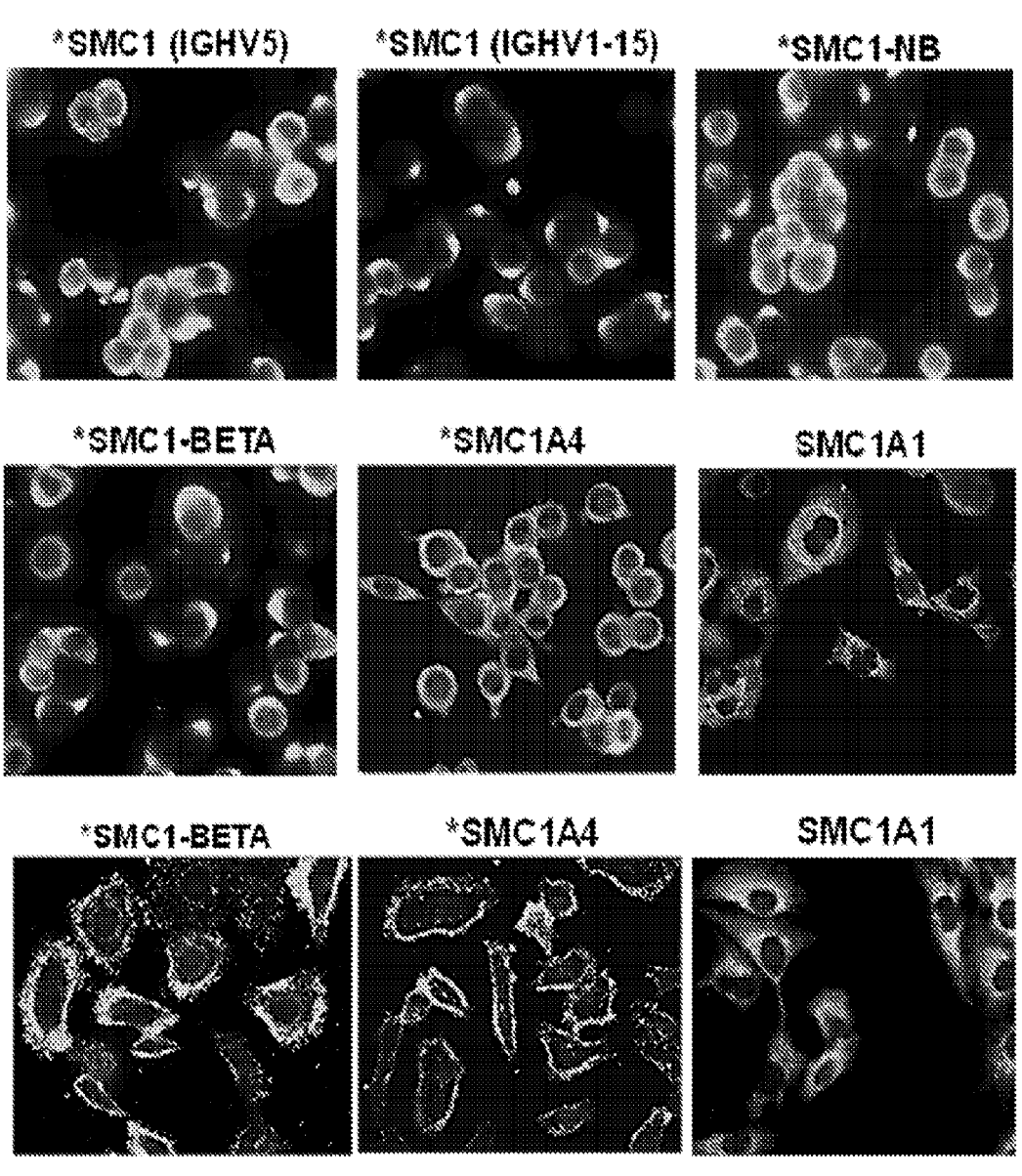

FIGS. 4A-4C show that SMC1 chimeric antibodies detected surface SMC1A antigen in cancer cells. FIG. 4A show plots presenting the percentage of cell surface expression of different antigens as measured by different chimeric antibodies on PC3 cells. FIG. 4B shows cancer cells as detected with flow cytometry (BD LSRFortessa™). FIGS. 4A-4B show cancer cells (pancreatic, prostate, glioblastoma and breast) were cultured and live cells were incubated with humanized SMC1A-antibody and surface expression of SMC1 was quantified by flow cytometer. In each of these experiments, the tested SMC1A4-chimeric antibody was used as primary antibody (concentration: 1 µg/ml; incubation: 1 hour at room temperature (RT)) and the secondary antibody was an anti-human-Alexa488 antibody (Dilution 1:500; Incubation: 1 hour at RT). FIG. 4C shows immunocytochemistry fluorescence imaging pictures of Pancreatic cancer (Capan1) and colorectal (HT29) cells. Capan1 and HT29 were cells plated in chamber slides and grown in standard culture conditions and after 24 hr. The cells were then fixed with paraformaldehyde and ICC performed with SMC1A4-chimeric antibody and slides analyzed with fluorescence imaging.

Figure 5A:
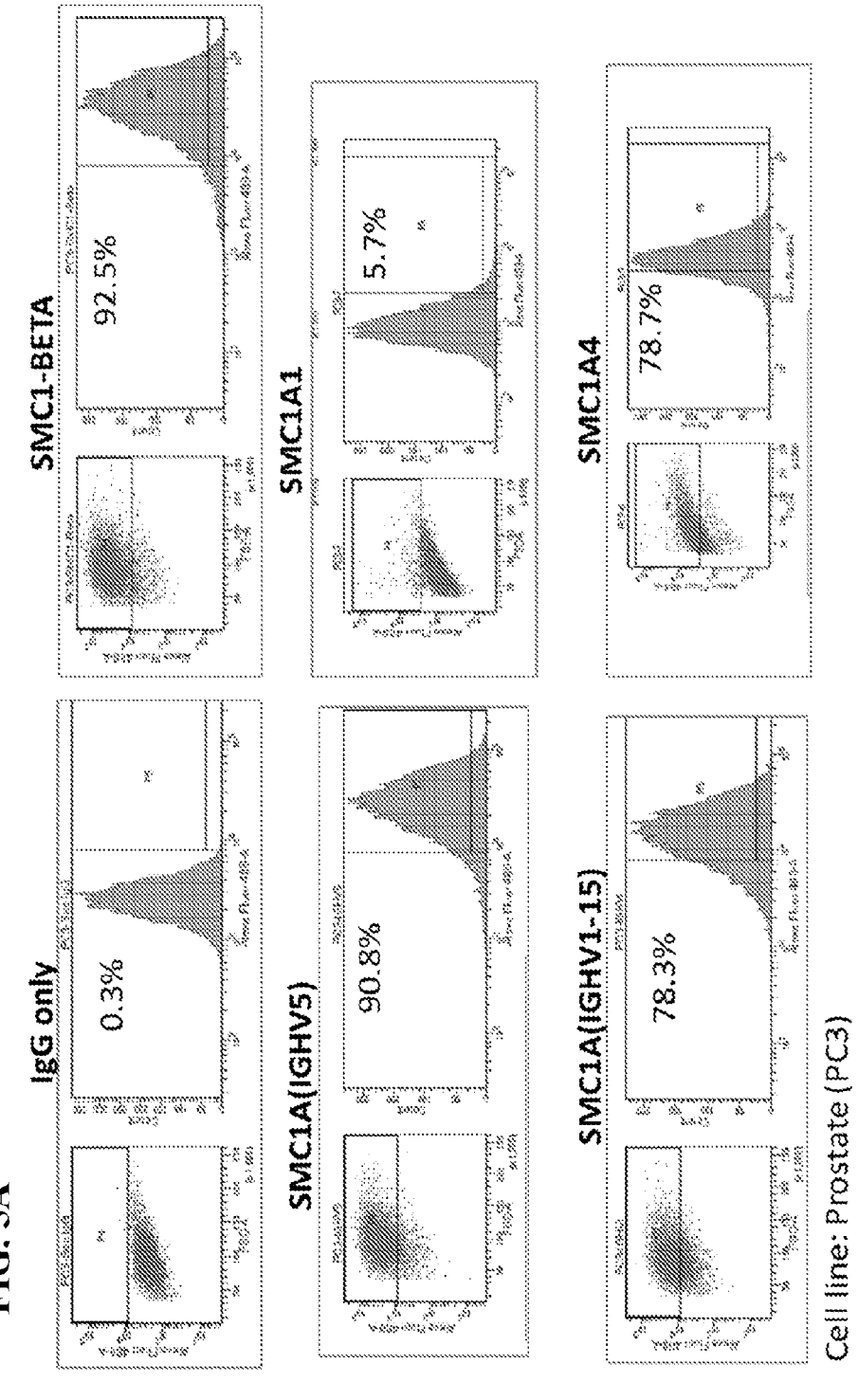
Figure 5B:
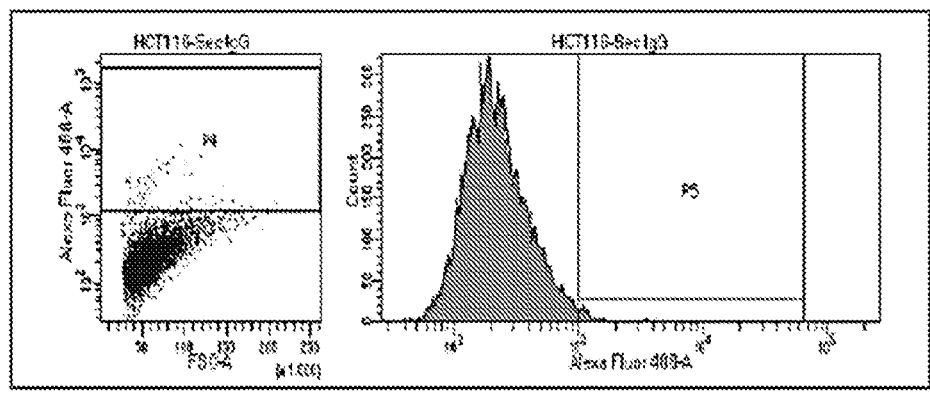
Figure 5B:
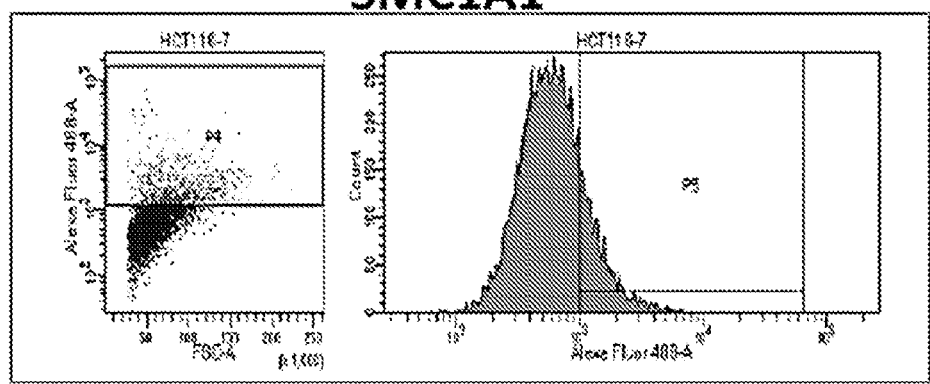
Figure 5B:
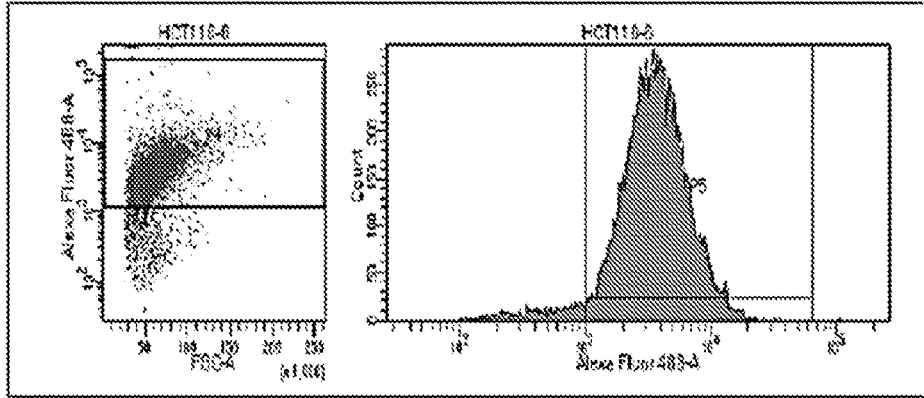
Figure 5C:
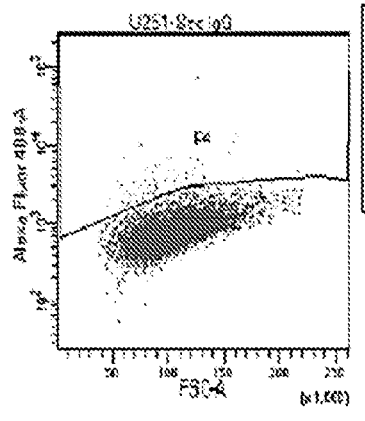
Figure 5C:
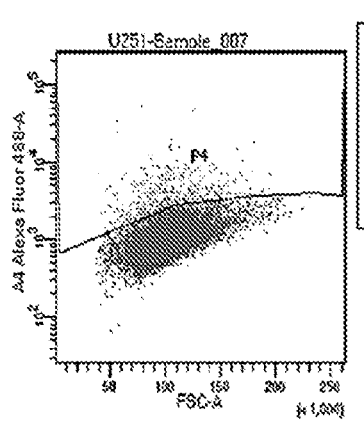
Figure 5C:
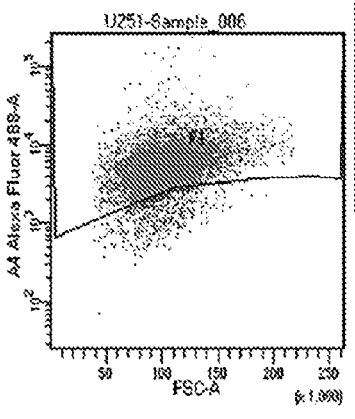

FIGS. 5A-5C are plots showing the detection levels of surface SMC1 using different SMC1-chimeric antibodies by flow cytometry (BD LSRFortessa™), in different cell lines: PC3 (FIG. 5A), HCT116 (FIG. 5B), and U251 (FIG. 5C). In each of these experiments, the tested SMC1A4-chimeric antibody was used as primary antibody (concentration: 1 µg/ml; incubation: 1 hour at room temperature (RT)) and the secondary antibody was an anti-human-Alexa488 antibody (Dilution 1:500; Incubation: 1 hour at RT).

Figure 6A:
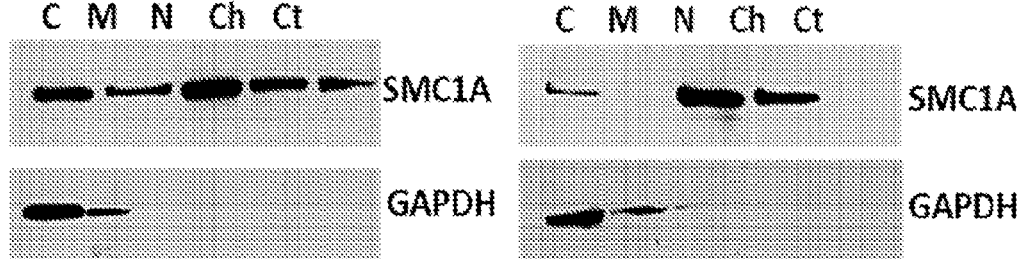
Figure 6B:
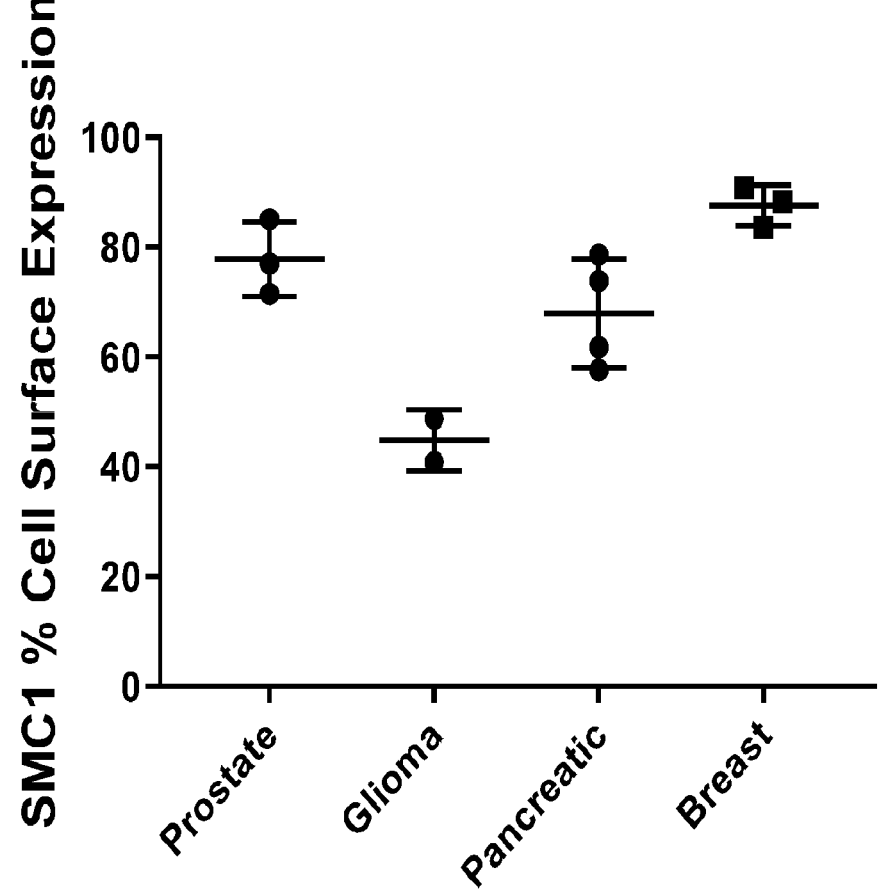
Figure 6C:
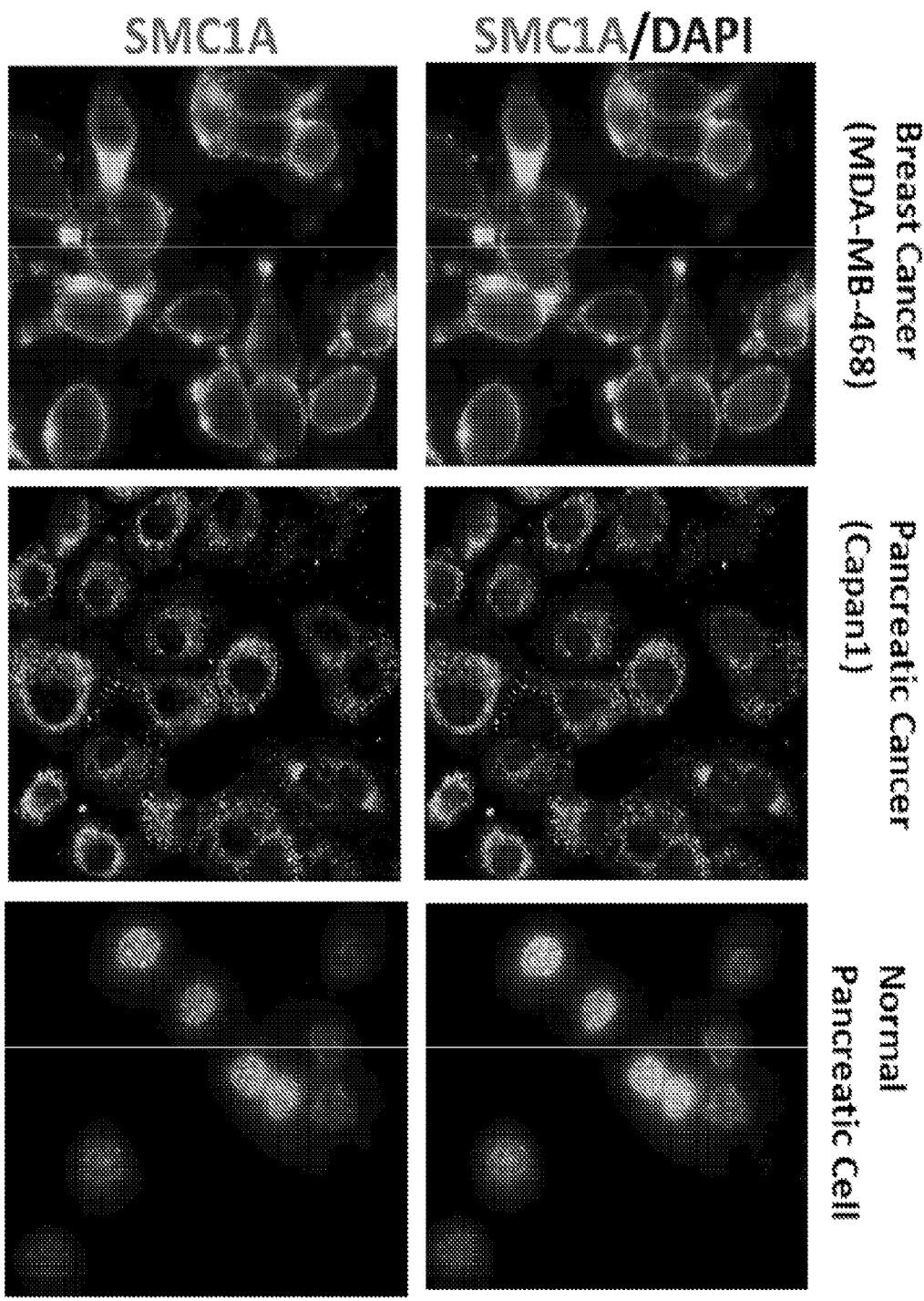

FIGS. 6A-6C show that proprietary SMC1A antibody detected SMC1A antigen on the surface of solid tumor cells. FIG. 6A presents cellular fractionation and Western blot which showed SMC1A localization in cytoplasm (C), membrane (M), nucleus (N), chromatin (Ch) and cytoskeleton (Ct) in pancreatic cancer cells but predominantly nuclear expression in pancreatic normal cells. FIG. 6B is a flow cytometry (BD LSRFortessa™) plot showing quantification of surface expression of SMC1A in live cultured cancer cells (pancreatic, prostate, glioblastoma and breast cancer cells) after incubation with humanized SMC1A-antibody SMC1A4. FIG. 6C shows fluorescence microscopy pictures of breast cancer cells (MDA-MB-468), pancreatic cancer cells (Capan1 cells) and normal pancreatic cells, stained by immunocytochemistry (ICC) for SMC1A and DAPI. The cells (~20,000 cells/well) were plated in slides and grown in culture. After 24 hrs, cells were fixed and ICC was performed with primary antibody SMC1A4, and slides analyzed with fluorescence imaging.

Figure 7:
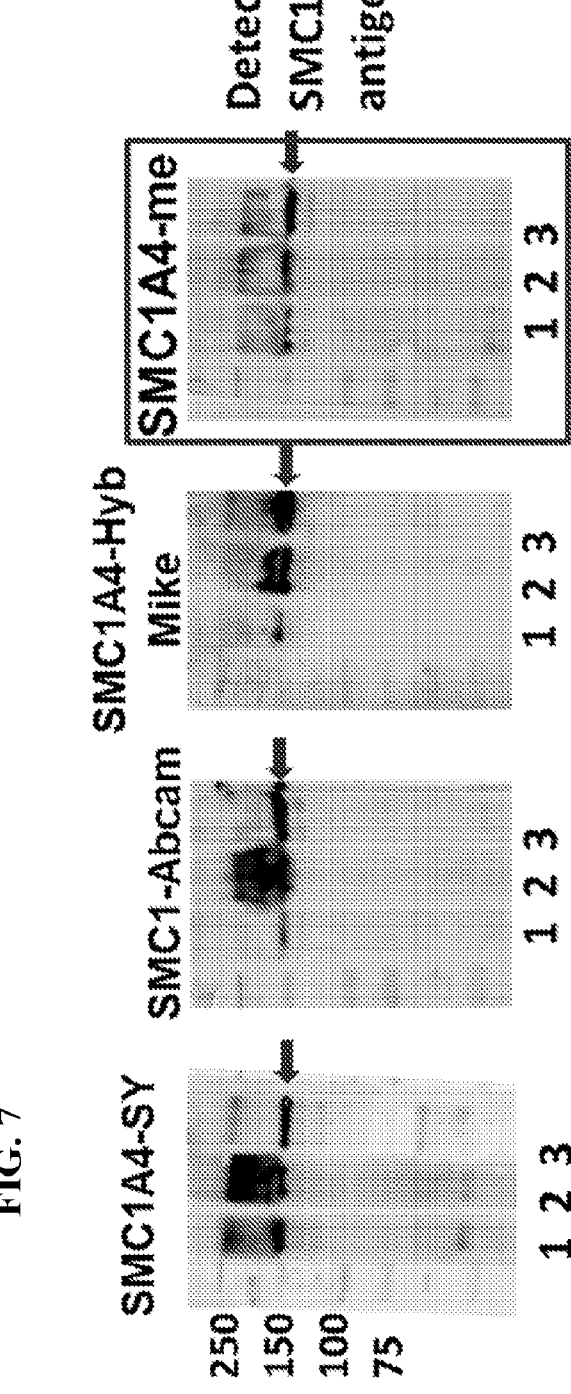

FIG. 7 presents Western blot pictures showing that SMC1A4-me detected SMC1A antigen in cancer cells. For each Western blot, the cell lysates used as samples were from HCT116 cells (1), HT29 cells (2) and MDA-MB-231 cells (3). In these experiments, the primary antibodies used were SMC1A4-mouse (dilution: 1 µg/ml), SMC1A4-me (dilution: 1 µg/ml), or SMC1-Abcam (dilution: 1:1000), and incubated with the cell lysates overnight at 4° C. The secondary antibody used was an anti-human-HRP (dilution 1:3000) and incubated for 1 hour at room temperature with the overnight incubations.

Figure 8A:
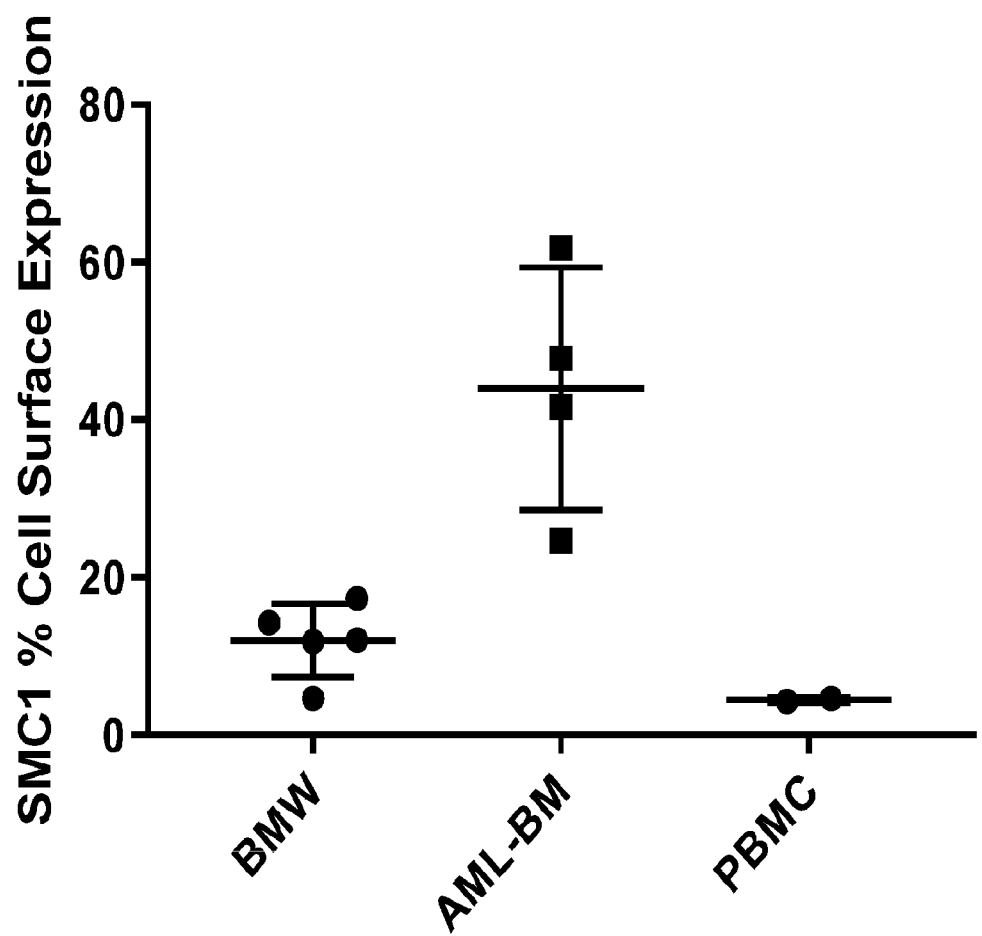
Figure 8B:
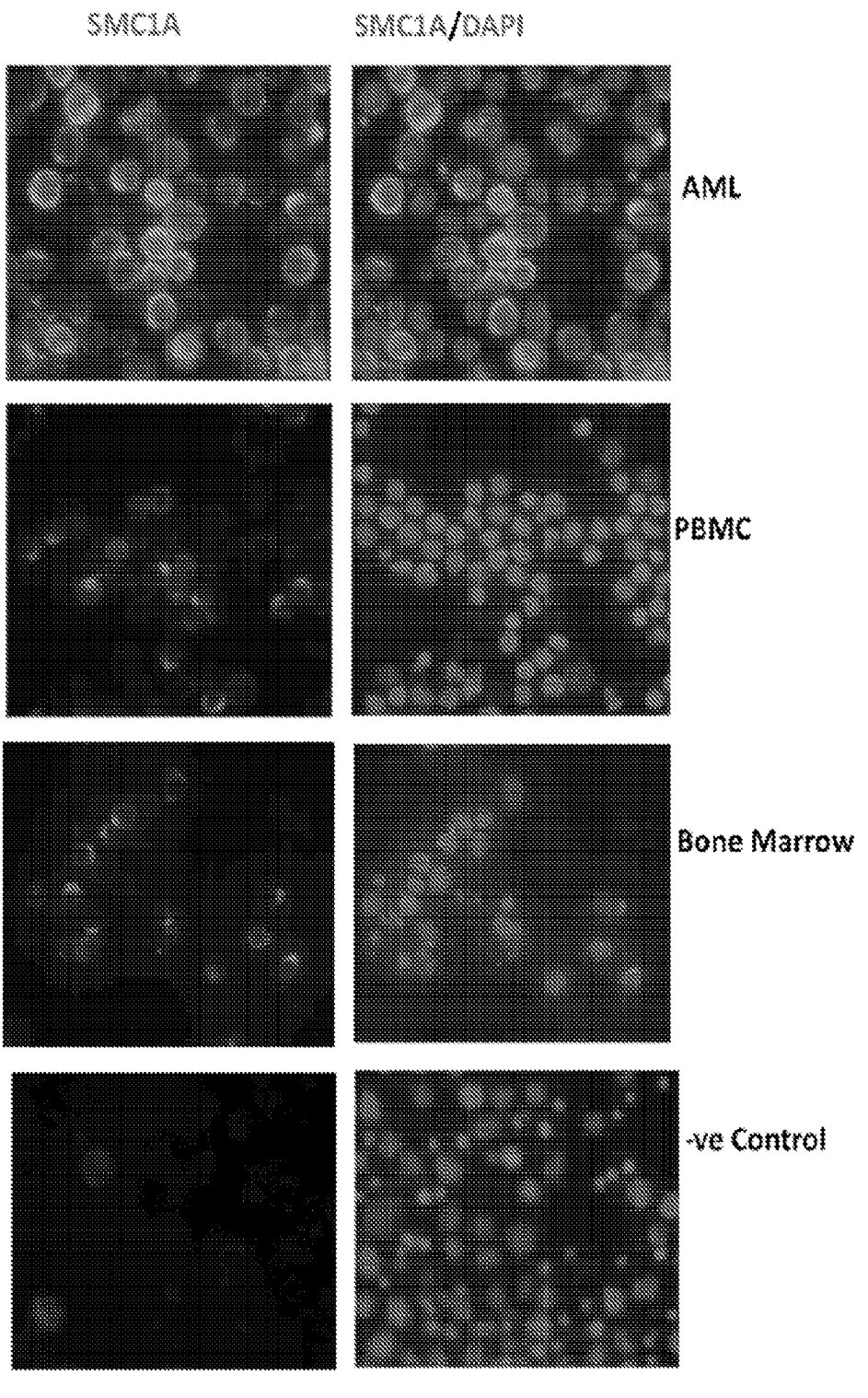

FIGS. 8A-8B show that SMC1A4-ME antibody detects SMC1A antigen on the surface of AML cells but not in normal cells. FIG. 8A is a flow cytometry (BD LSR-Fortessa™) plot showing that SMC1A4 detected the SMC1A antigen on the surface of AML cells. In this experiment, AML-BM cells from patients, BMW (bone marrow cells) and PBMCs (peripheral blood mononuclear cells) were cultured and incubated with humanized SMC1A-antibody (SMC1A4) and cells with surface expression of SMC1A was quantified by flow cytometry. FIG. 8B shows fluorescence microscopy pictures of AML, PBMC, bone marrow and control cells stained view immunocytochemistry ICC with SMC1A-directed antibody SMC1A4. In this experiment, SMC1A4 detected the SMC1A antigen on the surface of AML cells.

Figure 9:
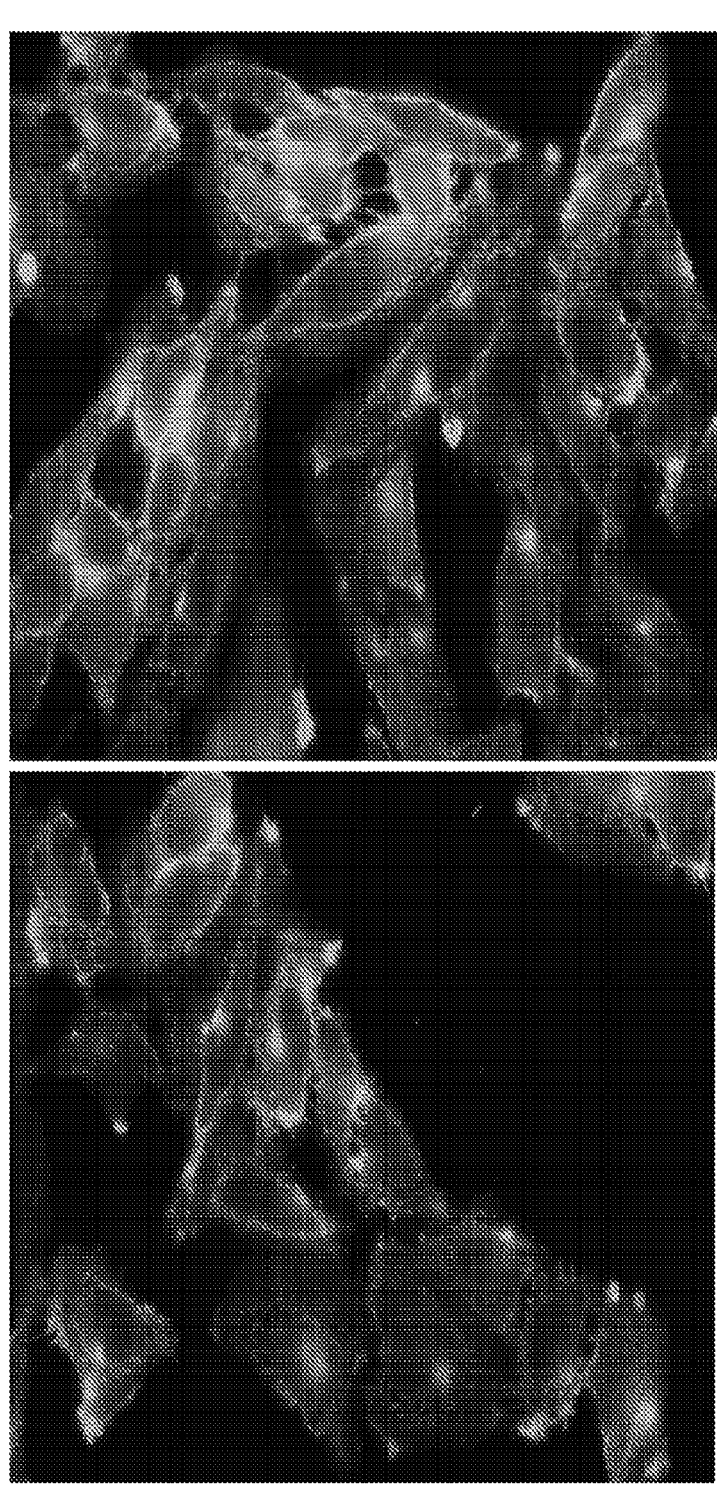

FIG. 9 shows fluorescence microscopy pictures of cells from the U251 glioblastoma cell line stained via immunocytochemistry with the SMC1A4-me antibody. In this experiment, the primary antibody used was SMC1-A4 me (dilution: 1:100; incubation: 2 hours at room temperature) and the secondary antibody was an anti-human-FITC (dilution 1:500; incubation: 1 hour at room temperature).

Figure 10:
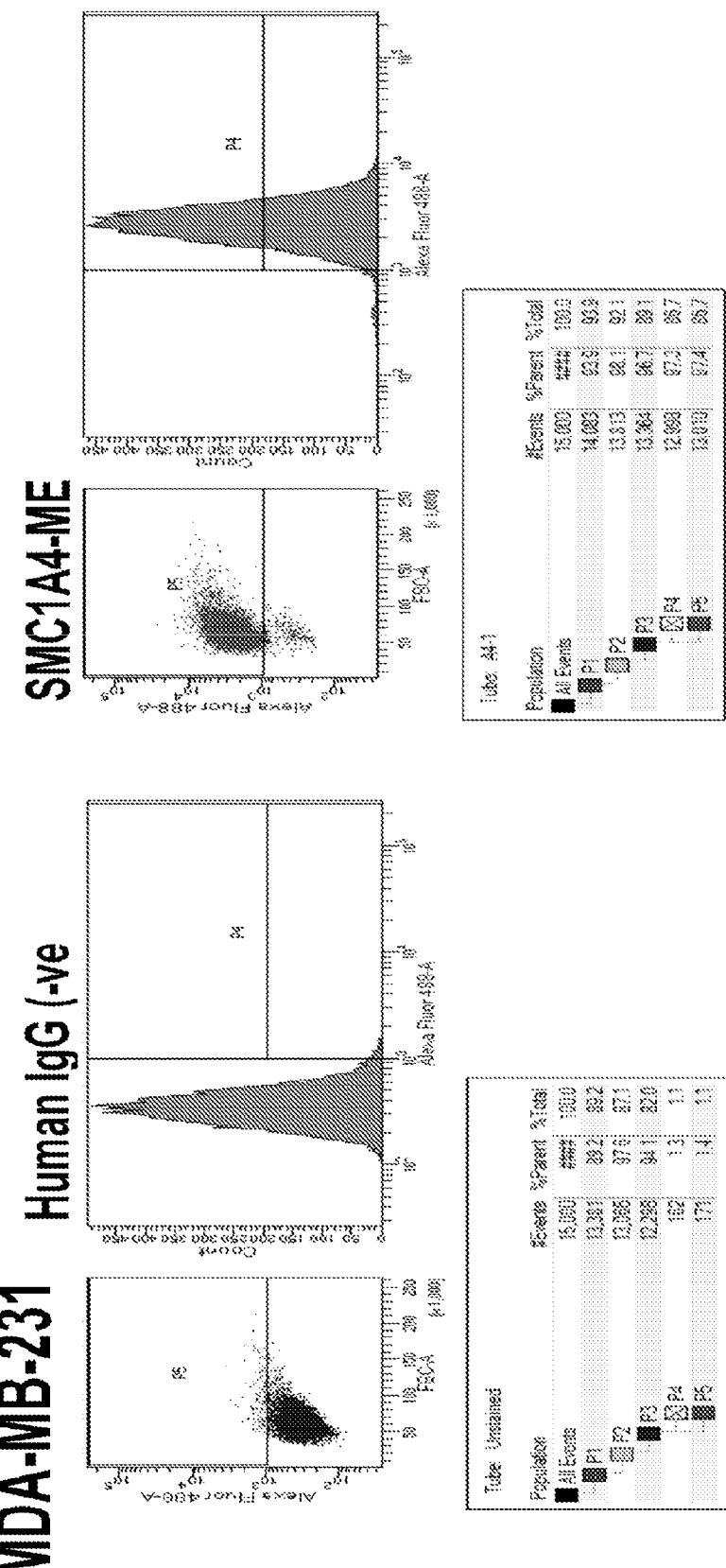

FIG. 10 presents flow cytometry plots showing that SMC1A4-me detect surface expression of SMC1 on live cells (MDA-MB-213 and MDA-MB-468 cell lines).

Figure 11A:
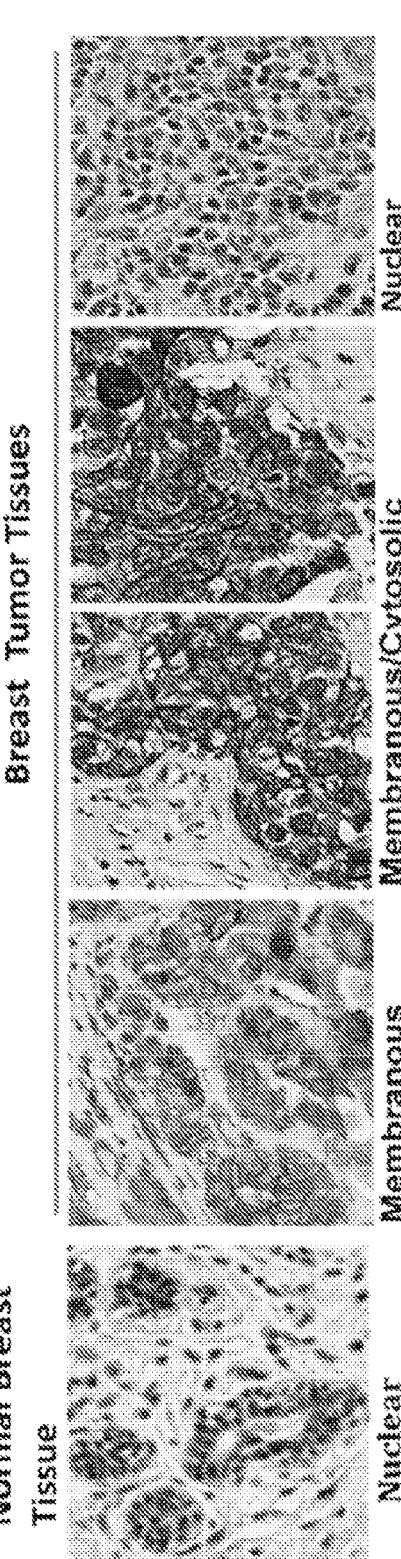
Figure 11B:
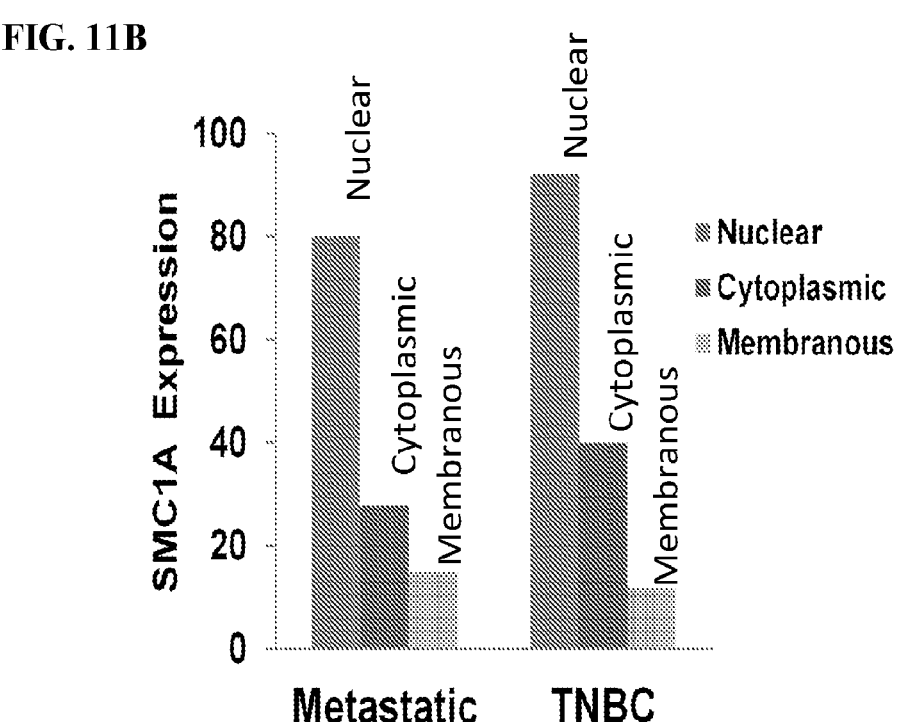
Figure 11C:
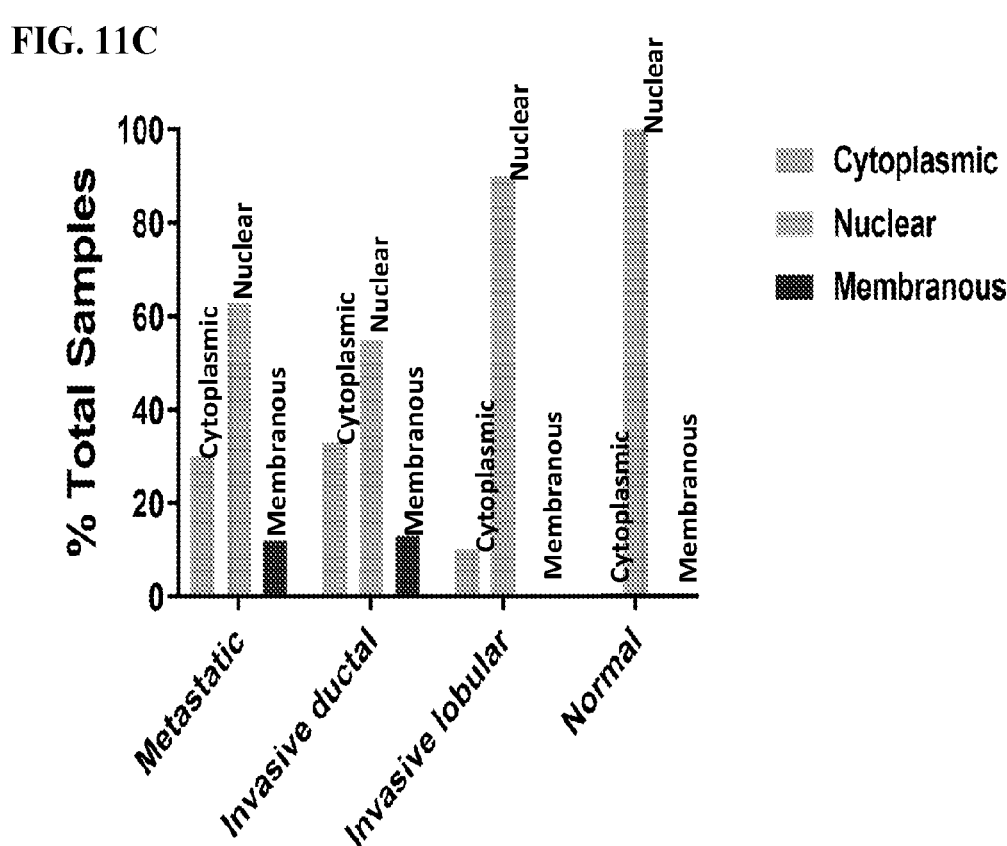

FIGS. 11A-11C presents data showing expression and localization of SMC1A in breast tumors and normal tissues. FIG. 11A shows microscopy pictures of the expression and subcellular localization of SMC1A as tested in breast cancer tissues by immunohistochemistry. SMC1A staining was more intense in cancer cells than normal breast tissues. In normal tissues, SMC1A showed nuclear expression while in breast tumor sections SMC1A showed nuclear, cytoplasmic and membranous expression. FIG. 11B is a bar graph showing the SMC1A nuclear, cytoplasmic, or membranous expression of SMC1A in metastatic tissue or triple-negative breast cancer (TNBC) tissue. FIG. 11C is a bar graph showing the percentage of total samples showing cytoplasmic, nuclear, or membranous expression of SMC1A in either metastatic, invasive ductal, invasive lobular or normal tissues. SMC1A showed membranous expression in about 12% of TNBC samples and in 15% of samples from metastatic sites. In normal tissues, SMC1A showed nuclear expression.

Figure 12:
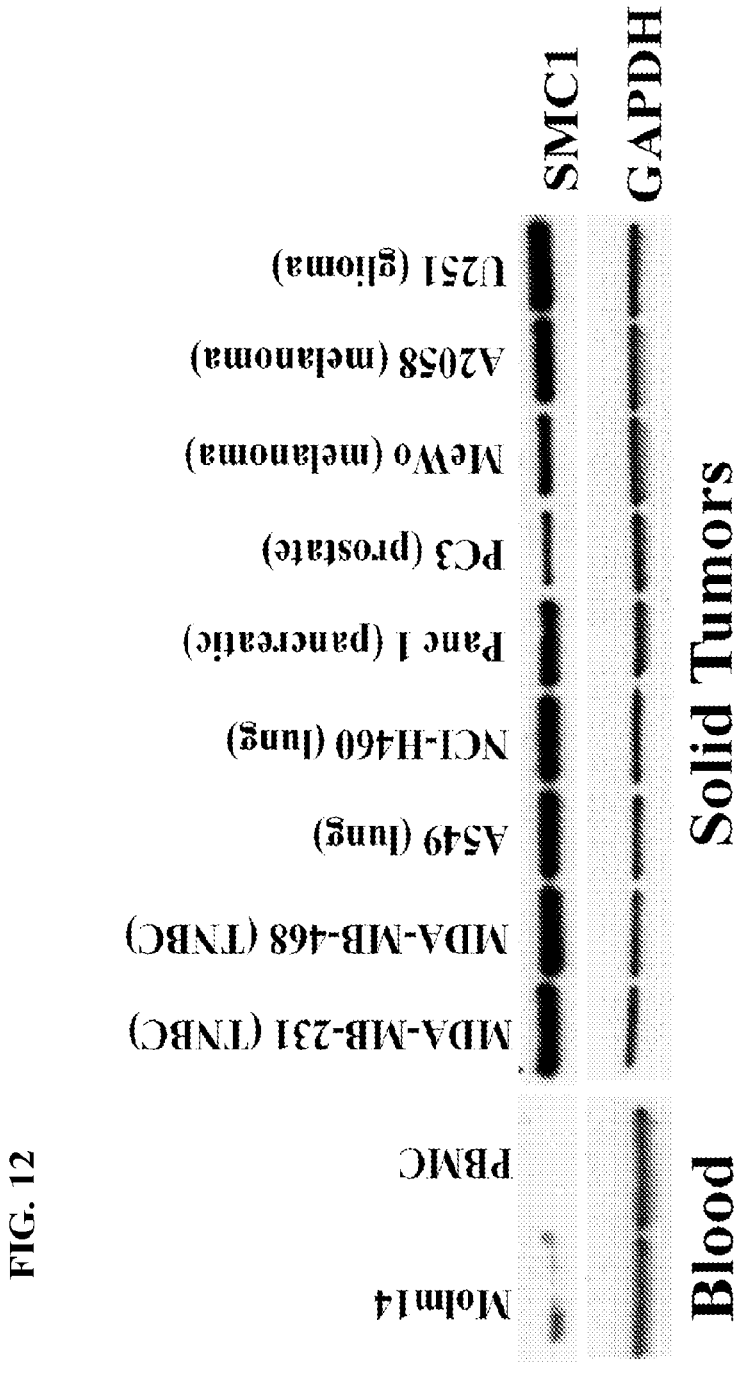

FIG. 12 is a picture of a Western blot experiment which showed differential expression of SMC1A in human cancers.

Figure 13A:
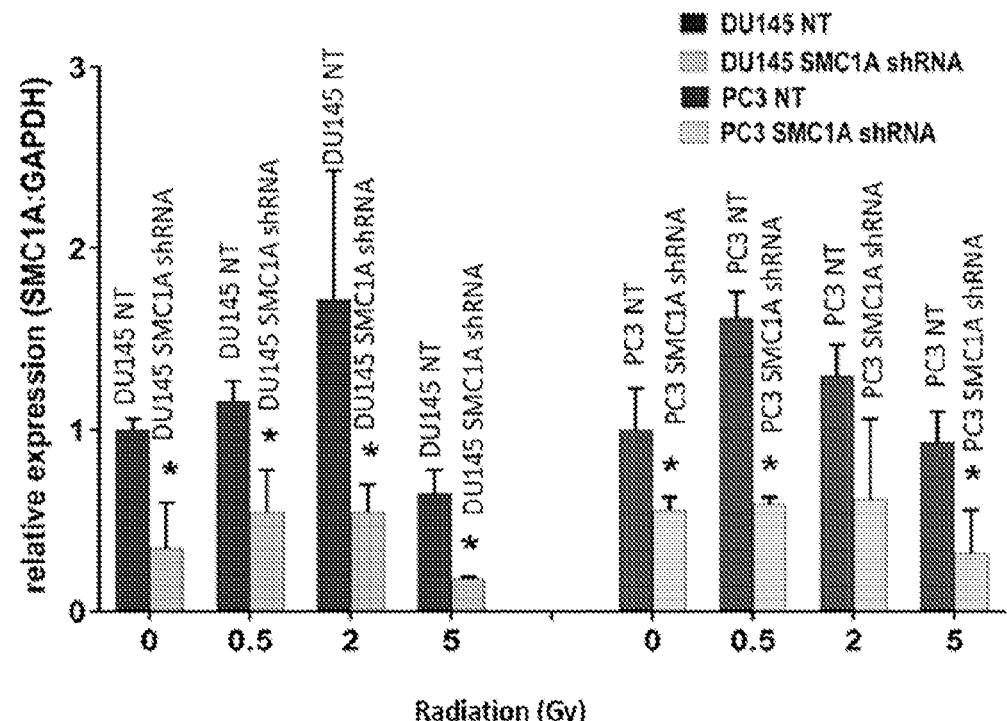
Figure 13B:
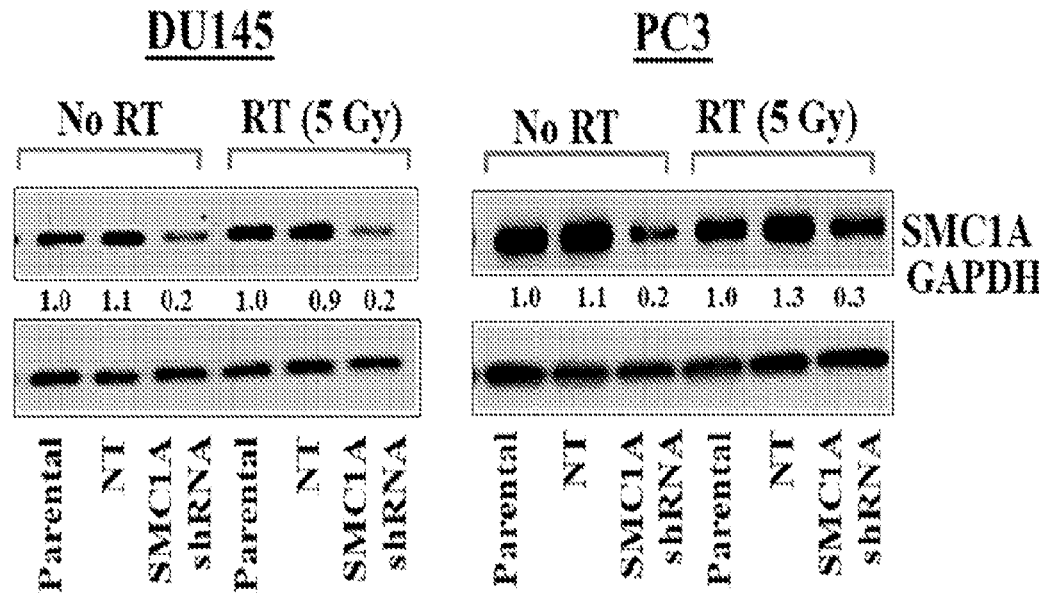
Figure 13C:
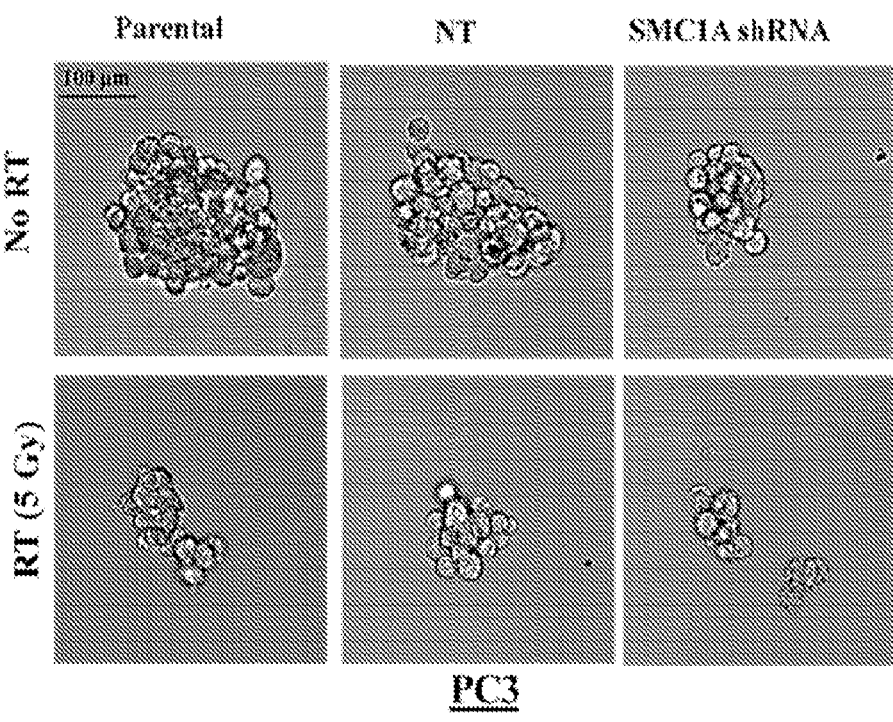
Figure 13C:
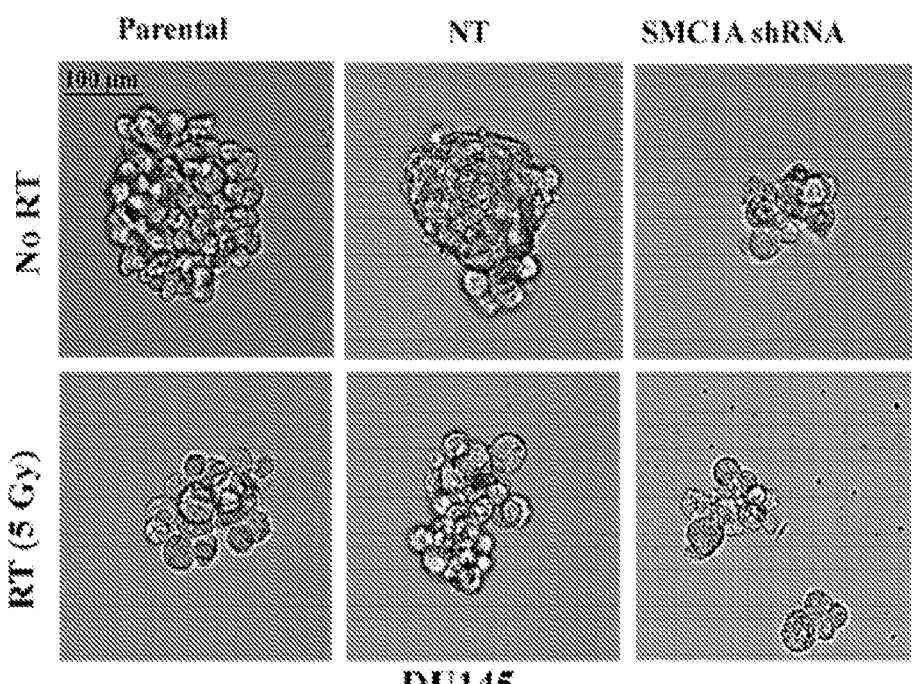

FIGS. 13A-13C show that SMC1A knockdown attenuated sphere formation and sensitized prostate cancer cells towards x-irradiation. FIG. 13A shows that SMC1A expression was detected by 48 hours after irradiation by qRT-PCR in NT shRNA and SMC1A shRNA expressing DU145 and PC3 cells. SMC1A expression was significantly reduced in both DU145-SMC1A shRNA and PC3-SMC1A shRNA cells, compared to their corresponding NT shRNA expressing cells (*P<0.05). FIG. 13B shows Western blot analysis protein expression in parental, NT shRNA and SMC1A shRNA expressing DU145 and PC3 cells with GAPDH as a loading control. The expression of SMC1A was reduced to ~20% and 30% in DU145-SMC1A shRNA and PC3-SMC1A shRNA cells respectively compared to their NT shRNA controls. FIG. 13C shows the ability of prostate cancer cells to form spheres was tested in x-irradiated and non-irradiated parental, NT and SMC1A shRNA expressing cells. Sphere formation was evaluated every 24 hr for up to 5 days and quantitated at day 5 by counting spherical cell clusters (>60 µm) in 10 random fields. Representative images captured by fluorescence microscope (Zeiss Observer II) at 10× exposure are shown.

Figure 14A:
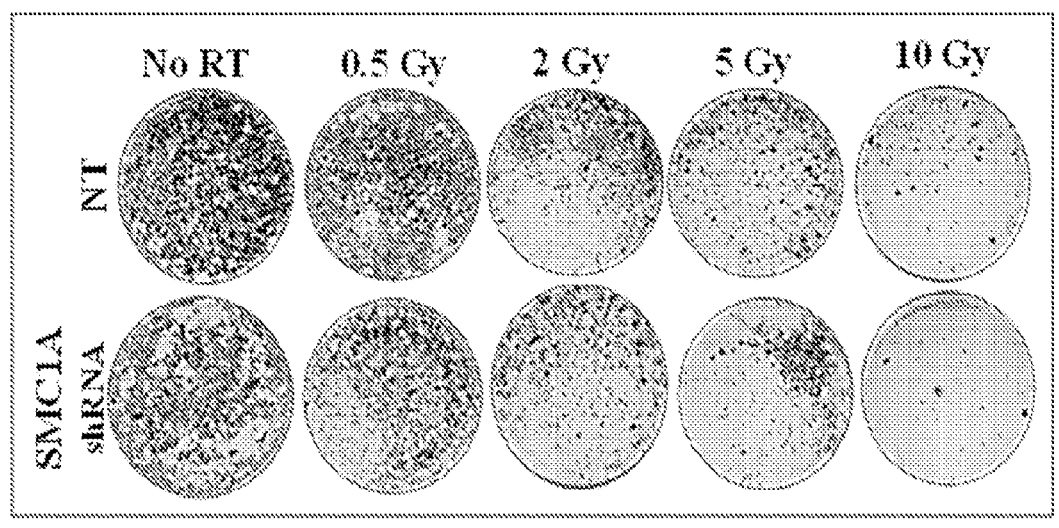
Figure 14B:
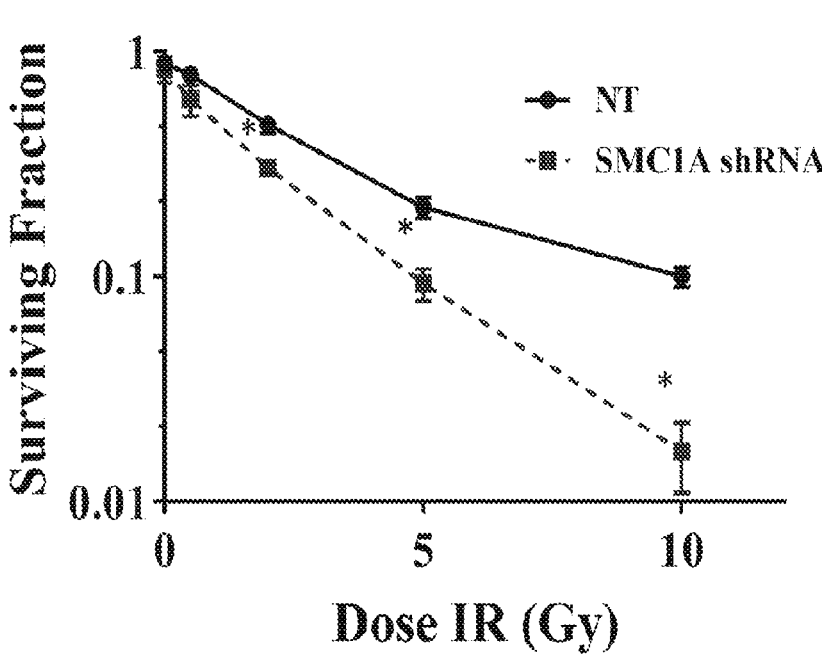
Figures 14C, 14D:
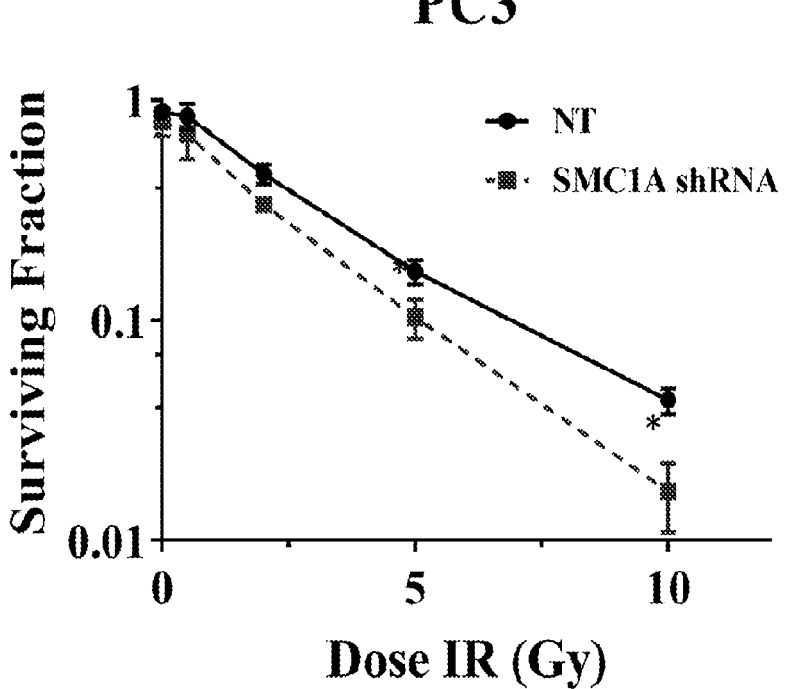

FIGS. 14A-14D show that SMC1A knockdown radio sensitized prostate cancer cells and limited their colony survival potential. FIGS. 14A-14B show the clonogenic survival of SMC1A shRNA expressing DU145 cells was reduced compared to their corresponding NT shRNA expressing cells after a single dose radiation (0, 0.5, 2, 5 and 10 Gy) with the X-RAD SmART system (225 keV) delivered at a rate of 150 cGy/min (1.5 Gy/min). FIGS. 14C-14D show that the clonogenic survival of SMC1A shRNA expressing PC3 cells was reduced compared to their corresponding NT shRNA expressing cells after a single dose radiation (0, 0.5, 2, 5 and 10 Gy) with the X-RAD SmART system (225 keV) delivered at a rate of 150 cGy/min (1.5 Gy/min). In FIG. 14B and FIG. 14D, data were fitted according the linear quadratic model. All results were from three independent experiments (Mean±SD, n=3).

Figure 15A:
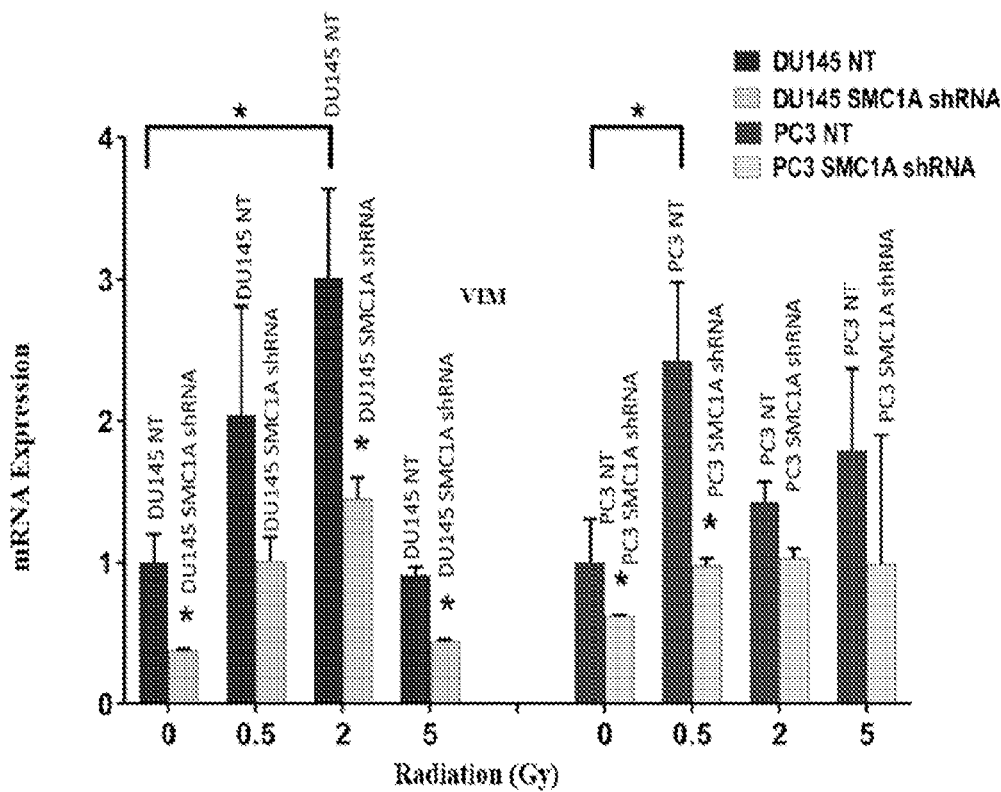
Figure 15B:
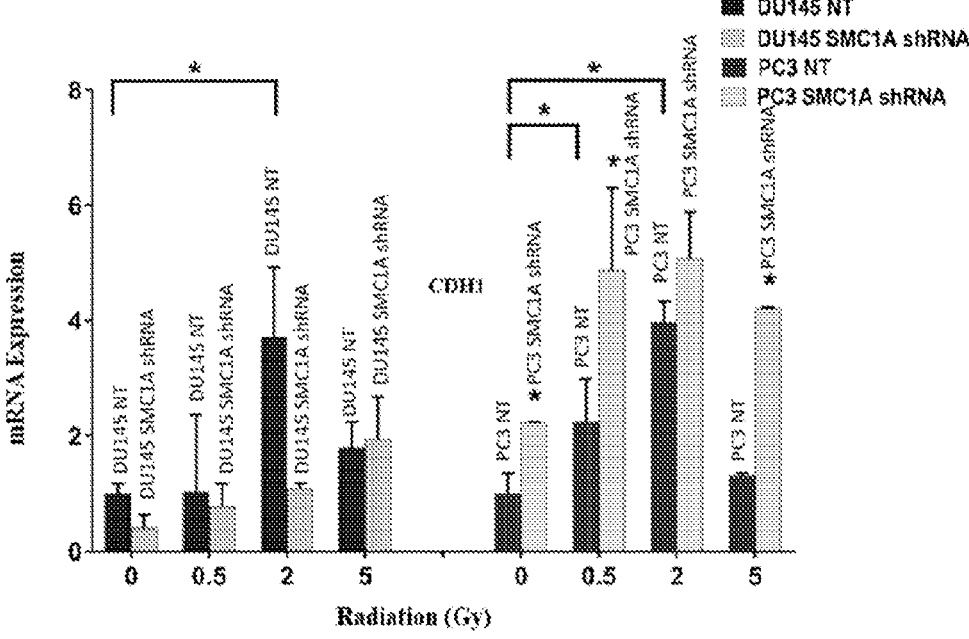
Figure 15C:
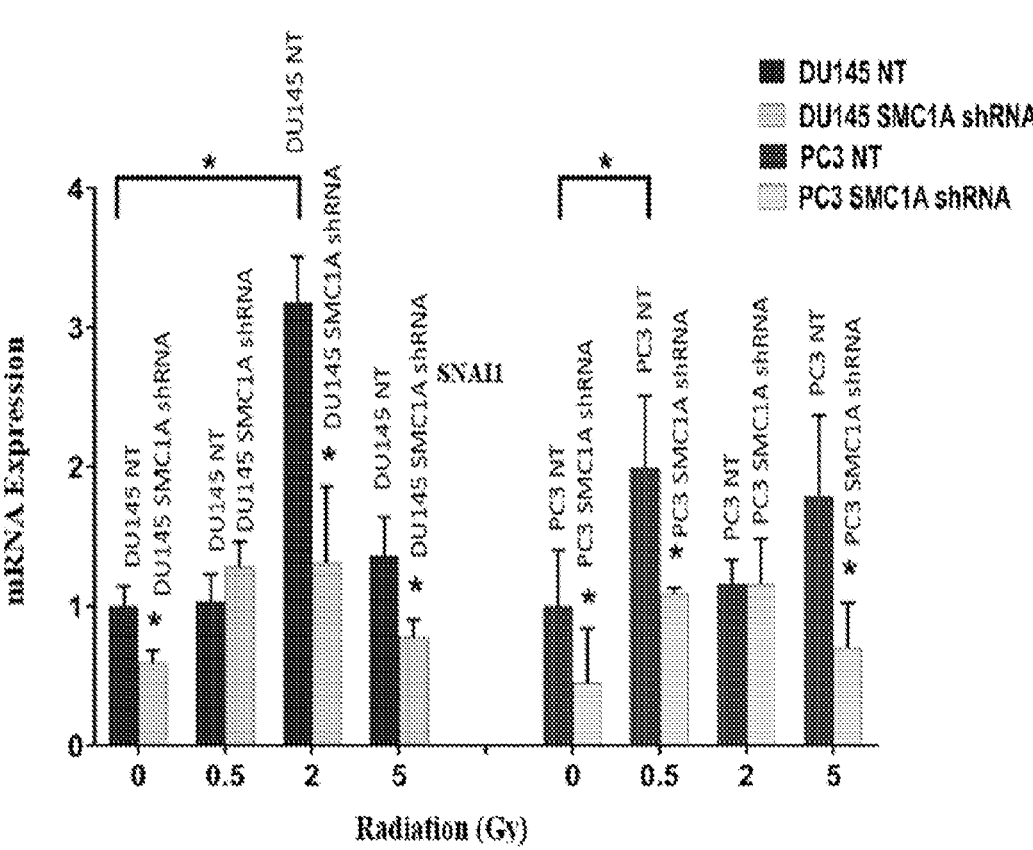
Figure 15D:
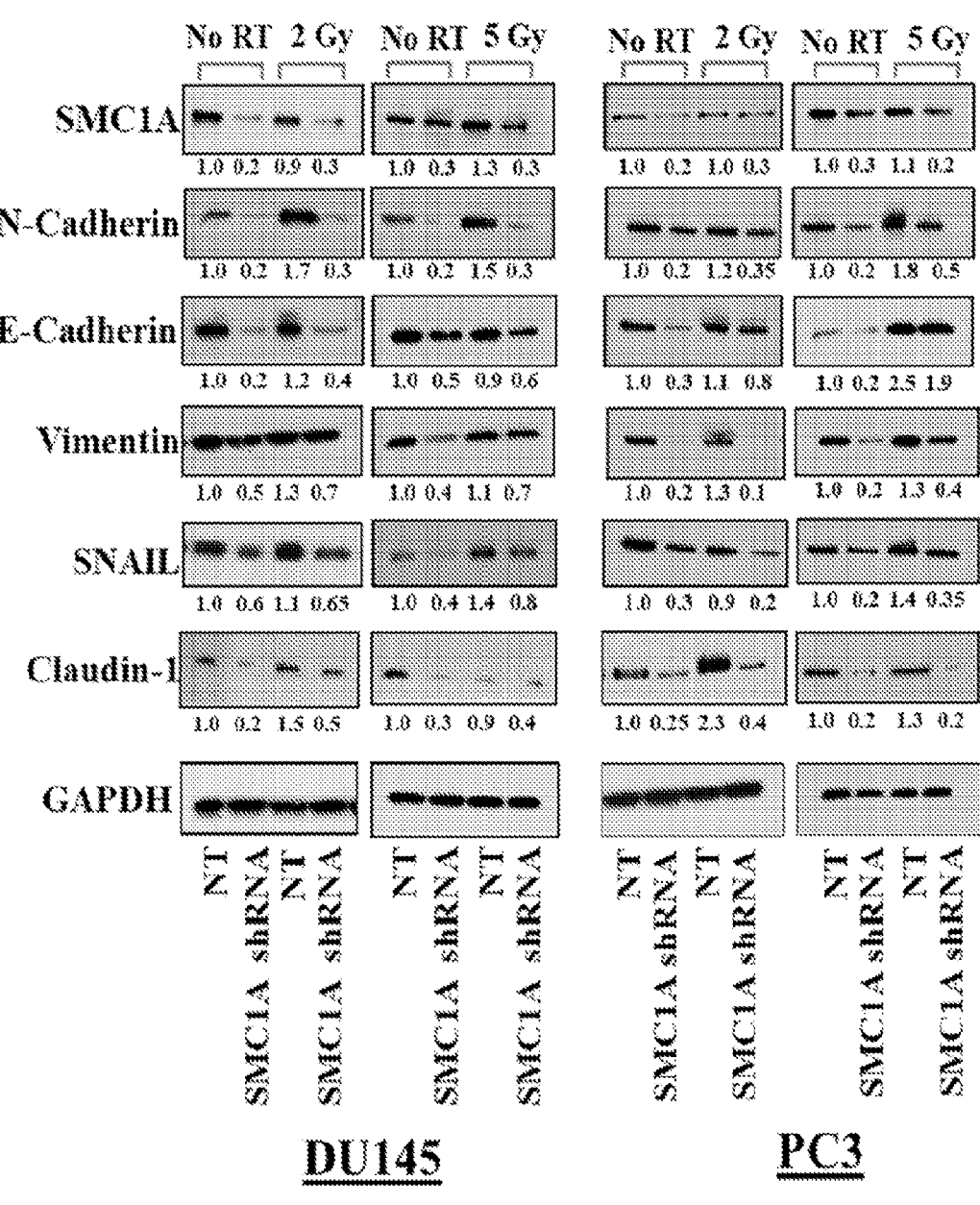

FIGS. 15A-15D show that SMC1A regulated EMT in control and irradiated prostate cancer cells. FIG. 15A-15C are bar graphs showing that the expression of genes involved in EMT was tested by qRT-PCR in NT shRNA and SMC1A shRNA expressing DU145 and PC3 cells irradiated (0-5 Gy) and grown in standard culture conditions for 48 hr. Data showed lower levels of VIM (FIG. 15A), CDH1 (FIG. 15B) and SNAI1 (FIG. 15C) in cells transduced with SMC1A shRNA compared to their respective NT shRNA expressing cells. These EMT genes were overexpressed in x-irradiated cells, but their expression was significantly lower in SMC1A knockdown cells. Asterisks indicate statistically significant differences (p<0.05). FIG. 15D shows Western blot quantification of the expression of EMT marker proteins (N-cadherin, E-cadherin, Vimentin, Snail and Claudin-1). Asterisks indicate statistically significant difference (p<0.05).

Figure 16A:
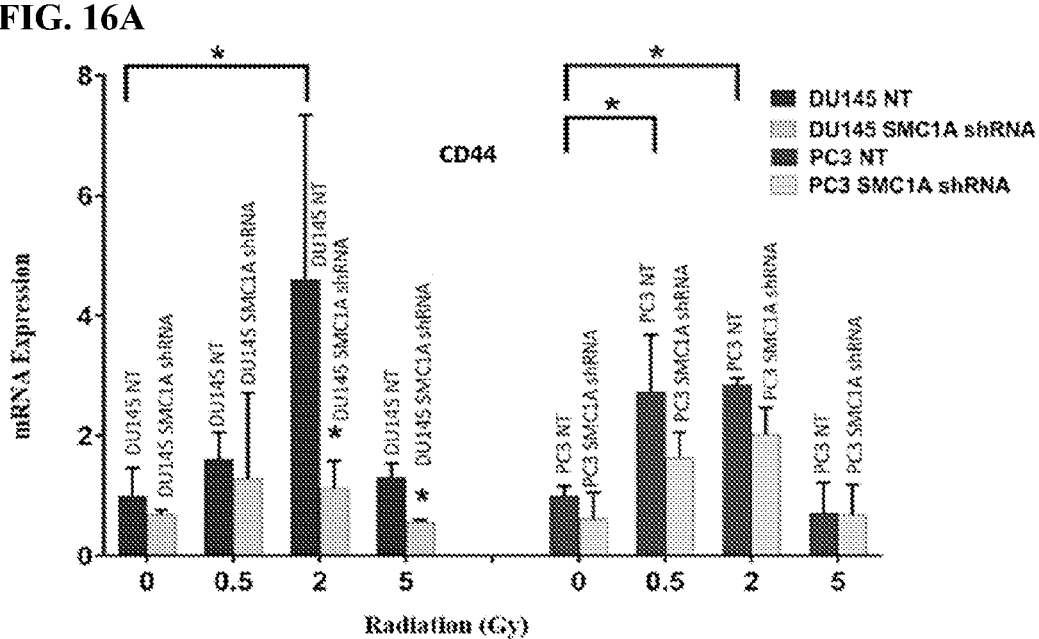
Figure 16B:
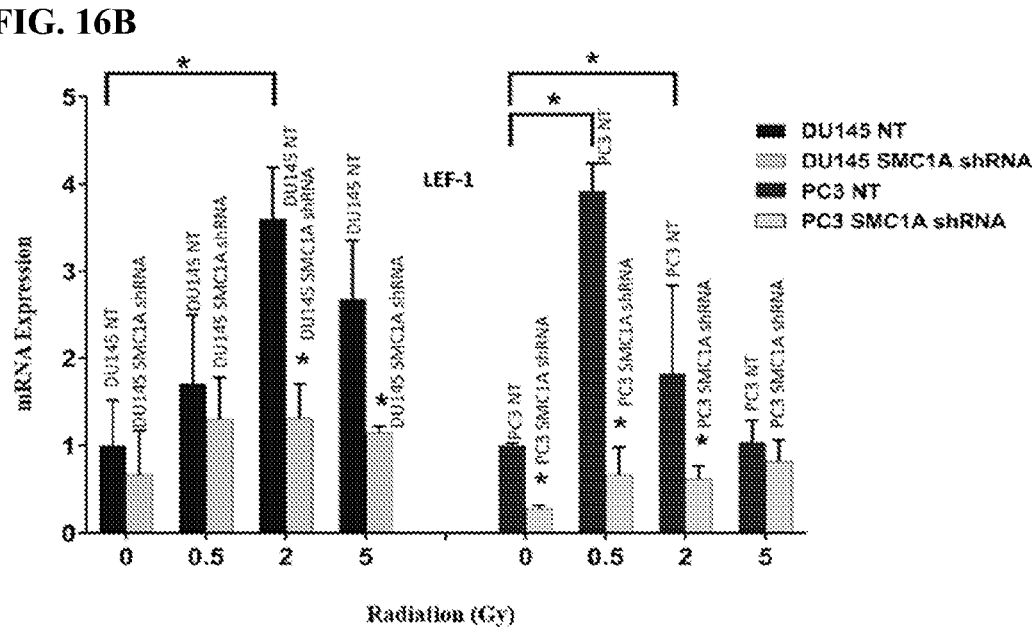
Figure 16C:
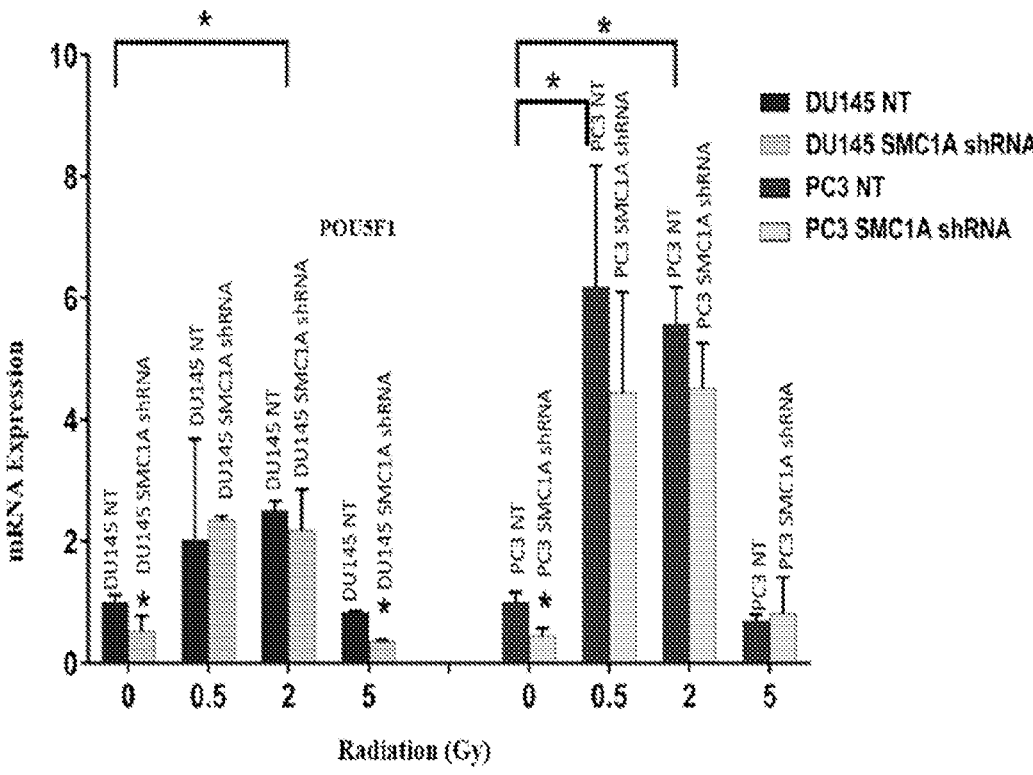
Figure 16D:
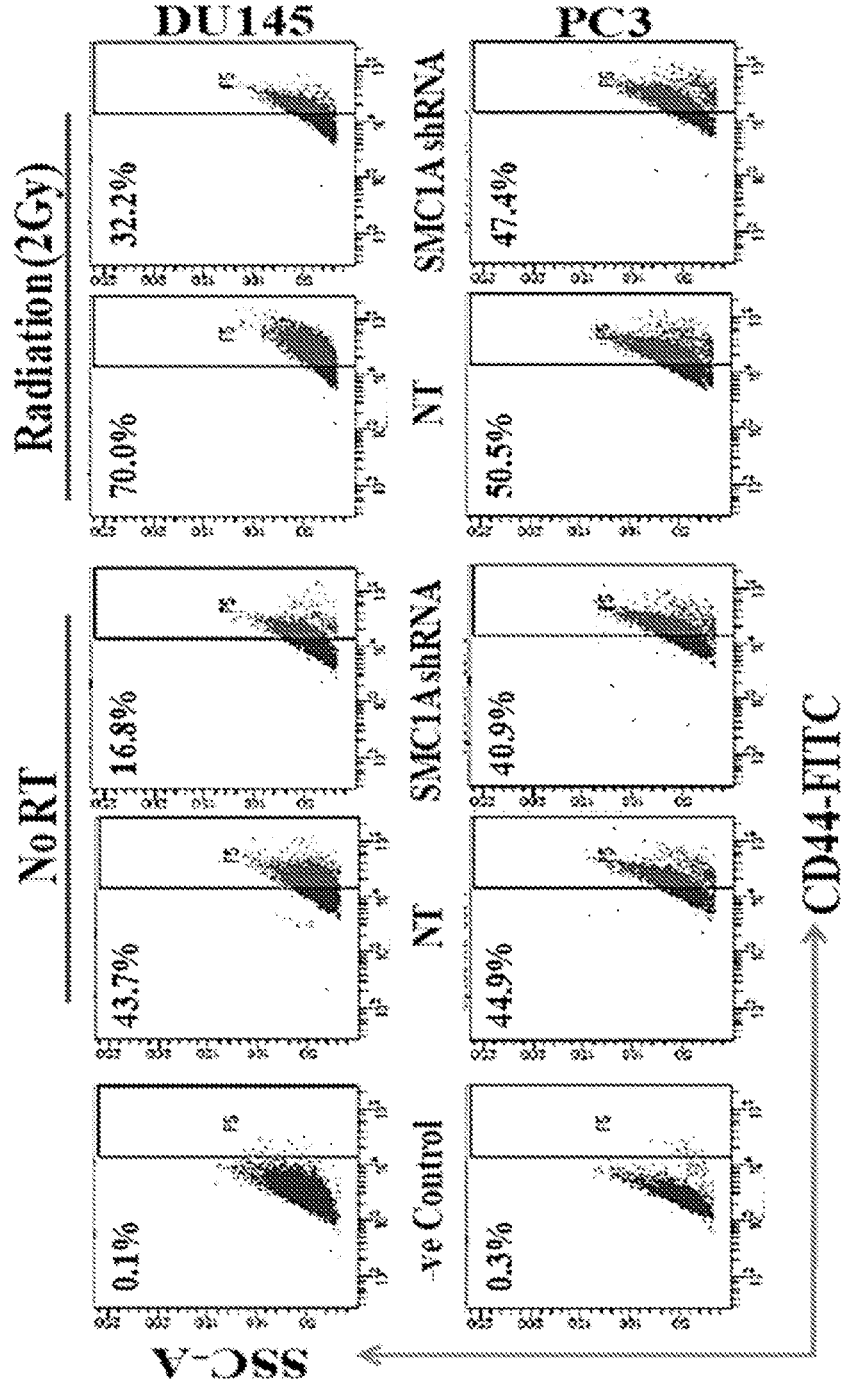
Figure 16E:
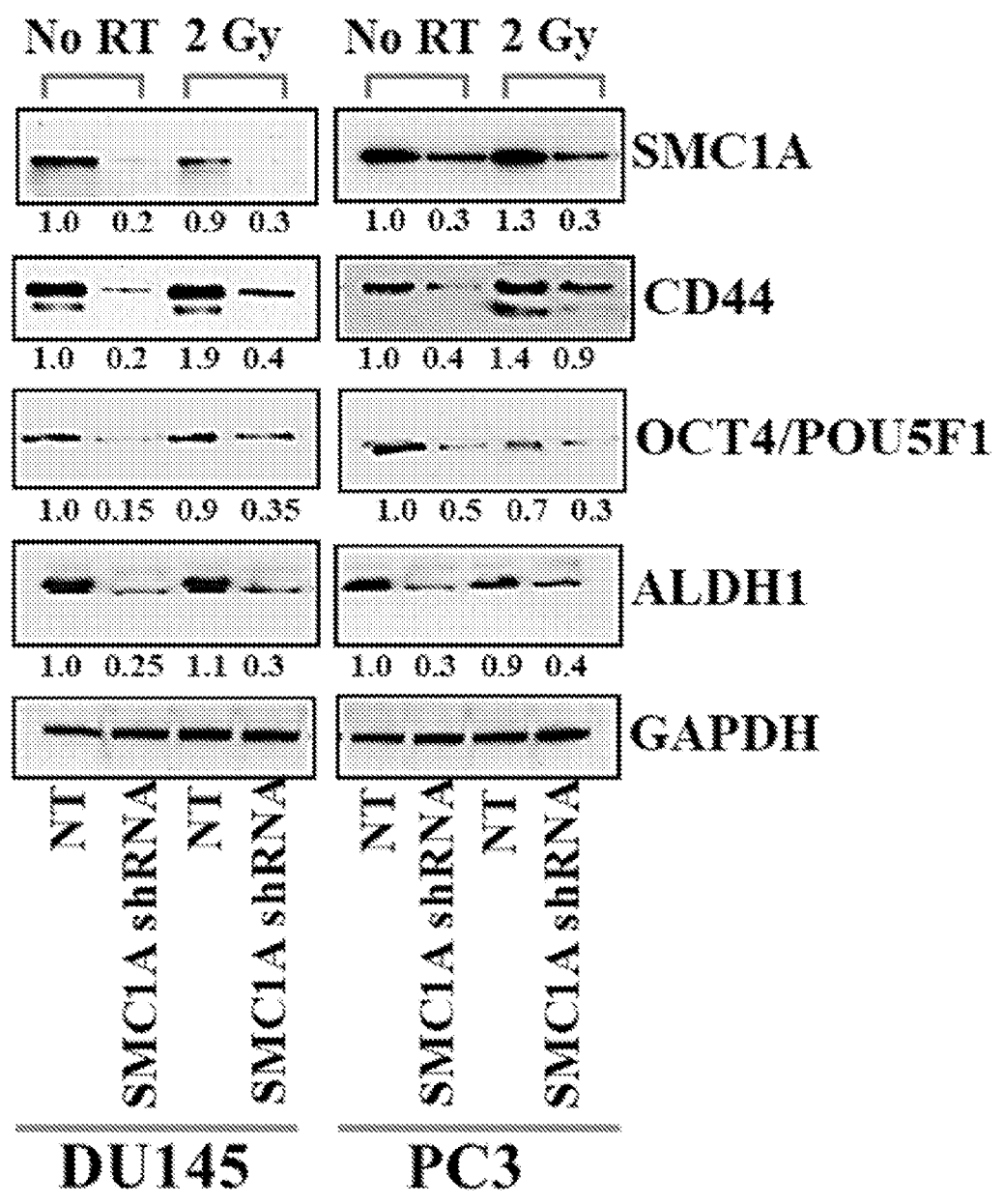

FIGS. 16A-16E show that SMC1A regulated CSCs in control and x-irradiated prostate cancer cells. FIGS. 16A-16C are bar graphs showing the measurement of the expression of stem cell markers, CD44, LEF1 and POU5F1 in DU145-SMC1A shRNA and PC3-SMC1A shRNA cells irradiated (0-5 Gy) and grown in standard culture conditions for 48 hr, by qRT-PCR. FIG. 16D show the quantification of the expression of CD44 by flow cytometry in control and SMC1A expressing DU145 and PC3 cells x-irradiated with clinically relevant dose (2 Gy). FIG. 16E presents a Western blot experiment in which the expression of stem-like cell markers, POU5F1, CD44 and ALDH1 was checked in control and x-irradiated (2 Gy) NT and SMC1A shRNA expressing DU145 and PC3 cells by Western blot. Data showed that SMC1A regulated the expression of stem-like cells in x-irradiated and control cells.

Figure 17A:
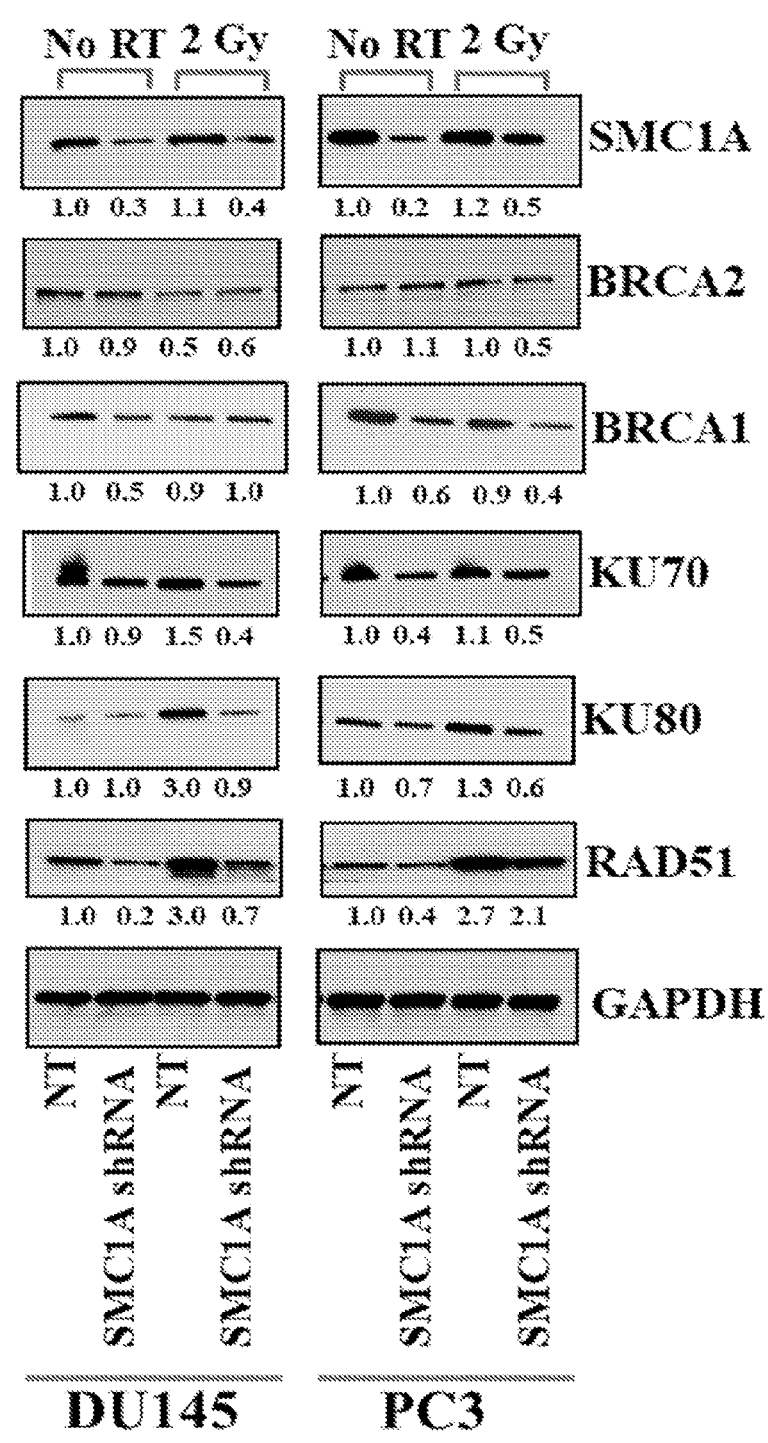
Figure 17B:
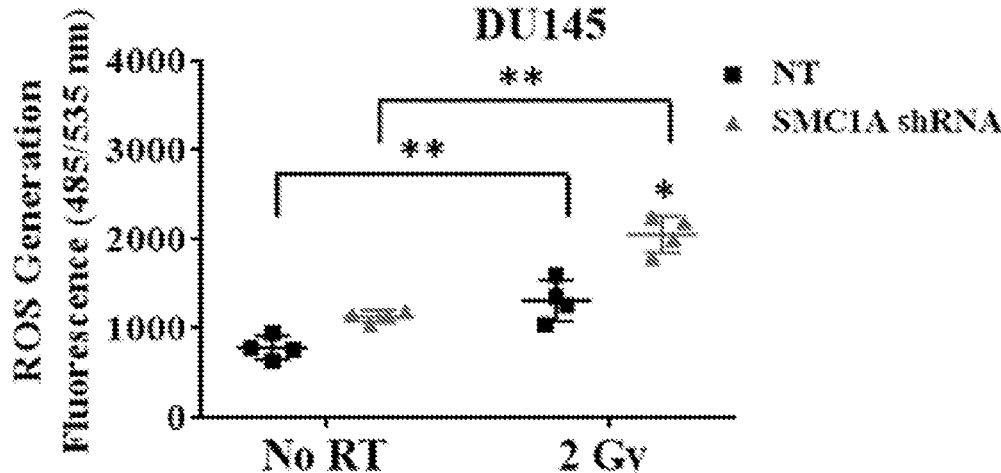
Figure 17C:
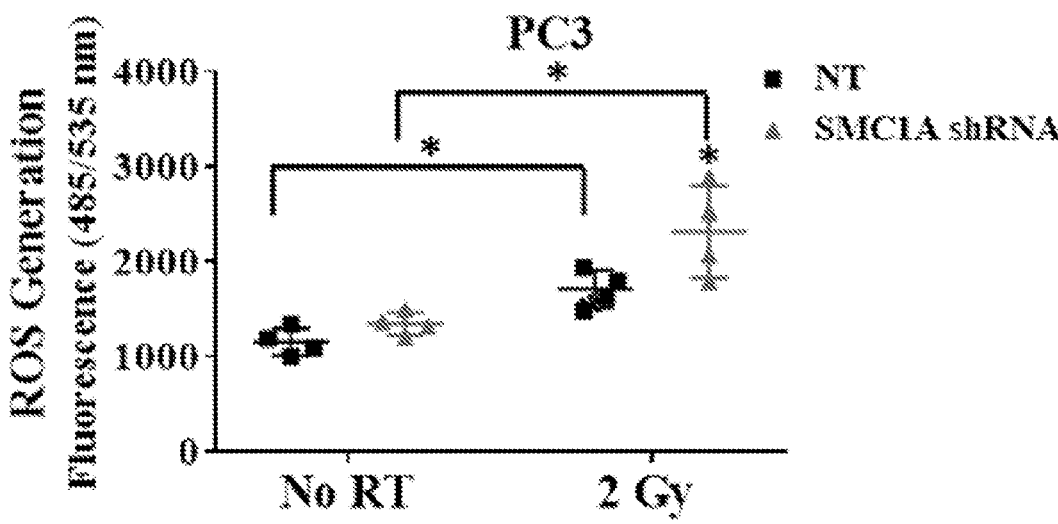
Figure 17D:
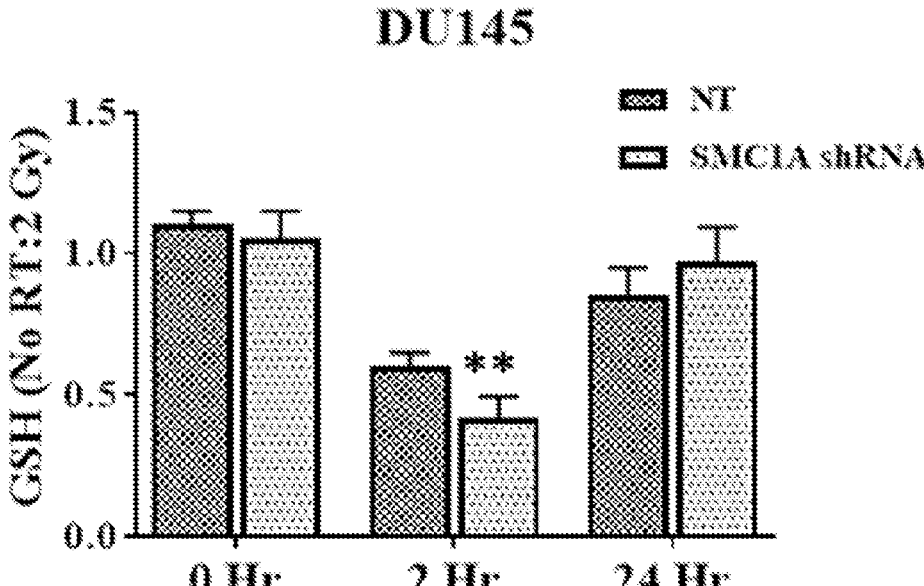
Figure 17E:
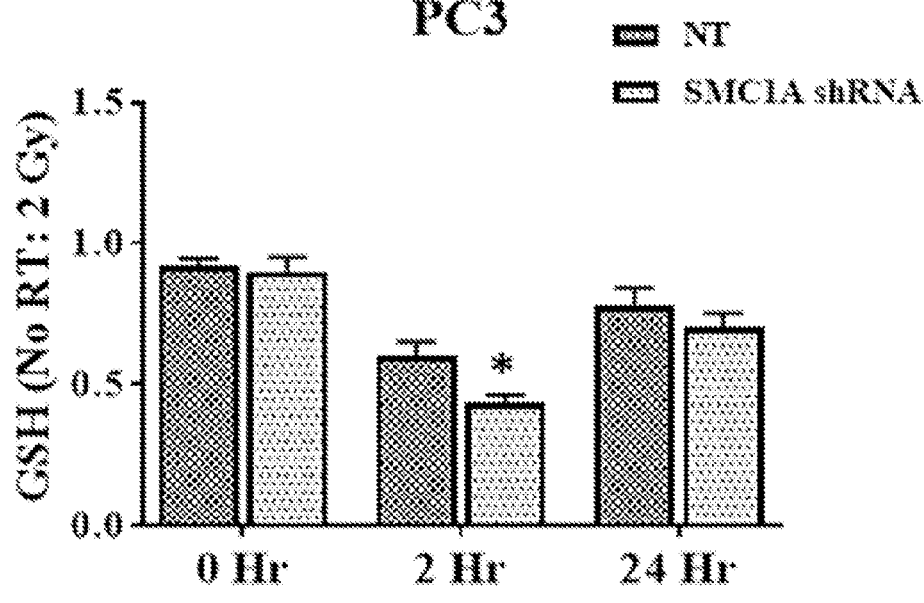
Figure 17F:
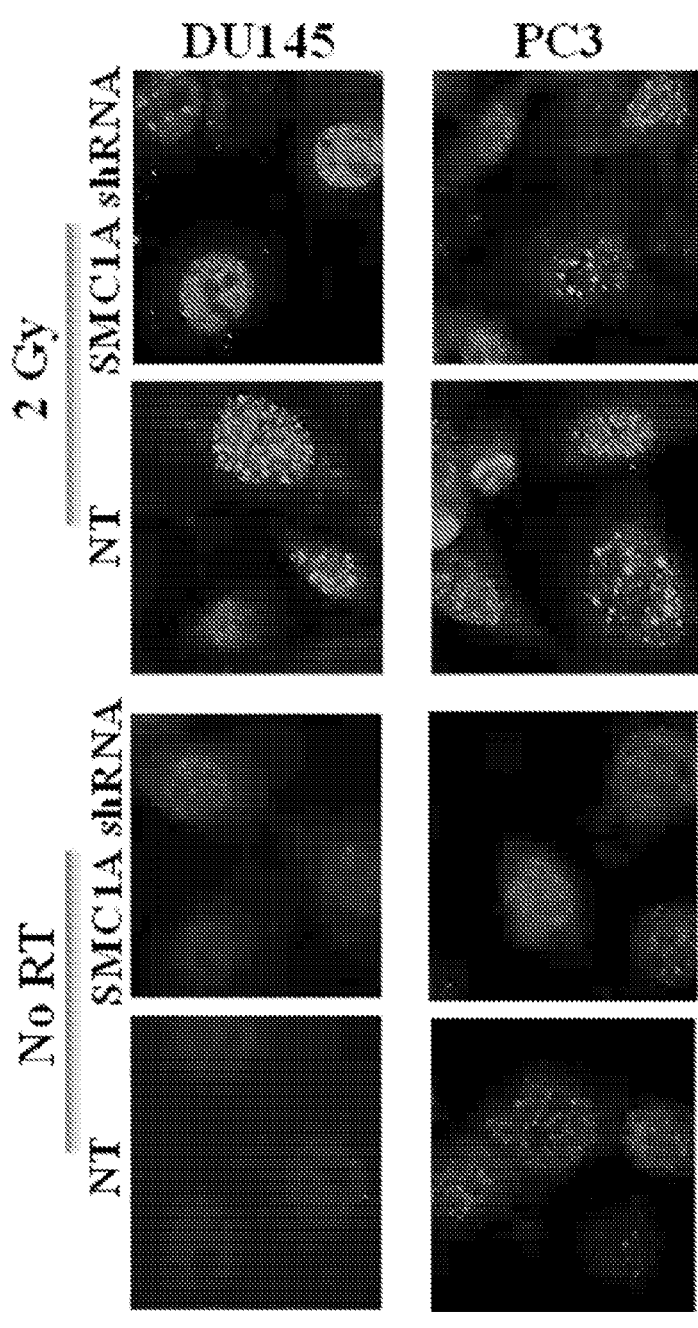
Figure 17G:
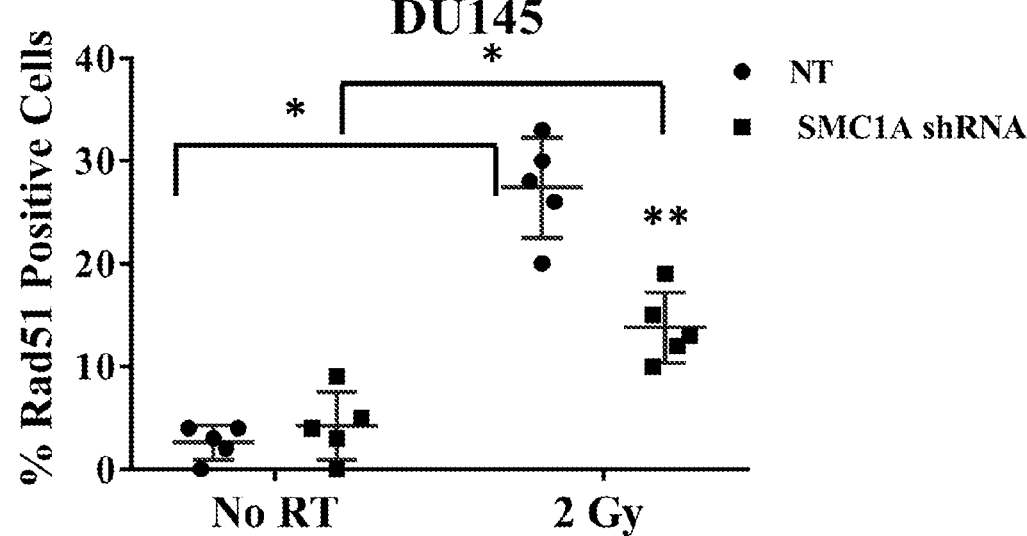
Figure 17H:
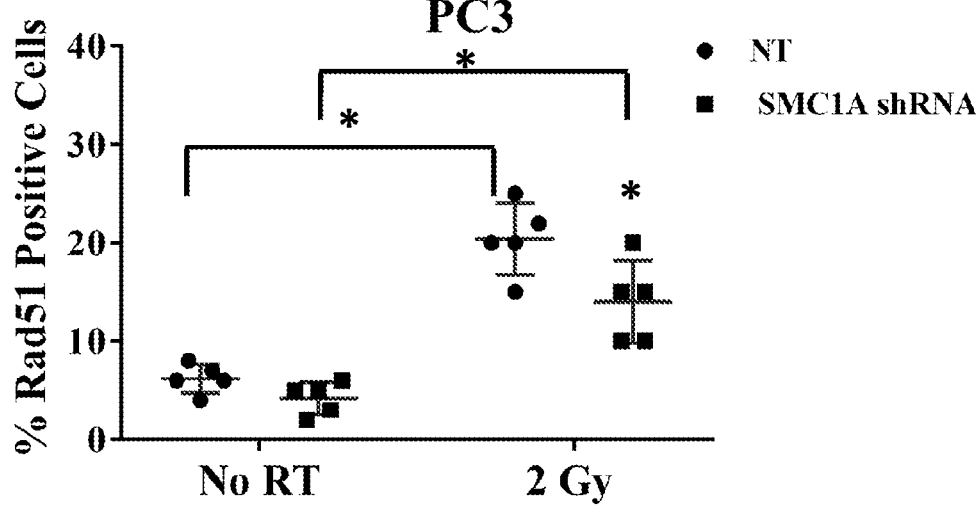

FIGS. 17A-17H show that SMC1A regulated DDR and oxidative stress in control and irradiated prostate cancer cells. FIG. 17A shows expression of proteins involved in homologous recombination (BRCA1, BRCA2, Rad51) and NHEJ (Ku70, Ku80) were tested in SMC1A shRNA expressing DU145 and PC3 cells by Western blot. The results showed that expression of Ku70 and Ku80, two regulatory subunit of NHEJ pathway was suppressed in SMC1A shRNA expressing DU145 and PC3 cells. Radiation activated both Ku70 and Ku80 in control cells but not in SMC1A shRNA expressing cells. SMC1A regulated the expression of Rad51 in control and x-irradiated cells. BRCA1 expression was activated in response to radiation in control cells but not in SMC1A shRNA expressing cells. BRCA2 expression was not significantly altered in control and irradiated cells. FIGS. 17B-17C show the effect of SMC1A suppression on ROS (DCF-DA) and cellular glutathione in control and x-irradiated DU145 and PC3 cells transduced with NT or SMC1A shRNA. The results showed that SMC1A shRNA expressing cells had significantly higher intracellular levels of ROS and reduced level of glutathione in x-irradiated cells. FIGS. 17D-17E are bar plots showing that Rad51 foci formation induced by x-irradiation was significantly higher in NT shRNA expressing cells compared to SMC1A shRNA expressing DU145 (FIG. 17D) and PC3 cells (FIG. 17E). FIG. 17F shows fluorescence microscopy pictures of control (no RT) and x-irradiated (2 Gy) DU145 and PC3 cells transduced with NT or SMC1A shRNA. FIGS. 17G-17H are plots showing the percentage of cells with persisting Rad51 foci, which was higher in NT shRNA compared to SMC1A shRNA expressing cells.

Figure 18A:
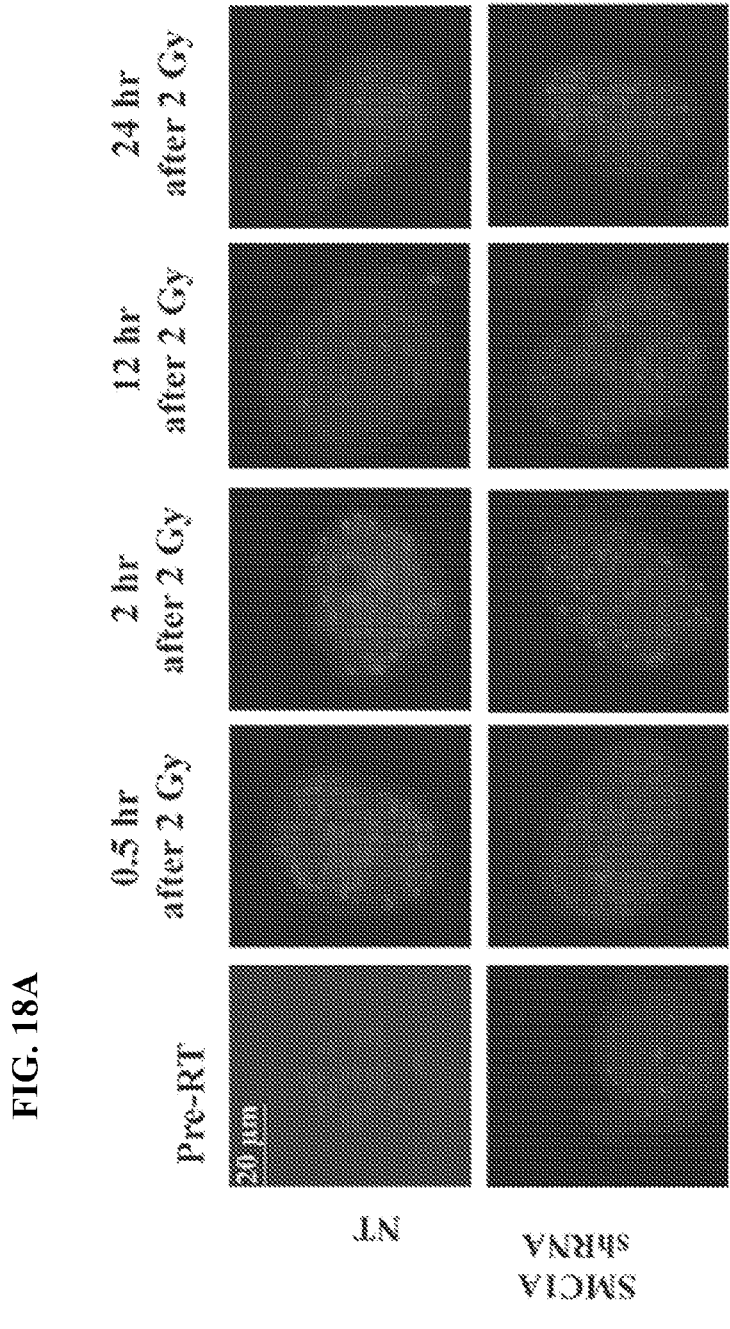
Figure 18B:
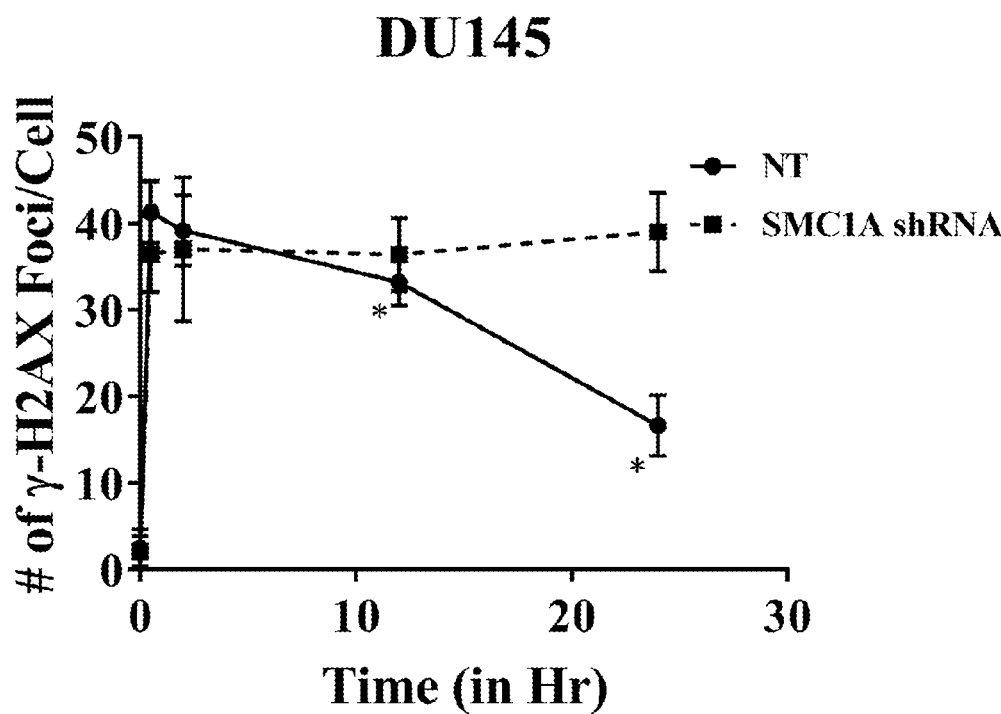
Figure 18C:
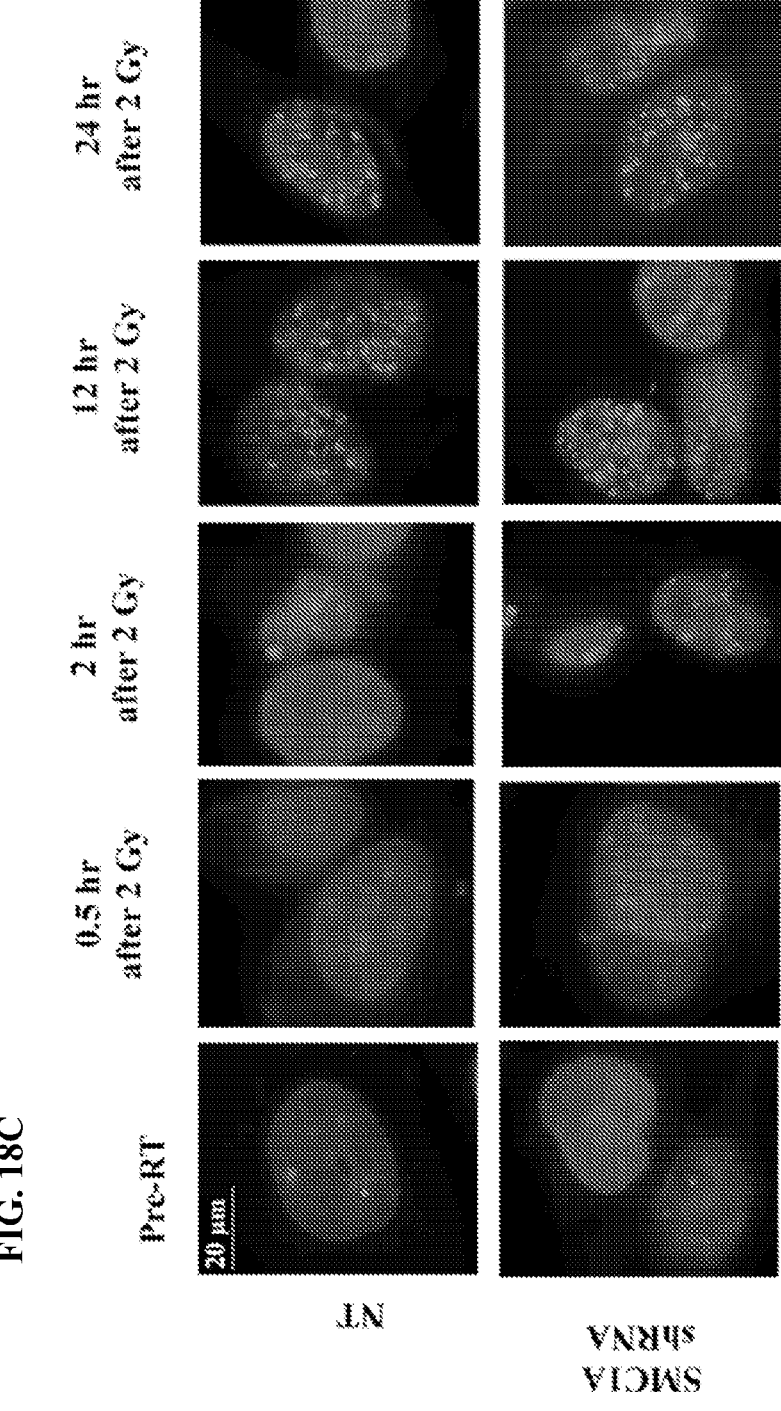
Figure 18D:
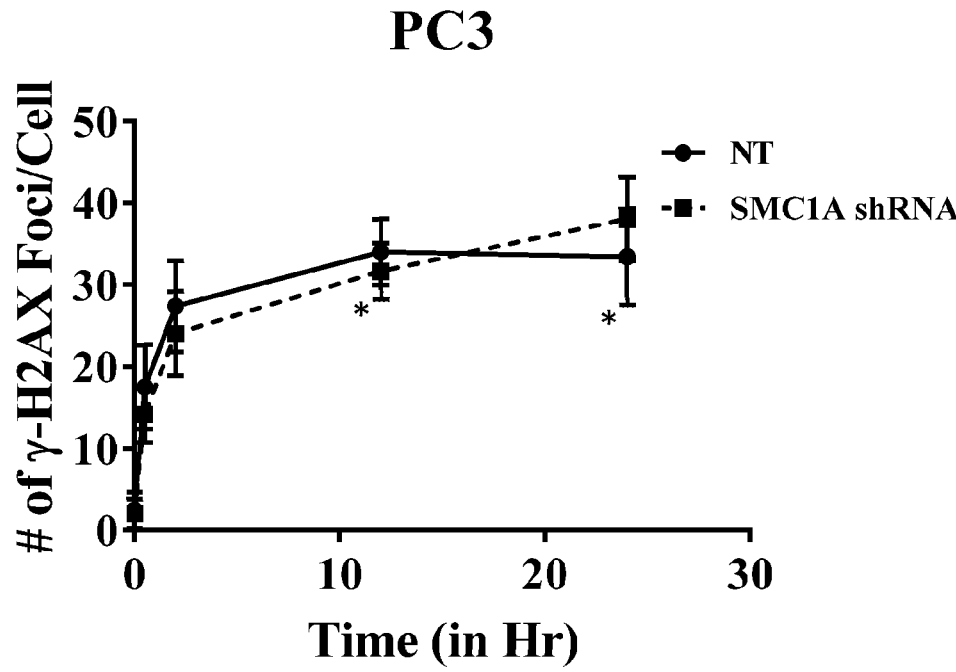

FIGS. 18A-18D show quantification of DNA DSB marker, γH2AX foci after irradiation in SMC1A shRNA expressing DU145 and PC3 cells. FIG. 18A shows representative images of γH2AX staining at the specific time points in NT and SMC1A-shRNA expressing DU145 cells after irradiation (2 Gy). Red fluorescence staining indicates positive while blue stain from DAPI indicates nuclei (magnification 40×). FIG. 18B is a graph showing the number of γH2AX foci in SMC1A shRNA expressing DU145 (Mean±SD, n=20). At 12 and 24 hr after radiation (asterisks), significant difference was found between SMC1A shRNA expressing DU145 cells. FIG. 18C shows representative images of γH2AX staining at the specific time points in NT and SMC1A-shRNA expressing PC3 cells after irradiation (2 Gy). Red fluorescence staining indicates positive while blue stain from DAPI indicates nuclei (magnification 40×). FIG. 18D is a graph showing the number of γH2AX foci in SMC1A shRNA expressing PC3 (Mean±SD, n=20). At 12 and 24 hr after radiation (asterisks), significant difference was found between SMC1A shRNA expressing DU145 cells. As it can be seen from FIGS. 18A-18D, the difference was more pronounced in DU145 cells compared to PC3 cells showing these cells are more radio-resistant. SMC1A suppression sensitized both DU145 and PC3 cells (P<0.05; SMC1A shRNA versus NT shRNA expressing DU145 and PC3 cells, no radiation treatment and irradiated with single dose of 2 Gy).

Figure 19A:
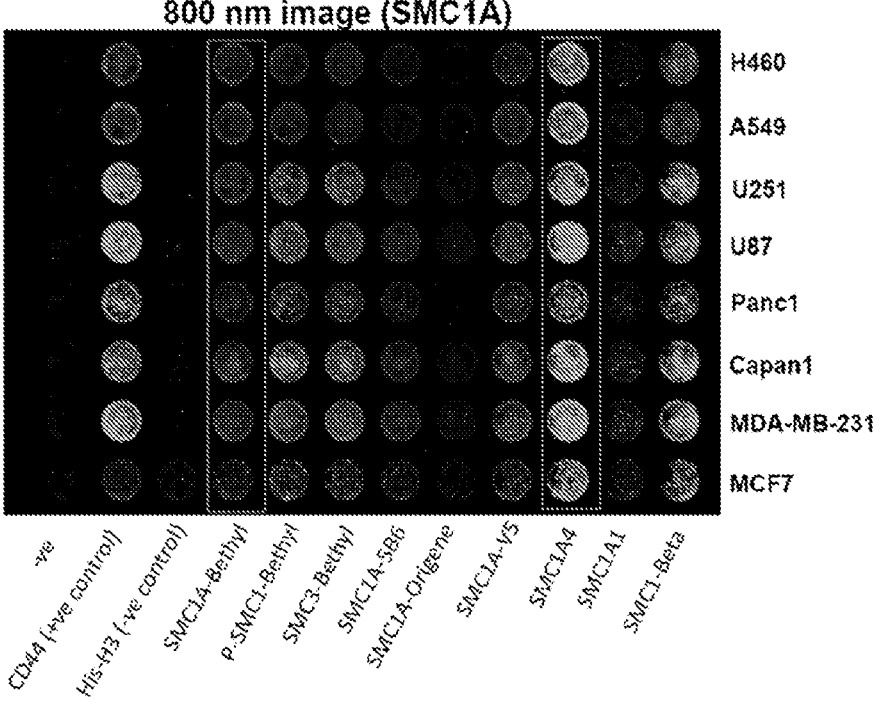
Figure 19B:
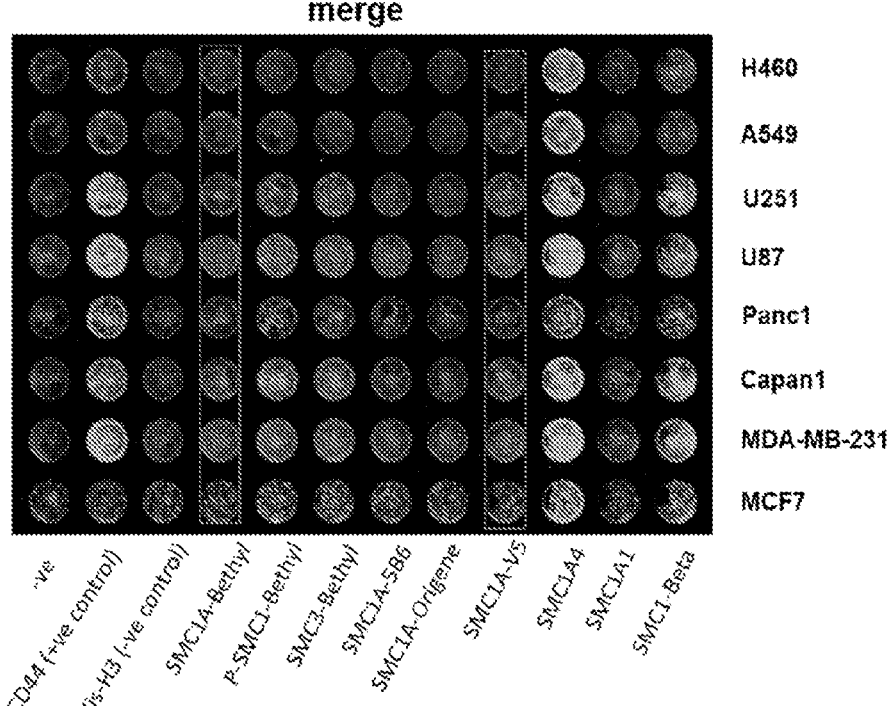
Figure 19C:
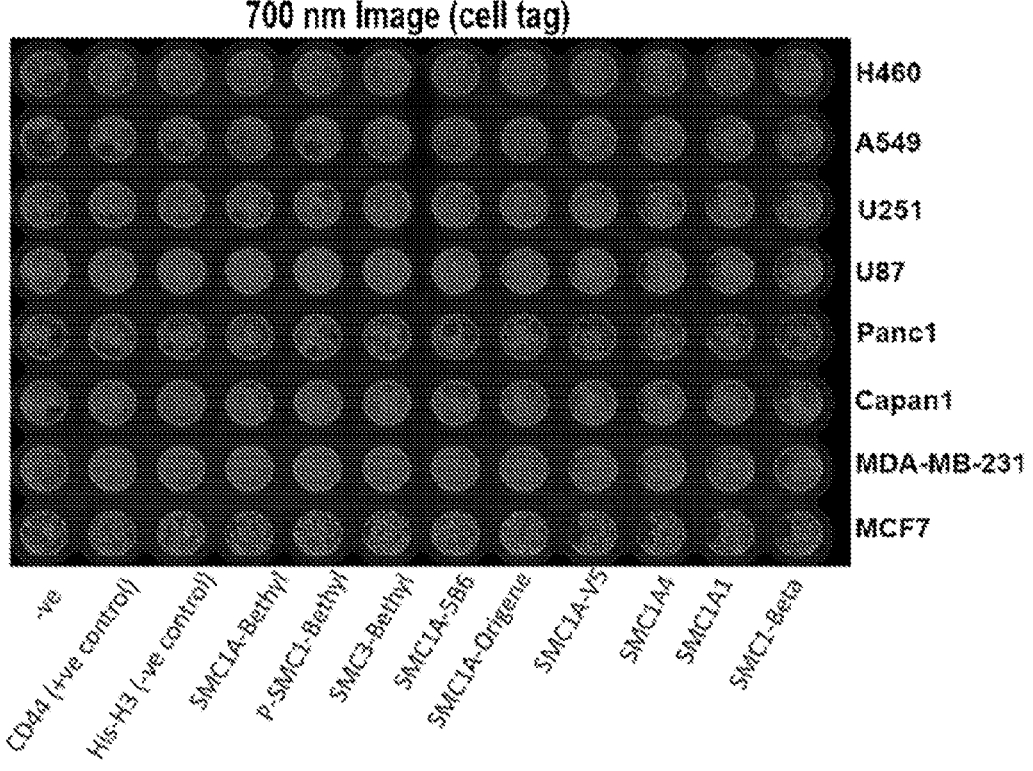

FIGS. 19A-19C show data for MS-1A: LI-COR® based cell surface (CSA) assay showed SMC1A expression at the tumor cell surface. Antibodies SMC1A-Origene and SMC1A-Bethyl are commercial SMC1A antibodies and show weaker binding relative to the antibodies provided herein including embodiments thereof (as shown SMC1A-V5, SMC1A4, SMC1A1, SMC1-Beta). Intensity of green fluorescence is the indicative of surface expression of SMC1A.

Figure 20A:
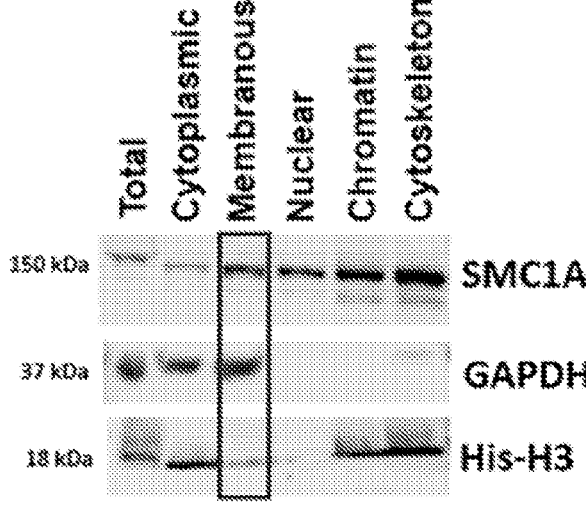
Figure 20B:
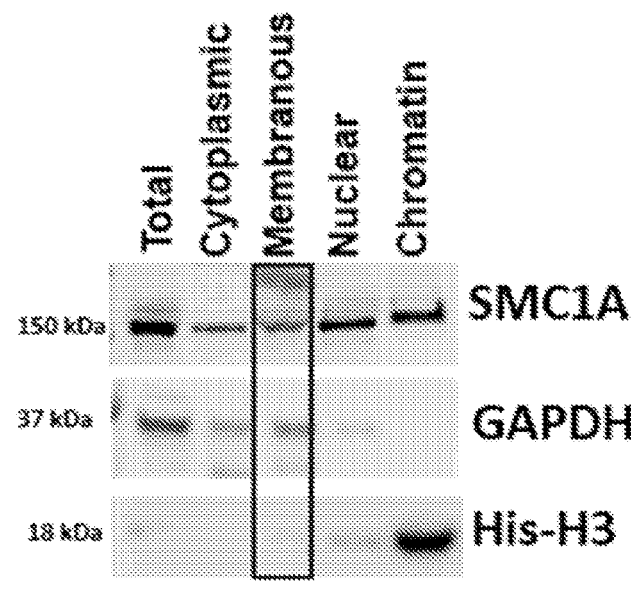
Figure 20C:
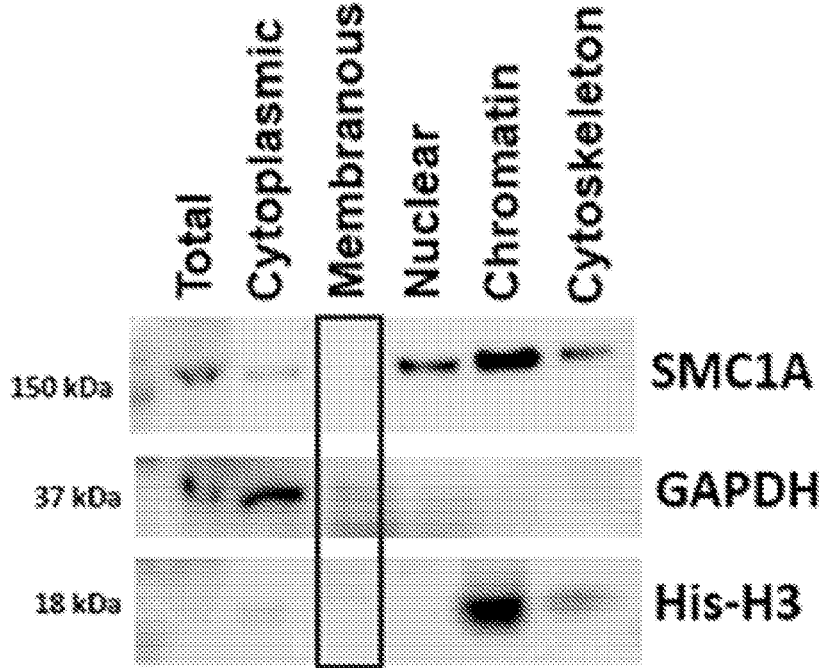

FIGS. 20A-20C show fractionation analysis isolated SMC1A in the membrane fraction of tumor cells.

Figure 21:
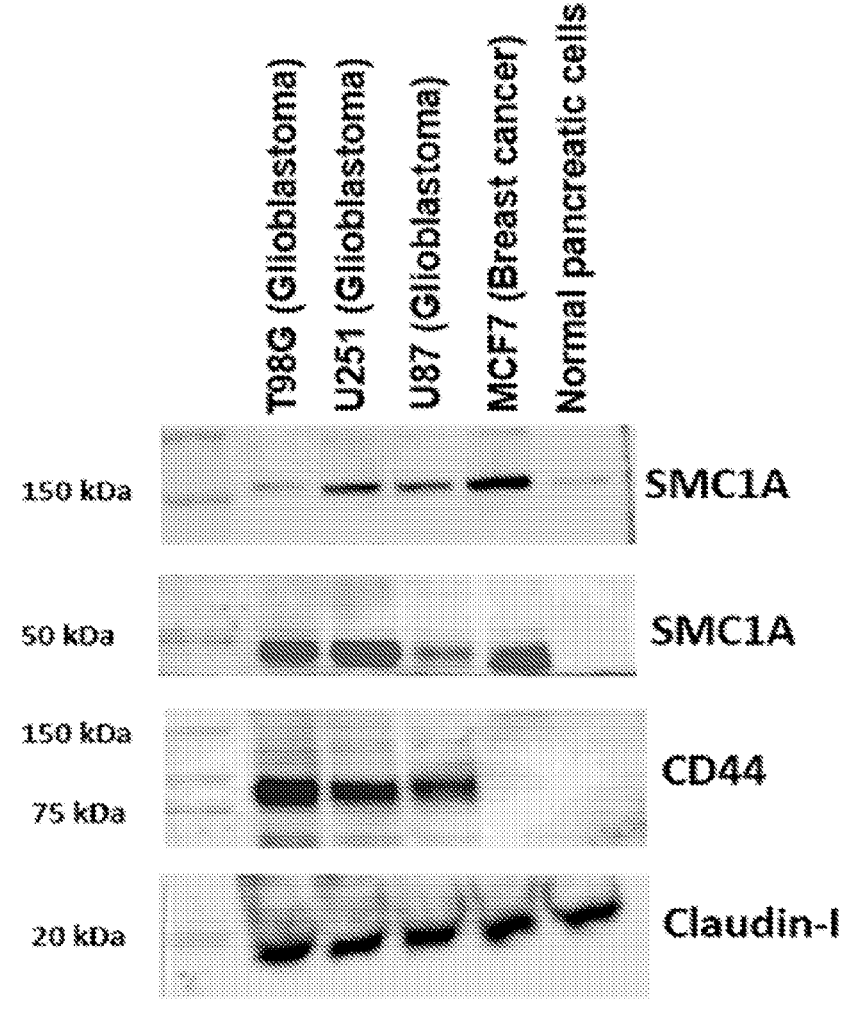

FIG. 21 shows biotinylation of cell surface proteins detected full-length SMC1A in the surface of tumor cells. A band at ~50 KDa reactive to SMC1A antibody was detected in the cancer cell lines but not in normal cell line. The intensity of bands in Western blot is indicative of the relative quantity of SMC1A on the cell surface.

Figure 22:
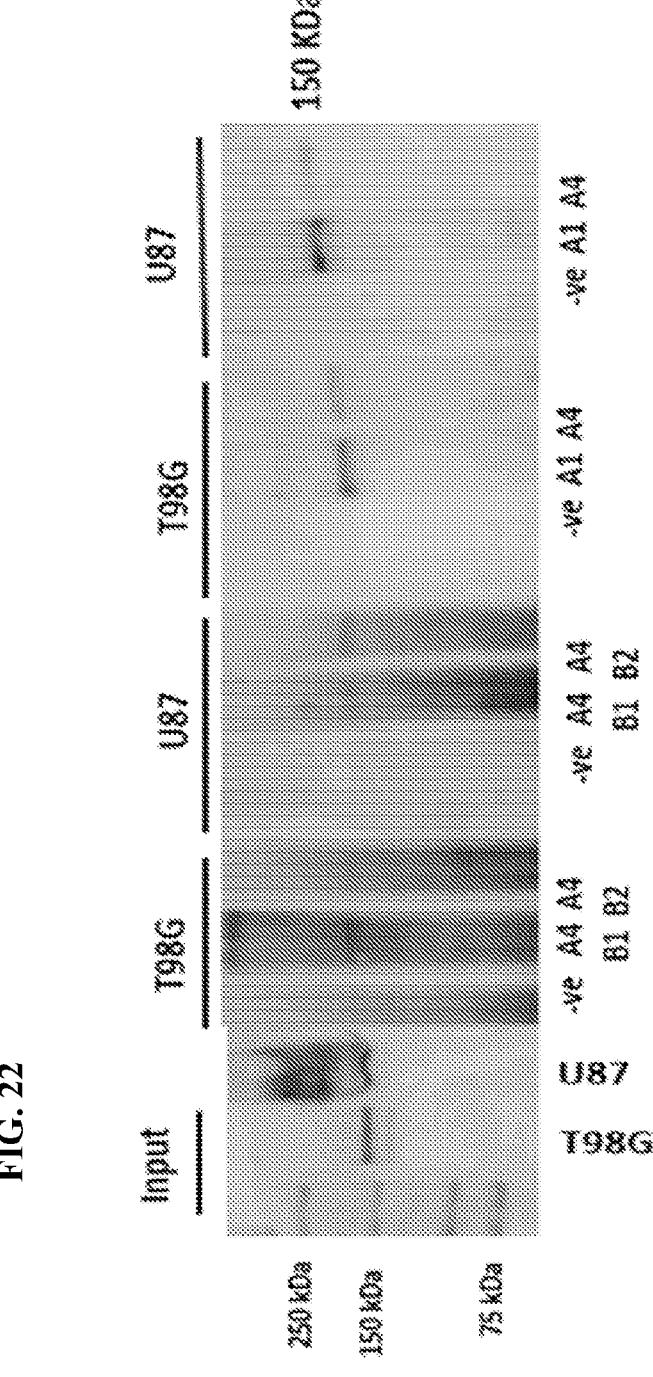

FIG. 22 shows immunoprecipitation with SMC1A chimeric antibodies showed specificities of the target-antibody interactions. Immunoprecipitation was performed using chimeric SMC1A4 and SMC1A1 mAbs respectively, and the Western blot with anti-human SMC1A polyclonal antibody (A300-055A) from Bethyl Labs (B1 and B2 are different batches of chimeric anti-SMC1A4.

Figure 23A:
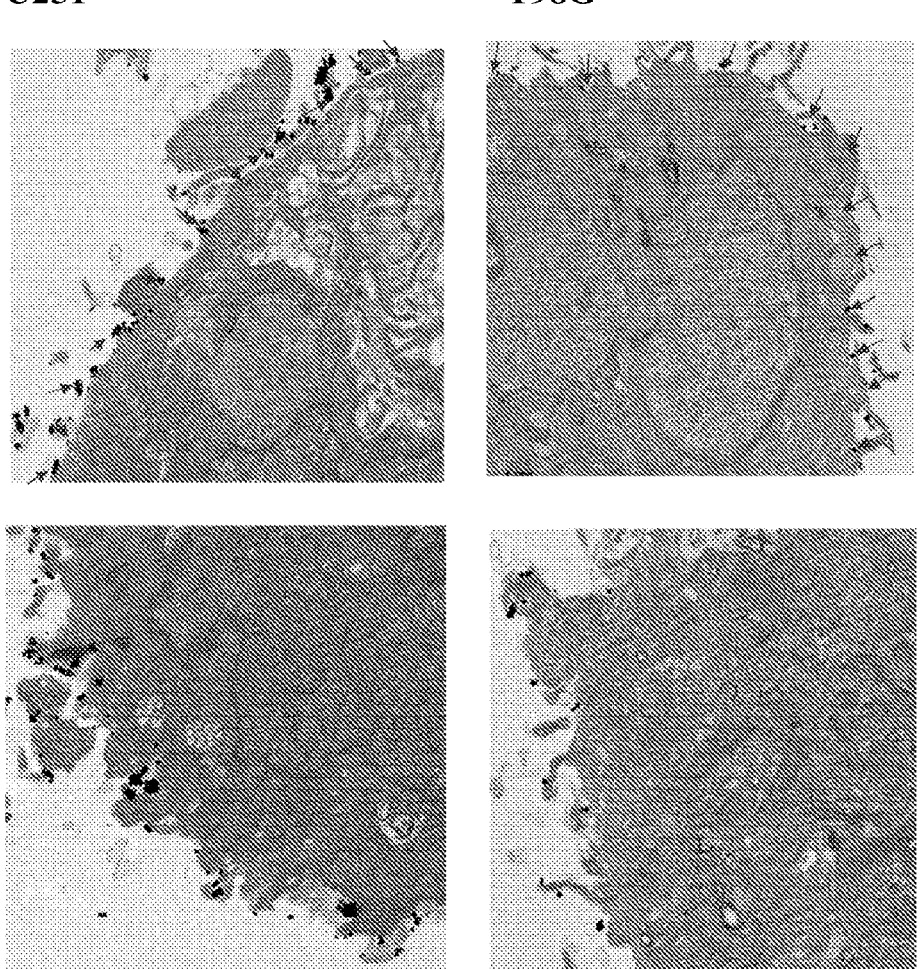
Figure 23B:
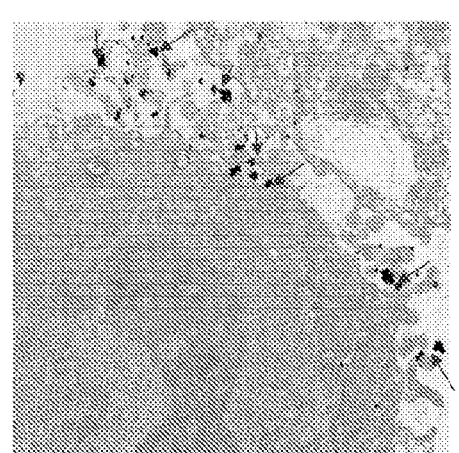
Figure 23B:
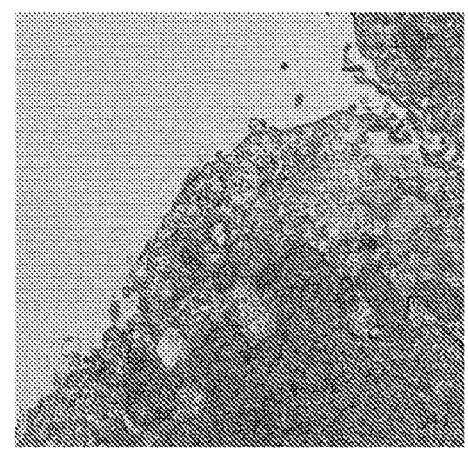
Figure 23B:
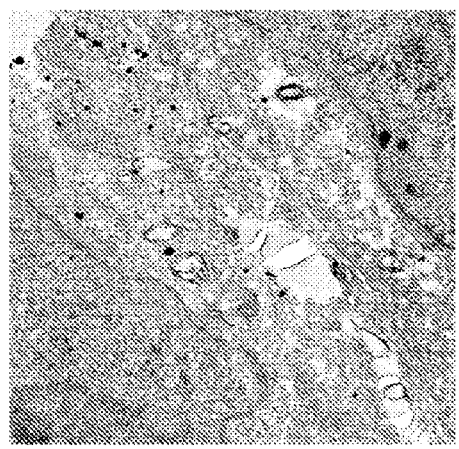
Figure 23B:
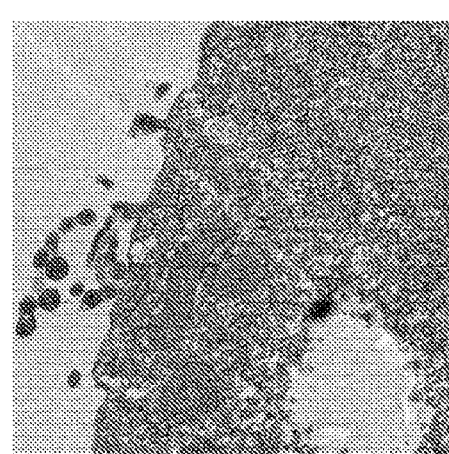

FIG. 23A-23B shows immunogold-EM captured SMC1A on tumor cell surface but not on normal cells. Immunogold EM was performed using anti-human SMC1A polyclonal antibody (A300-055A) from Bethyl Labs. Number of dots on the surface of each cell is indicative of relative quantity of SMC1A on the surface of cells.

Figure 24A:
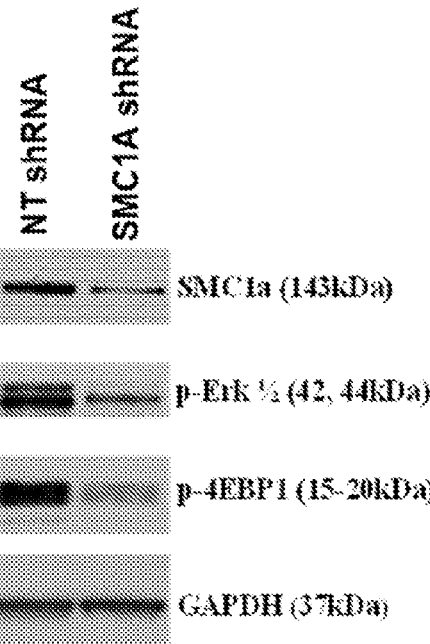
Figure 24B:
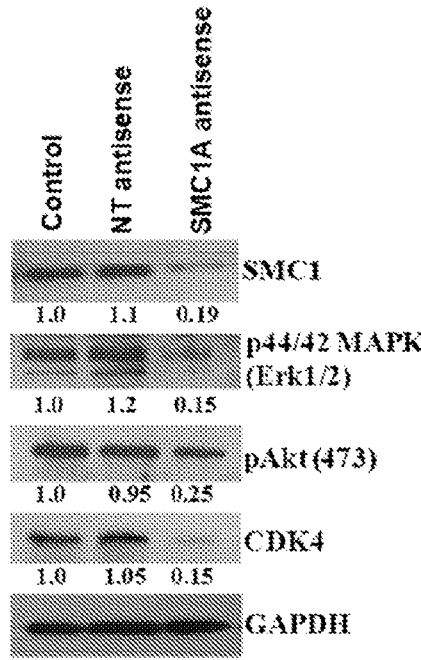
Figure 24C:
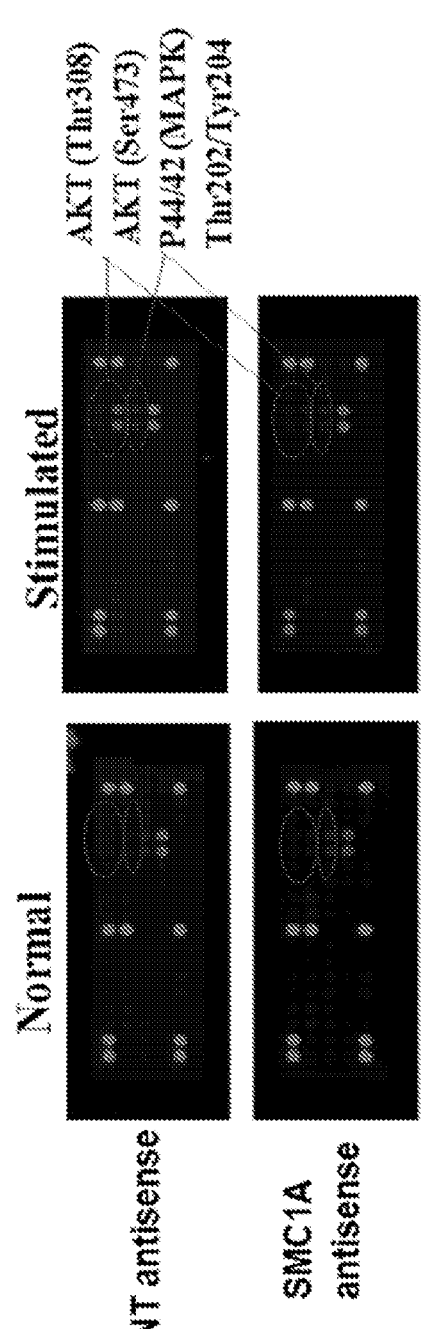

FIGS. 24A-24C shows evidence that SMC1 suppression alters the RTK signaling pathway in cancer cells. Suppression of SMC1A inhibits the phosphorylation of p44/42 MAPK (Erk1/2) and AKT as tested by Western blot and PathScan RTK signaling antibody array kit. FIG. 24A shows suppression of SMC1A by shRNA inhibits the MAPK and 4EBP1 activity in breast cancer (MDA-MB-231) cells. FIG. 24B shows MDA-MB-231 cells, control and transfected with SMC1A-antisense, treated with 50 ng/ml EGF for 5 min probed with SMC1A (Bethyl Labs) and western blot was performed on the cell lysates using p44/42 MAPK (Erk1/2), p-AKT,CDK4 and GAPDH antibodies (from Cell Signaling). FIG. 24C show MDA-MB-231 cells, control and transfected with SMC1A-antisense were treated with 50 ng/ml EGF for 5 min and PathScan RTK signaling antibody array kit following manufactures instructions (Abcam).

Figure 25A:
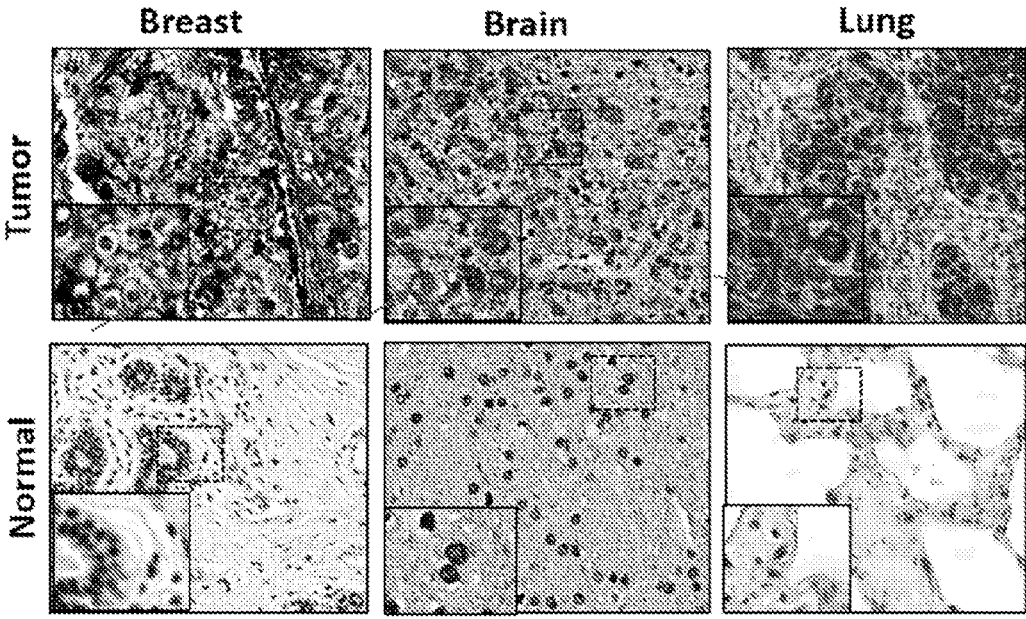
Figure 25B:
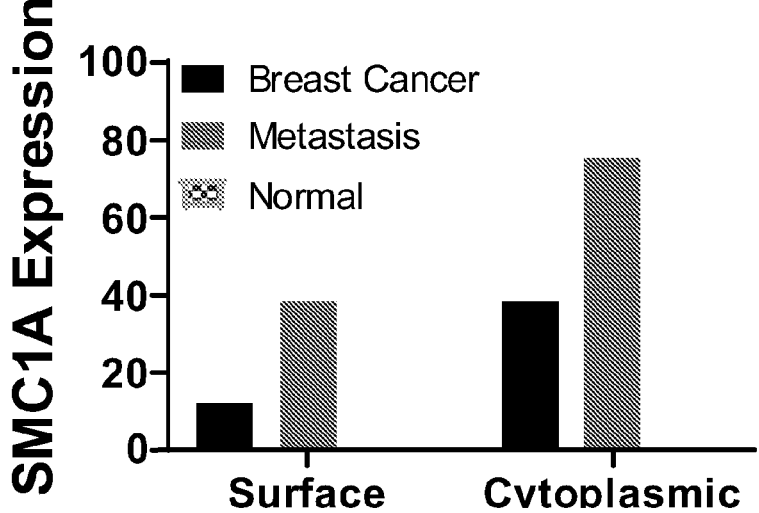
Figure 25C:
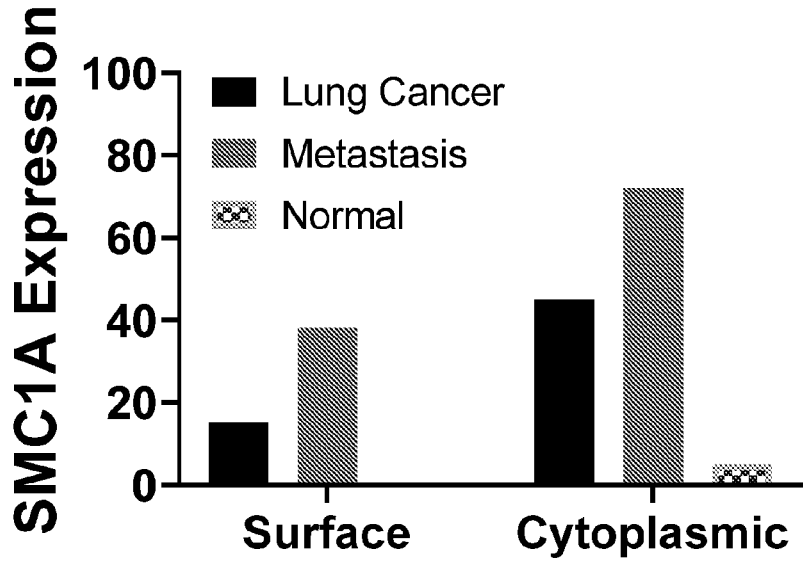
Figure 25D:
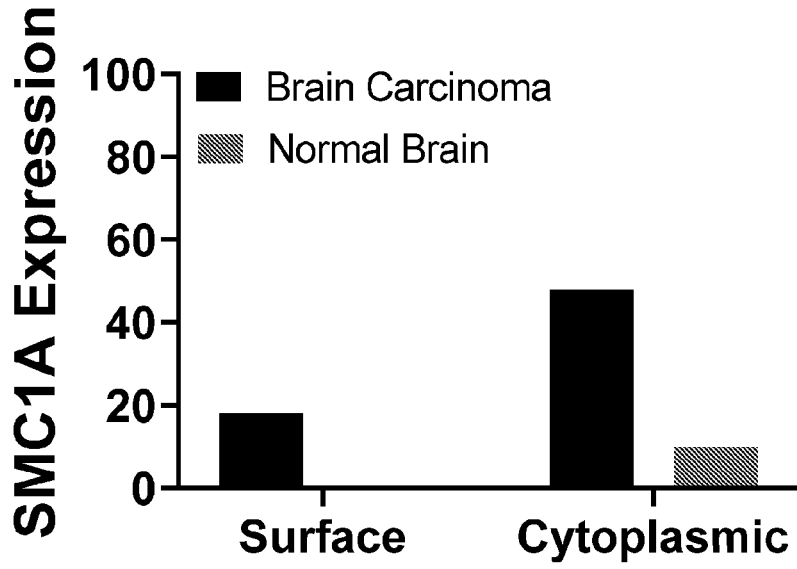
Figure 25E:
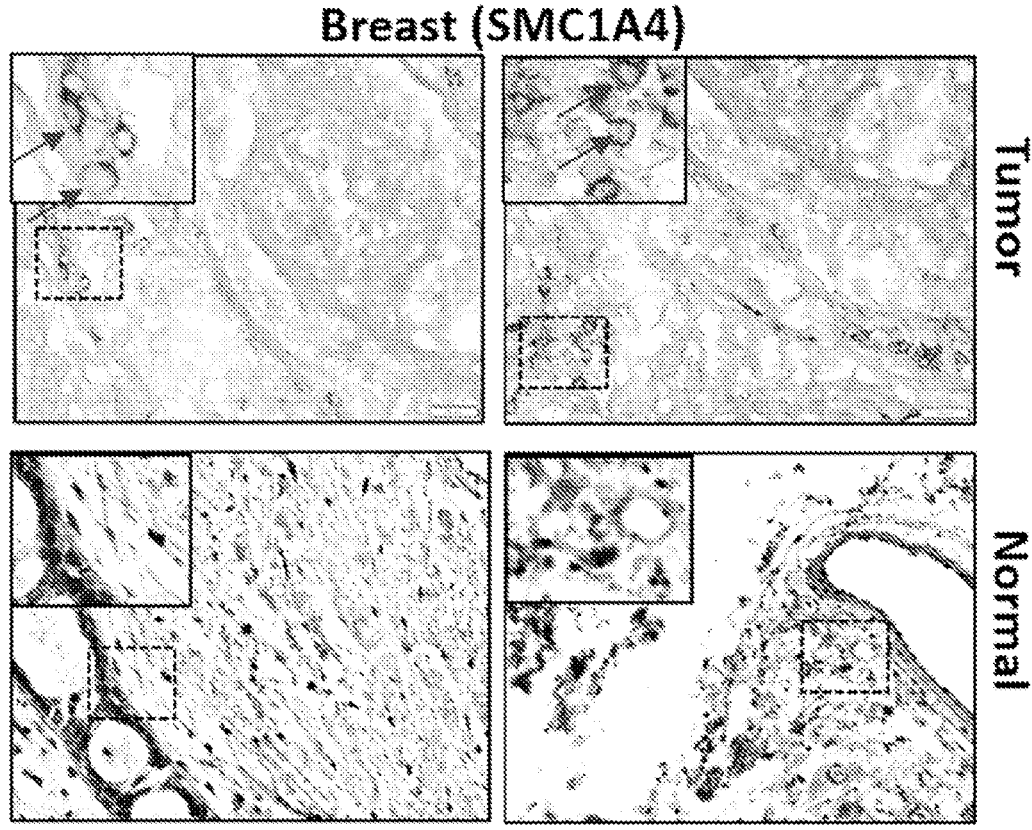

FIGS. 25A-25E present IHC showing membranous localization of SMC1A in tumor cells but nuclear expression in normal cells. FIG. 25A shows IHC was performed using SMC1A polyclonal antibody (A300-055A) from Bethyl Labs. FIGS. 25B-25D shows expression of SMC1A at the surface and cytoplasm of tumors and normal samples. All tumor and normal samples showed nuclear expression; FIG. 25E IHC was performed using SMC1A4 chimeric monoclonal antibody.

Figure 26:
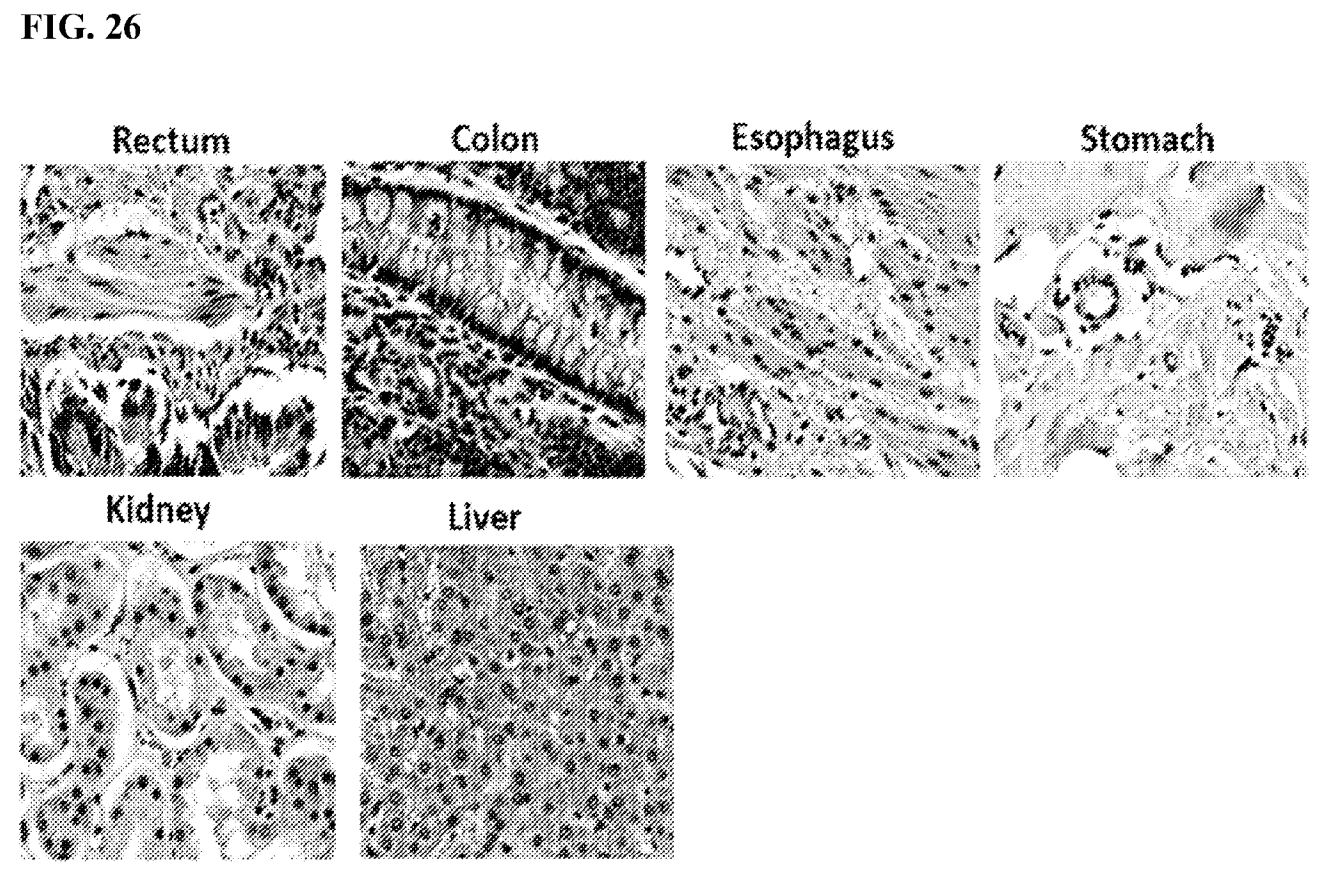

FIG. 26 presents IHC showing nuclear expression of SMC1A in normal tissues. IHC was performed on normal tissue sections using anti-human SMC1A polyclonal antibody (A300-055A) from Bethyl Labs.

DETAILED DESCRIPTION OF THE INVENTION

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

Definitions

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, NY 1989). Any methods, devices and materials similar or equivalent to those described herein can be used in the practice of this invention. The following definitions are provided to facilitate understanding of certain terms used frequently herein and are not meant to limit the scope of the present disclosure.

"Nucleic acid" refers to nucleotides (e.g., deoxyribonucleotides or ribonucleotides) and polymers thereof in either single-, double- or multiple-stranded form, or complements thereof; or nucleosides (e.g., deoxyribonucleosides or ribonucleosides). In embodiments, "nucleic acid" does not include nucleosides. The terms "polynucleotide," "oligonucleotide," "oligo" or the like refer, in the usual and customary sense, to a linear sequence of nucleotides. The term "nucleoside" refers, in the usual and customary sense, to a glycosylamine including a nucleobase and a five-carbon sugar (ribose or deoxyribose). Non limiting examples, of nucleosides include, cytidine, uridine, adenosine, guanosine, thymidine and inosine. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g. polynucleotides contemplated herein include any types of RNA, e.g. mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amio acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235, 033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

The term "complement," as used herein, refers to a nucleotide (e.g., RNA or DNA) or a sequence of nucleotides capable of base pairing with a complementary nucleotide or sequence of nucleotides. As described herein and commonly known in the art the complementary (matching) nucleotide of adenosine is thymidine and the complementary (matching) nucleotide of guanosine is cytosine. Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and a non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

As described herein the complementarity of sequences may be partial, in which only some of the nucleic acids match according to base pairing, or complete, where all the nucleic acids match according to base pairing. Thus, two sequences that are complementary to each other, may have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "peptidyl" and "peptidyl moiety" refers to a peptide attached to the remainder of a molecule. A peptidyl moiety may be substituted with a chemical linker that serves to attach the peptidyl moiety to a molecule. The peptidyl moiety may also be substituted with additional chemical moieties (e.g., additional R substituents). The term "meditope" as used herein refers to a peptidyl moiety included in the peptide compound as described herein. Thus, in embodiments, a meditope is a peptidyl moiety.

The peptidyl moiety (e.g., meditope) may be a linear or a cyclic peptide moiety. Various methods for cyclization of a peptide moiety may be used, e.g., to address in vivo stability and to enable chemo-selective control for subsequent conjugation chemistry. In some embodiments, the cyclization strategy is a lactam cyclization strategy, including head-to-tail (head-tail) lactam cyclization (between the terminal residues of the acyclic peptide) and/or lactam linkage between other residues. Lactam formation may also be affected by incorporating residues such as glycine, β-Ala, and/or 7-aminoheptanoic acid, and the like, into the acyclic peptide cyclization precursors to produce different lactam ring sizes and modes of connectivity. Additional cyclization strategies such as "click" chemistry and olefin metathesis also can be used. Such methods of peptide and peptidomimetic cyclization are well known in the art. In embodiments, the peptidyl moiety (e.g., meditope) is a linear peptidyl moiety (e.g., linear meditope). In embodiments, the peptidyl moiety (e.g., meditope) is a cyclic peptidyl moiety (e.g., cyclic meditope).

The term "peptide compound" refers to a compound including a peptidyl portion. In embodiments, the peptide compound includes a peptide or peptidyl moiety directly (covalently) or indirectly (non-covalently) attached to one or more chemical substituents. In embodiments, the peptide compound includes a peptidyl moiety. In embodiments, the peptide compound is a compound as described in WO 2013/055404 or WO 2019/028190. Thus, the complexes provided herein may include a non-covalent linker including a peptidyl moiety, wherein the peptidyl moiety is a meditope. In embodiments, the chemical linker is a non-covalent peptidyl linker including a meditope. In embodiments, the chemical linker is a covalent peptidyl linker including a meditope.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that may be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence. An amino acid residue in a protein "corresponds" to a given residue when it occupies the same essential structural position within the protein as the given residue. One skilled in the art will immediately recognize the identity and location of residues corresponding to a specific position in a protein (e.g., SMC1 antibody or anti-SMC1 antibody) in other proteins with different numbering systems. For example, by performing a simple sequence alignment with a protein (e.g., SMC1) the identity and location of residues corresponding to specific positions of the protein are identified in other protein sequences aligning to the protein. For example, a selected residue in a selected protein corresponds to glutamic acid at position 138 when the selected residue occupies the same essential spatial or other structural relationship as a glutamic acid at position 138. In some embodiments, where a selected protein is aligned for maximum homology with a protein, the position in the aligned selected protein aligning with glutamic acid 138 is the to correspond to glutamic acid 138. Instead of a primary sequence alignment, a three dimensional structural alignment can also be used, e.g., where the structure of the selected protein is aligned for maximum correspondence with the glutamic acid at position 138, and the overall structures compared. In this case, an amino acid that occupies the same essential position as glutamic acid 138 in the structural model is the residue to correspond to the glutamic acid 138 residue.

Likewise, a selected residue in a selected antibody (or Fab domain) corresponds to light chain threonine at Kabat position 40, when the selected residue occupies the same essential spatial or other structural relationship as a light chain threonine at Kabat position 40. In some embodiments, where a selected protein is aligned for maximum homology with the light chain of an antibody (or Fab domain), the position in the aligned selected protein aligning with threonine 40 is said to correspond to threonine 40. Instead of a primary sequence alignment, a three dimensional structural alignment can also be used, e.g., where the structure of the selected protein is aligned for maximum correspondence with the light chain threonine at Kabat position 40, and the overall structures compared. In this case, an amino acid that occupies the same essential position as threonine 40 in the structural model is said to correspond to the threonine 40 residue.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci.* USA 85:2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

Antibodies are large, complex molecules (molecular weight of ~150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region, involved in binding the target antigen, and a constant ("C") region that interacts with other components of the immune system. The light and heavy chain variable regions include domains (also referred to herein as light chain variable (VL) domain and heavy chain variable (VH) domain, respectively) that come together in 3-dimensional space to form a variable region that binds the antigen (for example, a receptor on the surface of a cell). Within each light or heavy chain variable domain, there are three short segments (averaging 10 amino acids in length) called the complementarity determining regions ("CDRs"). The six CDRs in an antibody variable region (three from the light chain and three from the heavy chain) fold up together in 3-dimensional space to form the actual antibody binding site which docks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs.

An "antibody variant" as provided herein refers to a polypeptide capable of binding to an antigen and including one or more structural domains of an antibody or fragment thereof. Non-limiting examples of antibody variants include single-domain antibodies or nanobodies, affibodies (polypeptides smaller than monoclonal antibodies (e.g., about 6 kDA) and capable of binding antigens with high affinity and imitating monoclonal antibodies, monospecific Fab₂, bispecific Fab₂, trispecific Fab₃, monovalent IgGs, scFv, bispecific diabodies, trispecific triabodies, scFv-Fc, minibodies, IgNAR, V-NAR, hcIgG, VhH, or peptibodies. A "nanobody" or "single domain antibody" as described herein is commonly well known in the art and refers to an antibody fragment consisting of a single monomeric variable antibody domain. Like a whole antibody, it is able to bind selectively to a specific antigen. A "peptibody" as provided herein refers to a peptide moiety attached (through a covalent or non-covalent linker) to the Fc domain of an antibody. Further non-limiting examples of antibody variants known in the art include antibodies produced by cartilaginous fish or camelids. A general description of antibodies from camelids and the variable regions thereof and methods for their production, isolation, and use may be found in references WO97/49805 and WO 97/49805, which are incorporated, by reference herein in their entirety and for all purposes. Likewise, antibodies from cartilaginous fish and the variable regions thereof and methods for their production, isolation, and use may be found in WO2005/118629, which is incorporated by reference herein in its entirety and for all purposes.

The terms "CDR L1", "CDR L2" and "CDR L3" as provided herein refer to the complementarity determining regions (CDR) 1, 2, and 3 of the variable light (L) chain of an antibody. In embodiments, the variable light chain provided herein includes in N-terminal to C-terminal direction a CDR L1, a CDR L2 and a CDR L3. Likewise, the terms "CDR H1", "CDR H2" and "CDR H3" as provided herein refer to the complementarity determining regions (CDR) 1, 2, and 3 of the variable heavy (H) chain of an antibody. In embodiments, the variable heavy chain provided herein includes in N-terminal to C-terminal direction a CDR H1, a CDR H2 and a CDR H3. In embodiments, the CDRs of the light chain are referred to as CDR1, CDR2, and CDR3 of VL and the CDRs of the heavy chain are referred to as CDR1, CDR2, and CDR3 of VH. See, for example the tables as provided herein.

The terms "FR L1", "FR L2", "FR L3" and "FR L4" as provided herein are used according to their common meaning in the art and refer to the framework regions (FR) 1, 2, 3 and 4 of the variable light (L) chain of an antibody. In embodiments, the variable light chain provided herein includes in N-terminal to C-terminal direction a FR L1, a FR L2, a FR L3 and a FR L4. Likewise, the terms "FR H1", "FR H2", "FR H3" and "FR H4" as provided herein are used according to their common meaning in the art and refer to the framework regions (FR) 1, 2, 3 and 4 of the variable heavy (H) chain of an antibody. In embodiments, the variable heavy chain provided herein includes in N-terminal to C-terminal direction a FR H1, a FR H2, a FR H3 and a FR H4.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL), variable light chain (VL) domain or light chain variable domain and variable heavy chain (VH), variable heavy chain (VH) domain or heavy chain variable domain refer to these light and heavy chain regions, respectively. The terms variable light chain (VL), variable light chain (VL) domain and light chain variable domain as referred to herein may be used interchangeably. The terms variable heavy chain (VH), variable heavy chain (VH) domain and heavy chain variable domain as referred to herein may be used interchangeably. The Fc (i.e. fragment crystallizable region) is the "base" or "tail" of an immunoglobulin and is typically composed of two heavy chains that contribute two or three constant domains depending on the class of the antibody. By binding to specific proteins, the Fc region ensures that each antibody generates an appropriate immune response for a given antigen. The Fc region also binds to various cell receptors, such as Fc receptors, and other immune molecules, such as complement proteins.

The term "antibody" is used according to its commonly known meaning in the art. Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H-C_{H1}$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

For preparation of monoclonal or polyclonal antibodies, any technique known in the art can be used (see, e.g., Kohler & Milstein, Nature 256:495-497 (1975); Kozbor et al., Immunology Today 4:72 (1983); Cole et al., pp. 77-96 in Monoclonal Antibodies and Cancer Therapy (1985)). "Monoclonal" antibodies (mAb) refer to antibodies derived from a single clone. Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., Nature 348: 552-554 (1990); Marks et al., Biotechnology 10:779-783 (1992)).

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL), variable light chain (VL) domain or light chain variable region and variable heavy chain (VH), variable heavy chain (VH) domain or heavy chain variable region refer to these light and heavy chain regions, respectively. The terms variable light chain (VL), variable light chain (VL) domain and light chain variable region as referred to herein may be used interchangeably. The terms variable heavy chain (VH), variable heavy chain (VH) domain and heavy chain variable region as referred to herein may be used interchangeably. The Fc (i.e. fragment crystallizable region; also referred to herein as "Fc domain") is the "base" or "tail" of an immunoglobulin and is typically composed of two heavy chains that contribute two or three constant domains depending on the class of the antibody. By binding to specific proteins, the Fc region ensures that each antibody generates an appropriate immune response for a given antigen. The Fc region also binds to various cell receptors, such as Fc receptors, and other immune molecules, such as complement proteins. In embodiments, the Fc region includes a constant heavy chain domain 3 (CH3 domain) and a constant heavy chain domain 2 (CH2 domain).

The epitope of an antibody is the region of its antigen to which the antibody binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 30% but preferably 50%, 75%, 90% or even 99% as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

The term "antigen" as provided herein refers to molecules capable of binding to the antibody binding domain provided herein. An "antigen binding domain" as provided herein is a region of an antibody that binds to an antigen (epitope). As described above, the antigen binding domain is generally composed of one constant and one variable domain of each of the heavy and the light chain (VL, VH, CL and CH1, respectively). The paratope or antigen-binding site is formed on the N-terminus of the antigen binding domain. The two variable domains of an antigen binding domain typically bind the epitope on an antigen.

A single-chain variable fragment (scFv) is typically a fusion protein of the variable regions of the heavy (VH) and light chains (VL) of immunoglobulins, connected with a short linker peptide of 10 to about 25 amino acids. The linker may usually be rich in glycine for flexibility, as well as serine or threonine for solubility. The linker can either connect the N-terminus of the VH with the C-terminus of the VL, or vice versa. In embodiments, the linker includes more than one serine. In embodiments, the linker includes more than one glycine. In embodiments, the linker has the structure of -(Gly-Gly-Gly-Gly-Ser)$_3$-.

For preparation of suitable antibodies of the invention and for use according to the invention, e.g., recombinant, mono-clonal, or polyclonal antibodies, many techniques known in the art can be used (see, e.g., Kohler & Milstein, Nature 256:495-497 (1975); Kozbor et al., Immunology Today 4:72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676, 980, WO 91/00360; WO 92/200373; and EP 03089).

Methods for humanizing or primatizing non-human antibodies are well known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) Nature 321:522; and Verhoyen et al. (1988) Science 239:1534). Humanized antibodies are further described in, e.g., Winter and Milstein (1991) Nature 349:293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immunol., 44:65-92 (1988), Verhoeyen et al., Science 239:1534-1536 (1988) and Presta, Curr. Op. Struct. Biol. 2:593-596 (1992), Padlan, Molec. Immun., 28:489-498 (1991); Padlan, Molec. Immun., 31(3):169-217 (1994)), by substituting rodent CDRs or CDR sequences for the corresponding sequences of a human antibody. Accordingly, such humanized antibodies are chimeric antibodies (U.S. Pat. No. 4,816, 567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

A "ligand" refers to an agent, e.g., a polypeptide or other molecule, capable of binding to a receptor or antibody, antibody variant, antibody region or fragment thereof.

Techniques for conjugating therapeutic agents to antibodies are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)). As used herein, the term "antibody-drug conjugate" or "ADC" refers to a therapeutic agent conjugated or otherwise covalently bound to to an antibody.

For specific proteins described herein, the named protein includes any of the protein's naturally occurring forms, variants or homologs that maintain the protein transcription factor activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference, homolog or functional fragment thereof.

The term "SMC1" or "SMC1 protein" as used herein refers to any recombinant or naturally-occurring forms of Structural Maintenance of Chromosome-1 (SMC1) or variants, isoforms (e.g., SMC1A, SMC1B) or homologs thereof that maintain SMC1 activity (e.g. within at least 50%, 80%, 90%, 95%, 96%, 97%, 98%, 99% or 100% activity compared to SMC1). In some aspects, the variants, isoforms or homologs have at least 90%, 95%, 96%, 97%, 98%, 99% or 100% amino acid sequence identity across the whole sequence or a portion of the sequence (e.g. a 10, 20, 50, 100, 150 or 200 continuous amino acid portion) compared to a naturally occurring SMC1 polypeptide. In embodiments, SMC1 is substantially identical to the protein identified by the NCBI reference number NP_006297 or a variant, isoform or homolog having substantial identity thereto. In embodiments, SMC1 is substantially identical to the protein identified by the NCBI reference number NP_683515 or a variant, isoform or homolog having substantial identity thereto. In embodiments, SMC1 is substantially identical to the protein identified by the NCBI reference number NP_006297.2 or a variant, isoform or homolog having substantial identity thereto. In embodiments, SMC1 is substantially identical to the protein identified by the NCBI reference number NP_001268392 or a variant, isoform or homolog having substantial identity thereto. In embodiments, SMC1 is substantially identical to the protein identified by the NCBI reference number NP_062684 or a variant, isoform or homolog having substantial identity thereto. In embodiments, SMC1 is substantially identical to the protein identified by the UniProt reference number Q14683 or a variant, isoform or homolog having substantial identity thereto. In embodiments, SMC1 is substantially identical to the protein identified by the UniProt reference number Q9CU62 or a variant, isoform or homolog having substantial identity thereto. In embodiments, SMC1 is substantially identical to the protein identified by the UniProt reference number Q68EN4 or a variant, isoform or homolog having substantial identity thereto. In embodiments, the SMC1 protein is SMC1A or a variant, isoform or homolog thereof. In further embodiments, SMC1A is substantially identical to the protein identified by the NCBI reference number NP_006297 or a variant, isoform or homolog having substantial identity thereto. In embodiments, the SMC1 protein is SMC1-beta or a variant, isoform or homolog thereof. In further embodiments, SMC1B is substantially identical to the protein identified by the NCBI reference number NP_683515 or a variant, isoform or homolog having substantial identity thereto.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The terms "plasmid", "vector" or "expression vector" refer to a nucleic acid molecule that encodes for genes and/or regulatory elements necessary for the expression of genes. Expression of a gene from a plasmid can occur in cis or in trans. If a gene is expressed in cis, the gene and the regulatory elements are encoded by the same plasmid. Expression in trans refers to the instance where the gene and the regulatory elements are encoded by separate plasmids.

The terms "transfection", "transduction", "transfecting" or "transducing" can be used interchangeably and are defined as a process of introducing a nucleic acid molecule or a protein to a cell. Nucleic acids are introduced to a cell using non-viral or viral-based methods. The nucleic acid molecules may be gene sequences encoding complete proteins or functional portions thereof. Non-viral methods of transfection include any appropriate transfection method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. In some embodiments, the nucleic acid molecules are introduced into a cell using electroporation following standard procedures well known in the art. For viral-based methods of transfection any useful viral vector may be used in the methods described herein. Examples for viral vectors include, but are not limited to retroviral, adenoviral, lentiviral and adeno-associated viral vectors. In some embodiments, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) *Gene Therapy* 8:1-4 and Prochiantz (2007) *Nat. Methods* 4:119-20.

A "label" or a "detectable moiety" is a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

When the label or detectable moiety is a radioactive metal or paramagnetic ion, the agent may be reacted with another long-tailed reagent having a long tail with one or more chelating groups attached to the long tail for binding to these ions. The long tail may be a polymer such as a polylysine, polysaccharide, or other derivatized or derivatizable chain having pendant groups to which the metals or ions may be added for binding. Examples of chelating groups that may be used according to the disclosure include, but are not limited to, ethylenediaminetetraacetic acid (EDTA), diethylenetriaminepentaacetic acid (DTPA), DOTA, NOTA, NETA, TETA, porphyrins, polyamines, crown ethers, bis-thiosemicarbazones, polyoximes, and like groups. The chelate is normally linked to the PSMA antibody or functional antibody fragment by a group, which enables the formation of a bond to the molecule with minimal loss of immunoreactivity and minimal aggregation and/or internal cross-linking. The same chelates, when complexed with non-radioactive metals, such as manganese, iron and gadolinium are useful for MRI, when used along with the antibodies and carriers described herein. Macrocyclic chelates such as NOTA, DOTA, and TETA are of use with a variety of metals and radiometals including, but not limited to, radionuclides of gallium, yttrium and copper, respectively. Other ring-type chelates such as macrocyclic polyethers, which are of interest for stably binding nuclides, such as $^{223}$Ra for RAIT may be used. In certain embodiments, chelating moieties may be used to attach a PET imaging agent, such as an Al—$^{18}$F complex, to a targeting molecule for use in PET analysis.

"Contacting" is used in accordance with its plain ordinary meaning and refers to the process of allowing at least two distinct species (e.g. antibodies and antigens) to become sufficiently proximal to react, interact, or physically touch. It should be appreciated; however, that the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a pharmaceutical composition as provided herein and a cell. In embodiments contacting includes, for example, allowing a pharmaceutical composition as described herein to interact with a cell.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include, but are not limited to, yeast cells and cells derived from plants and animals, for example mammalian, insect (e.g., *spodoptera*) and human cells.

A "stem cell" as provided herein refers to a cell characterized by the ability of self-renewal through mitotic cell division and the potential to differentiate into a tissue or an organ. Among mammalian stem cells, embryonic stem cells (ES cells) and somatic stem cells (e.g., HSC) can be distinguished. Embryonic stem cells reside in the blastocyst and give rise to embryonic tissues, whereas somatic stem cells reside in adult tissues for the purpose of tissue regeneration and repair. In embodiments, the stem cell is a leukemia stem cell (LSC). A "leukemia stem cell or "LSC" as provided herein refers to a cell capable of initiating the disease (leukemia) when transplanted into immunodeficient animals and can self-renew by giving rise to leukemia in serial transplantations and also partially differentiate into non-LSC bulk blasts that resemble the original disease but are unable to self-renew. An LSC may carry a gene mutation and be able to self-renew through mitotic cell division and differentiate into the hematopoietic lineage carrying said gene mutant or an LSC may remain as immature progenitor cells, also known as blast cells. In embodiments, the LSC expresses CD34.

The term "CD34" as referred to herein includes any of the recombinant or naturally-occurring forms of the cluster of differentiation 34 protein, or variants or homologs thereof that maintain CD34 activity (e.g. within at least 50%, 80%, 90%, 95%, 96%, 97%, 98%, 99% or 100% activity compared to CD34). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD34 protein. In embodiments, the CD34 protein is substantially identical to the protein identified by the UniProt reference number P28906 or a variant or homolog having substantial identity thereto.

The term "recombinant" when used with reference, e.g., to a cell, nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. Transgenic cells and plants are those that express a heterologous gene or coding sequence, typically as a result of recombinant methods.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The term "exogenous" refers to a molecule or substance (e.g., a compound, nucleic acid or protein) that originates from outside a given cell or organism. For example, an "exogenous promoter" as referred to herein is a promoter that does not originate from the cell or organism it is expressed by. Conversely, the term "endogenous" or "endogenous promoter" refers to a molecule or substance that is native to, or originates within, a given cell or organism.

As defined herein, the term "inhibition", "inhibit", "inhibiting" and the like in reference to cell proliferation (e.g., cancer cell proliferation) means negatively affecting (e.g., decreasing proliferation) or killing the cell. In some embodiments, inhibition refers to reduction of a disease or symptoms of disease (e.g., cancer, cancer cell proliferation). Thus, inhibition includes, at least in part, partially or totally blocking stimulation, decreasing, preventing, or delaying activation, or inactivating, desensitizing, or down-regulating signal transduction or enzymatic activity or the amount of a protein. Similarly an "inhibitor" is a compound or protein that inhibits a receptor or another protein, e.g., by binding, partially or totally blocking, decreasing, preventing, delaying, inactivating, desensitizing, or down-regulating activity (e.g., a receptor activity or a protein activity).

Thus, the terms "inhibitor," "repressor" or "antagonist" or "downregulator" interchangeably refer to a substance capable of detectably decreasing the expression or activity of a given gene or protein (e.g.SMC1). The antagonist can decrease SMC1 expression or activity 10%, 20%, 30%, 40%, 50%, 60%, 70%, 80%, 90% or more in comparison to a control in the absence of the antagonist. In certain instances, SMC1 expression or activity is 1.5-fold, 2-fold, 3-fold, 4-fold, 5-fold, 10-fold or lower than the expression or activity in the absence of the antagonist.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "control" or "standard control" refers to a sample, measurement, or value that serves as a reference, usually a known reference, for comparison to a test sample, measurement, or value. For example, a test sample can be taken from a patient suspected of having a given disease (e.g. cancer) and compared to a known normal (non-diseased) individual (e.g. a standard control subject). A standard control can also represent an average measurement or value gathered from a population of similar individuals (e.g. standard control subjects) that do not have a given disease (i.e. standard control population), e.g., healthy individuals with a similar medical background, same age, weight, etc. A standard control value can also be obtained from the same individual, e.g. from an earlier-obtained sample from the patient prior to disease onset. For example, a control can be devised to compare therapeutic benefit based on pharmacological data (e.g., half-life) or therapeutic measures (e.g., comparison of side effects). Controls are also valuable for determining the significance of data. For example, if values for a given parameter are widely variant in controls, variation in test samples will not be considered as significant. One of skill will recognize that standard controls can be designed for assessment of any number of parameters (e.g. RNA levels, protein levels, specific cell types, specific bodily fluids, specific tissues, synoviocytes, synovial fluid, synovial tissue, fibroblast-like synoviocytes, macrophagelike synoviocytes, etc).

One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

"Patient" or "subject in need thereof" refers to a living organism suffering from or prone to a disease or condition that can be treated by administration of a composition or pharmaceutical composition as provided herein. Non-limiting examples include humans, other mammals, bovines, rats, mice, dogs, monkeys, goat, sheep, cows, deer, and other non-mammalian animals. In some embodiments, a patient is human.

The terms "disease" or "condition" refer to a state of being or health status of a patient or subject capable of being treated with the compounds or methods provided herein. The disease may be a cancer. In some further instances, "cancer" refers to human cancers and carcinomas, sarcomas, adenocarcinomas, lymphomas, leukemias, including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including acute myeloid leukemia (AML), ALL, and CML), or multiple myeloma.

As used herein, the term "cancer" refers to all types of cancer, neoplasm or malignant tumors found in mammals (e.g., humans), including leukemia, carcinomas and sarcomas. Exemplary cancers that may be treated with a compound or method provided herein include breast cancer, colon cancer, kidney cancer, leukemia, lung cancer, melanoma, ovarian cancer, prostate cancer, pancreatic cancer, brain cancer, liver cancer, gastric cancer or a sarcoma.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute myeloid leukemia, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatinifori carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The term "associated" or "associated with" in the context of a substance or substance activity or function associated with a disease (e.g., cancer (e.g. lung cancer, triple negative breast cancer, pancreatic cancer)) means that the disease (e.g., cancer (e.g. lung cancer, triple negative breast cancer, pancreatic cancer)) is caused by (in whole or in part), or a symptom of the disease is caused by (in whole or in part) the substance or substance activity or function. Alternatively, the substance (e.g., SMC1) may be an indicator of the disease (e.g., cancer (e.g. lung cancer, triple negative breast cancer, pancreatic cancer)). Thus, an associated substance may serve as a means of targeting disease tissue (e.g., cancer cells (e.g., lung cancer, triple negative breast cancer, pancreatic cancer)).

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by using a method as described herein), results in reduction of the disease or one or more disease symptoms.

A "therapeutic agent" as referred to herein, is a composition useful in treating or preventing a disease such as cancer (e.g., leukemia). In embodiments, the therapeutic agent is an anti-cancer agent. "Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer.

As used herein, "treating" or "treatment of" a condition, disease or disorder or symptoms associated with a condition, disease (e.g., cancer, e.g., lung cancer, triple negative breast cancer, pancreatic cancer) or disorder refers to an approach for obtaining beneficial or desired results, including clinical results. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean prolonging survival of a subject beyond that expected in the absence of treatment. "Treating" can also mean inhibiting the progression of the condition, disorder or disease, slowing the progression of the condition, disorder or disease temporarily, although in some instances, it involves halting the progression of the condition, disorder or disease permanently. As used herein the terms treatment, treat, or treating refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

The terms "dose" and "dosage" are used interchangeably herein. A dose refers to the amount of active ingredient given to an individual at each administration. The dose will vary depending on a number of factors, including the range of normal doses for a given therapy, frequency of administration; size and tolerance of the individual; severity of the condition; risk of side effects; and the route of administration. One of skill will recognize that the dose can be modified depending on the above factors or based on therapeutic progress. The term "dosage form" refers to the particular format of the pharmaceutical or pharmaceutical composition, and depends on the route of administration. For example, a dosage form can be in a liquid form for nebulization, e.g., for inhalants, in a tablet or liquid, e.g., for oral delivery, or a saline solution, e.g., for injection.

By "therapeutically effective dose or amount" as used herein is meant a dose that produces effects for which it is administered (e.g. treating or preventing a disease). The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)). For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a standard control. A therapeutically effective dose or amount may ameliorate one or more symptoms of a disease. A therapeutically effective dose or amount may prevent or delay the onset of a disease or one or more symptoms of a disease when the effect for which it is being administered is to treat a person who is at risk of developing the disease.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym.* Ed. 7:623-645, 1995; as biodegradable and injectable gel formulations (see, e.g., Gao *Pharm. Res.* 12:857-863, 1995); or, as microspheres for oral administration (see, e.g., Eyles, *J Pharm. Pharmacol.* 49:669-674, 1997). In embodiments, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin.*

*Biotechnol.* 6:698-708, 1995; Ostro, *Am. J. Hosp. Pharm.* 46:1576-1587, 1989). The compositions of the present invention can also be delivered as nanoparticles.

In embodiments, the method further includes administering to the subject an additional therapeutic agent. As described above, a therapeutic agent is a composition useful in treating or preventing a disease such as cancer. In embodiments, the additional therapeutic agent is an anti-cancer agent.

The terms "anti-cancer agent" and "anticancer agent" are used in accordance with their plain ordinary meaning and refer to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras famesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin;

cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rlL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578

(Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin Al (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta *Medica*), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lso-eleutherobin A, and Z-Eleutherobin), Caribaeoside, Caribaeolin, Halichondrin B, D-64131 (Asta *Medica*), D-68144 (Asta *Medica*), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to 111In, 90Y, or 131I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™) afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

As used herein, the term "pharmaceutically acceptable" is used synonymously with "physiologically acceptable" and "pharmacologically acceptable". A pharmaceutical composition will generally comprise agents for buffering and preservation in storage, and can include buffers and carriers for appropriate delivery, depending on the route of administration.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The pharmaceutical preparation is optionally in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The unit dosage form can be of a frozen dispersion.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Antibody Compositions

Provided herein are, inter alia, antibodies capable of binding Structural Maintenance of Chromosome-1 (SMC1). The antibodies provided herein include novel light chain and heavy chain sequences and bind SMC1 (e.g., SMC1A or SMC1B) with high efficiency and specificity. The SMC1 antibodies provided herein including embodiments thereof exhibit improved binding ability compared to known SMC1 antibodies. See for example, FIGS. 19A and 19B. SMC1 proteins are located in the nucleus in healthy cells, where they are required for sister chromatid cohesion, DNA repair and regulation of gene expression. Applicants have surprisingly found that SMC1 proteins are expressed on the cell surface of cancer cells, including for example, triple negative breast cancer (TNBC), prostate cancer, pancreatic cancer, lung cancer and cancer cells with cancer stem-like properties. The SMC1 antibodies provided herein including embodiments thereof are, inter alia, useful for targeting cancer cells expressing SMC1 on their surface. The SMC1 antibodies provided herein including embodiments thereof, may be used for diagnostic and therapeutic purposes, for example, as humanized SMC1 antibodies, antibody drug conjugates or they may form part of bispecific antibodies or chimeric antigen receptors.

In a first aspect is provided a Structural Maintenance of Chromosome-1 (SMC1) antibody including a light chain variable domain and a heavy chain variable domain, wherein the light chain variable domain includes: a CDR L1 as set forth in SEQ ID NO:1, a CDR L2 as set forth in SEQ ID NO:2 and a CDR L3 as set forth in SEQ ID NO:3; and wherein the heavy chain variable domain includes: a CDR H1 as set forth in SEQ ID NO:4, a CDR H2 as set forth in SEQ ID NO:5, and a CDR H3 as set forth in SEQ ID NO:6.

In another aspect is provided a Structural Maintenance of Chromosome-1 (SMC1) antibody including a light chain variable domain and a heavy chain variable domain, wherein the light chain variable domain includes: a CDR L1 as set forth in SEQ ID NO:7, a CDR L2 as set forth in SEQ ID NO:8 and a CDR L3 as set forth in SEQ ID NO:9; and wherein the heavy chain variable domain includes: a CDR H1 as set forth in SEQ ID NO:10, a CDR H2 as set forth in SEQ ID NO:11, and a CDR H3 as set forth in SEQ ID NO:12.

In another aspect is provided a Structural Maintenance of Chromosome-1 (SMC1) antibody including a light chain variable domain and a heavy chain variable domain, wherein the light chain variable domain includes: a CDR L1 as set forth in SEQ ID NO:13, a CDR L2 as set forth in SEQ ID NO:14 and a CDR L3 as set forth in SEQ ID NO: 15; and wherein the heavy chain variable domain includes: a CDR H1 as set forth in SEQ ID NO:16, a CDR H2 as set forth in SEQ ID NO:17, and a CDR H3 as set forth in SEQ ID NO:18.

In another aspect is provided a Structural Maintenance of Chromosome-1 (SMC1) antibody including a light chain variable domain and a heavy chain variable domain, wherein the light chain variable domain includes: a CDR L1 as set forth in SEQ ID NO:19, a CDR L2 as set forth in SEQ ID NO:20 and a CDR L3 as set forth in SEQ ID NO:21; and wherein the heavy chain variable domain includes: a CDR H1 as set forth in SEQ ID NO:22, a CDR H2 as set forth in SEQ ID NO:23, and a CDR H3 as set forth in SEQ ID NO:24; or a CDR H1 as set forth in SEQ ID NO:25, a CDR H2 as set forth in SEQ ID NO:26, and a CDR H3 as set forth in SEQ ID NO:27.

In another aspect is provided a Structural Maintenance of Chromosome-1 (SMC1) antibody binding the same epitope as one of the SMC1 antibodies provided herein including embodiments thereof. In embodiments, the epitope includes the sequence of SEQ ID NO:45, SEQ ID NO:46, SEQ ID NO:47, SEQ ID NO:48, or SEQ ID NO:49. In embodiments, the epitope has the sequence of SEQ ID NO:45, SEQ ID NO:46, SEQ ID NO:47, SEQ ID NO:48, or SEQ ID NO:49. In embodiments, the epitope includes the sequence of SEQ ID NO:45. In embodiments, the epitope has the sequence of SEQ ID NO:45. In embodiments, the epitope includes the sequence of SEQ ID NO:46. In embodiments, the epitope has the sequence of SEQ ID NO:46. In embodiments, the epitope includes the sequence of SEQ ID NO:47. In embodiments, the epitope has the sequence of SEQ ID NO:47. In embodiments, the epitope includes the sequence of SEQ ID NO:48. In embodiments, the epitope has the sequence of SEQ ID NO:48. In embodiments, the epitope includes the sequence of SEQ ID NO:49. In embodiments, the epitope has the sequence of SEQ ID NO:49.

The SMC1 antibodies provided herein may be covalently or non-covalently attached to a peptide compound. The peptide compound provided herein may include a peptidyl moiety also referred to herein as "meditope." Any of the meditopes and meditope-antibody complexes described in WO 2013/055404 or WO 2019/028190, which are incorporated herein in their entirety and for all purposes, may be used for the compositions or methods provided herein. The modified antibodies as described herein, including embodiments thereof, may be referred to herein, for example in the Examples, as meditope-enabled (me) antibodies. In embodiments, the meditope-enabled antibody is a monoclonal antibody (memAb). In embodiments, the meditope-enabled antibody is a humanized antibody. In embodiments, the Fab region of an antibody may be meditope enabled. In embodiments, the meditope-enabled antibody is a Fab. The term "meditope" as used herein refers to a peptidyl moiety included in the peptide compound as described herein. Thus, in embodiments, a meditope is a peptidyl moiety.

Meditope-enabled antibodies allow for the binding (e.g., covalent, non-covalent) of peptidyl moieties to a region in the Fab portion of the antibody without negatively influencing antibody binding site behavior. For example, a meditope bound to a meditope-enabled antibody does not interfere with the binding of the antibody to its antigen. The peptidyl moieties (also referred to herein as meditopes) may be functionalized. For example, the peptidyl moieties may be conjugated to therapeutic or diagnostic agents through a covalent linker (e.g., using, for example, suitable reactive groups and click chemistry). A functionalized peptidyl moiety may be referred to herein as a peptide compound. The ability of the antibody to bind (covalently, non-covalently) a peptide compound endows the meditope-enabled antibody with the functionality to simultaneously target its specific antigen via its antibody binding site and deliver a therapeutic or diagnostic agent.

The antibodies contemplated herein are anti-SMC1 antibodies capable of binding (e.g., covalently, non-covalently) a peptidyl moiety in its Fab region, where the peptidyl moiety may be further conjugated to one or multiple ligands (e.g., a diagnostic or a therapeutic agent/moiety).

Thus, in another aspect is provided a Structural Maintenance of Chromosome-1 (SMC1) antibody including a light chain variable domain and a heavy chain variable domain, wherein the light chain variable domain includes: a CDR L1 as set forth in SEQ ID NO:39, a CDR L2 as set forth in SEQ ID NO:40 and a CDR L3 as set forth in SEQ ID NO:41; and wherein the heavy chain variable domain includes: a CDR H1 as set forth in SEQ ID NO:42, a CDR H2 as set forth in SEQ ID NO:43, and a CDR H3 as set forth in SEQ ID NO:44.

As described above, a "light chain variable (VL) domain" as provided herein forms part of the variable region of the light chain of an antibody, an antibody variant or fragment thereof. Likewise, the "heavy chain variable (VH) domain" as provided herein forms part of the variable region of the heavy chain of an antibody, an antibody variant or fragment thereof. The light chain variable domain and the heavy chain variable domain together form the paratope, which binds an antigen (epitope). The paratope or antigen-binding site is formed at the N-terminus of an antibody, an antibody variant or fragment thereof. In embodiments, the light chain variable (VL) domain includes CDR L1, CDR L2, CDR L3 and FR L1, FR L2, FR L3 and FR L4 (framework regions) of an antibody light chain. In embodiments, the heavy chain variable (VH) domain includes CDR H1, CDR H2, CDR H3 and FR H1, FR H2, FR H3 and FR H4 (framework regions) of an antibody heavy chain. In embodiments, the light chain variable (VL) domain and a light chain constant (CL) domain form part of an antibody light chain. In embodiments, the heavy chain variable (VH) domain and a heavy chain constant (CH1) domain form part of an antibody heavy chain. In embodiments, the heavy chain variable (VH) domain and one or more heavy chain constant (CH1, CH2, or CH3) domains form part of an antibody heavy chain. Thus, in embodiments, the light chain variable (VL) domain forms part of an antibody. In embodiments, the heavy chain variable (VH) domain forms part of an antibody. In embodiments, the light chain variable (VL) domain forms part of a therapeutic antibody. In embodiments, the heavy chain variable (VH) domain forms part of a therapeutic antibody. In embodiments, the light chain variable (VL) domain forms part of a human antibody. In embodiments, the heavy chain variable (VH) domain forms part of a human antibody. In embodiments, the light chain variable (VL) domain forms part of a humanized antibody. In embodiments, the heavy chain variable (VH) domain forms part of a humanized antibody. In embodiments, the light chain variable (VL) domain forms part of a chimeric antibody. In embodiments, the heavy chain variable (VH) domain forms part of a chimeric antibody. In embodiments, the light chain variable (VL) domain forms part of an antibody fragment. In embodiments, the heavy chain variable (VH) domain forms part of an antibody fragment. In embodiments, the light chain variable (VL) domain forms part of an antibody variant. In embodiments, the heavy chain variable (VH) domain forms part of an antibody variant. In embodiments, the light chain variable (VL) domain forms part of a Fab. In embodiments, the heavy chain variable (VH) domain forms part of a Fab. In embodiments, the light chain variable (VL) domain forms part of a scFv. In embodiments, the heavy chain variable (VH) domain forms part of a scFv. In embodiments, the light chain variable (VL) domain forms part of a single domain antibody. In embodiments, the heavy chain variable (VH) domain forms part of a single domain antibody.

In embodiments, the SMC1 antibody is a humanized antibody. In embodiments, the SMC1 antibody is a chimeric antibody. In embodiments, the SMC1 antibody is a Fab' fragment. In embodiments, the SMC1 antibody is a single chain antibody (scFv).

In embodiments, the light chain variable domain includes the sequence of SEQ ID NO:28, SEQ ID NO:30, or SEQ ID NO:32. In embodiments, the light chain variable domain includes the sequence of SEQ ID NO:28. In embodiments, the light chain variable domain includes the sequence of SEQ ID NO:30. In embodiments, the light chain variable domain includes the sequence of SEQ ID NO: 32. In embodiments, the light chain variable domain is the sequence of SEQ ID NO:28. In embodiments, the light chain variable domain is the sequence of SEQ ID NO:30. In embodiments, the light chain variable domain is the sequence of SEQ ID NO:32.

In embodiments, the antibody includes a light chain including the sequence of SEQ ID NO:34. In embodiments, the antibody includes a light chain with the sequence of SEQ ID NO: 34. In embodiments, the antibody includes a light chain including the sequence of SEQ ID NO:37. In embodiments, the antibody includes a light chain with the sequence of SEQ ID NO:37.

In embodiments, the heavy chain variable domain includes the sequence of SEQ ID NO:29, SEQ ID NO:31 or SEQ ID NO:33. In embodiments, the heavy chain variable domain includes the sequence of SEQ ID NO:29. In embodiments, the heavy chain variable domain includes the sequence of SEQ ID NO:31. In embodiments, the heavy chain variable domain includes the sequence of SEQ ID NO:33. In embodiments, the heavy chain variable domain is the sequence of SEQ ID NO:29. In embodiments, the heavy chain variable domain is the sequence of SEQ ID NO:31. In embodiments, the heavy chain variable domain is the sequence of SEQ ID NO:33.

In embodiments, the antibody includes a heavy chain including the sequence of SEQ ID NO:35. In embodiments, the antibody includes a heavy chain with the sequence of SEQ ID NO:35. In embodiments, the antibody includes a heavy chain including the sequence of SEQ ID NO:36. In embodiments, the antibody includes a heavy chain with the sequence of SEQ ID NO:36. In embodiments, the antibody includes a heavy chain including the sequence of SEQ ID NO:38. In embodiments, the antibody includes a heavy chain with the sequence of SEQ ID NO:38.

In embodiments, the antibody is bound to an SMC1 protein. In embodiments, the SMC1 protein is a human SMC1 protein. In embodiments, the SMC1 protein forms part of a cell. In embodiments, the SMC1 protein is expressed on the surface of a cell. In embodiments, the cell is a cancer cell. In embodiments, the cell is a triple negative breast cancer (TNBC) cell, a glioblastoma cell, a prostate cancer cell, a pancreatic cancer cell, a lung cancer cell, a cancer stem cell or a metastatic cancer cell. In embodiments, the cell is a triple negative breast cancer (TNBC) cell. In embodiments, the cell is a glioblastoma cell. In embodiments, the cell is a prostate cancer cell. In embodiments, the cell is a pancreatic cancer cell. In embodiments, the cell is a prostate cancer cell. In embodiments, the cell is a lung cancer cell. In embodiments, the cell is a cancer stem cell. In embodiments, the cell is a metastatic cancer cell.

In embodiments, the antibody is bound to a therapeutic moiety or a diagnostic moiety. In embodiments, the antibody is bound to a therapeutic moiety. In embodiments, the antibody is bound to a diagnostic moiety. In embodiments, the antibody is bound to a meditope. In further embodiments, the meditope is bound (covalently or non-covalently) to a diagnostic moiety or a therapeutic moiety. In further embodiments, the meditope is bound (covalently or non-covalently) to a diagnostic moiety. In further embodiments, the meditope is bound (covalently or non-covalently) to a therapeutic moiety.

In one embodiment, the SMC1 antibody includes a light chain variable domain of SEQ ID NO:28 and a heavy chain variable domain of SEQ ID NO:29.

In one embodiment, the SMC1 antibody includes a light chain variable domain of SEQ ID NO:30 and a heavy chain variable domain of SEQ ID NO:31.

In one embodiment, the SMC1 antibody includes a light chain variable domain of SEQ ID NO:32 and a heavy chain variable domain of SEQ ID NO:33.

In one embodiment, the SMC1 antibody includes a light chain of SEQ ID NO:34 and a heavy chain of SEQ ID NO:35.

In one embodiment, the SMC1 antibody includes a light chain of SEQ ID NO:34 and a heavy chain of SEQ ID NO:36.

In one embodiment, the SMC1 antibody includes a light chain of SEQ ID NO:37 and a heavy chain of SEQ ID NO:37.

Recombinant Protein Compositions

As described above, the light chain variable (VL) domain and the heavy chain variable (VH) domain provided herein including embodiments thereof, may each independently form part of an antibody, an antibody variant, a fragment of an antibody, a fragment of an antibody variant, or a recombinant protein (e.g., a chimeric antigen receptor, bispecific antibody). Provided herein are, inter alia, recombinant proteins (e.g., a chimeric antigen receptor, a bispecific antibody), which include the light chain variable (VL) domain and/or the heavy chain variable (VH) domain as provided herein and are therefore capable of binding SMC1 on cancer cells. In embodiments, the recombinant protein is a chimeric antigen receptor (CAR). In embodiments, the recombinant protein is a bispecific antibody.

Chimeric Antigen Receptor Proteins

Provided herein are, inter alia, recombinant proteins, wherein the recombinant protein is a chimeric antigen receptor. The antibody region of the recombinant protein may include any of the light chain and heavy chain variable domains provided herein including embodiments thereof. The light chain variable (VL) domain and/or the heavy chain variable (VH) domain as provided herein may form part of a chimeric antigen receptor. Thus, in an aspect is provided a recombinant protein including: (i) an antibody region including: (a) a light chain variable domain including a CDR L1 as set forth in SEQ ID NO: 1, a CDR L2 as set forth in SEQ ID NO:2 and a CDR L3 as set forth in SEQ ID NO:3; and (b) a heavy chain variable domain including a CDR H1 as set forth in SEQ ID NO:4, a CDR H2 as set forth in SEQ ID NO:5, and a CDR H3 as set forth in SEQ ID NO:6; and (ii) a transmembrane domain.

In another aspect is provided a recombinant protein including: (i) an antibody region including: (a) a light chain variable domain including a CDR L1 as set forth in SEQ ID NO:7, a CDR L2 as set forth in SEQ ID NO:8 and a CDR L3 as set forth in SEQ ID NO:9; and (b) a heavy chain variable domain including a CDR H1 as set forth in SEQ ID NO: 10, a CDR H2 as set forth in SEQ ID NO:11, and a CDR H3 as set forth in SEQ ID NO:12; and (ii) a transmembrane domain.

In another aspect is provided a recombinant protein including: (i) an antibody region including: (a) a light chain variable domain including a CDR L1 as set forth in SEQ ID NO:13, a CDR L2 as set forth in SEQ ID NO:14 and a CDR L3 as set forth in SEQ ID NO: 15; and (b) a heavy chain variable domain including a CDR H1 as set forth in SEQ ID NO: 16, a CDR H2 as set forth in SEQ ID NO:17, and a CDR H3 as set forth in SEQ ID NO: 18; and (ii) a transmembrane domain.

In another aspect is provided a recombinant protein including: (i) an antibody region including: (a) a light chain variable domain including a CDR L1 as set forth in SEQ ID NO:19, a CDR L2 as set forth in SEQ ID NO:20 and a CDR L3 as set forth in SEQ ID NO:21; and (b) a heavy chain variable domain including a CDR H1 as set forth in SEQ ID NO:22, a CDR H2 as set forth in SEQ ID NO:23, and a CDR H3 as set forth in SEQ ID NO:24; or a CDR H1 as set forth in SEQ ID NO:25, a CDR H2 as set forth in SEQ ID NO:26, and a CDR H3 as set forth in SEQ ID NO:27; and (ii) a transmembrane domain.

In another aspect is provided a recombinant protein including: (i) an antibody region including: (a) a light chain variable domain including a CDR L1 as set forth in SEQ ID NO:39, a CDR L2 as set forth in SEQ ID NO:40 and a CDR L3 as set forth in SEQ ID NO:41; and (b) a heavy chain variable domain including a CDR H1 as set forth in SEQ ID NO:42, a CDR H2 as set forth in SEQ ID NO:43, and a CDR H3 as set forth in SEQ ID NO: 44; and (ii) a transmembrane domain.

An "antibody region" as provided herein refers to a monovalent or multivalent protein moiety that forms part of the recombinant protein (e.g., CAR) provided herein including embodiments thereof. A person of ordinary skill in the art will therefore immediately recognize that the antibody region is a protein moiety capable of binding an antigen (epitope). Thus, the antibody region provided herein may include a domain of an antibody (e.g., a light chain variable (VL) domain, a heavy chain variable (VH) domain) or a fragment of an antibody (e.g., Fab). In embodiments, the antibody region is a protein conjugate. A "protein conjugate" as provided herein refers to a construct consisting of more than one polypeptide, wherein the polypeptides are bound together covalently or non-covalently. In embodiments, the protein conjugate includes a Fab moiety (a monovalent Fab) covalently attached to an scFv moiety (a monovalent scFv). In embodiments, the protein conjugate includes a plurality (at least two) Fab moieties. In embodiments, the polypeptides of a protein conjugate are encoded by one nucleic acid molecule. In embodiments, the polypeptides of a protein conjugate are encoded by different nucleic acid molecules. In embodiments, the polypeptides are connected through a linker. In embodiments, the polypeptides are connected through a chemical linker. In embodiments, the antibody region is an scFv. The antibody region may include a light chain variable (VL) domain and/or a heavy chain variable (VH) domain. Thus, in embodiments, the antibody region includes a single domain antibody. In embodiments, the antibody region includes a light chain variable (VL) domain. In embodiments, the antibody region includes a heavy chain variable (VH) domain. In embodiments, the antibody region is a single domain antibody. In embodiments, the single domain antibody includes a heavy chain variable (VH) domain. In embodiments, the single domain antibody includes a light chain variable (VL) domain. In embodiments, the single domain antibody is a heavy chain variable (VH) domain. In embodiments, the single domain antibody is a light chain variable (VL) domain.

A "transmembrane domain" as provided herein refers to a polypeptide forming part of a biological membrane. The transmembrane domain provided herein is capable of spanning a biological membrane (e.g., a cellular membrane) from one side of the membrane through to the other side of the membrane. In embodiments, the transmembrane domain spans from the intracellular side to the extracellular side of a cellular membrane. Transmembrane domains may include non-polar, hydrophobic residues, which anchor the proteins provided herein including embodiments thereof in a biological membrane (e.g., cellular membrane of a T cell). Any transmembrane domain capable of anchoring the proteins provided herein including embodiments thereof are contemplated. Non-limiting examples of transmembrane domains include the transmembrane domains of CD28, CD8, CD4 or CD3-zeta. In embodiments, the transmembrane domain is a CD4 transmembrane domain.

In embodiments, the transmembrane domain is a CD28 transmembrane domain. The term "CD28 transmembrane domain" as provided herein includes any of the recombinant or naturally-occurring forms of the transmembrane domain of CD28, or variants or homologs thereof that maintain CD28 transmembrane domain activity (e.g. within at least 50%, 80%, 90%, 95%, 96%, 97%, 98%, 99% or 100% activity compared to the CD28 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD28 transmembrane domain polypeptide. In embodiments, CD28 is the protein as identified by the NCBI sequence reference GI:340545506, homolog or functional fragment thereof.

In embodiments, the transmembrane domain is a CD8 transmembrane domain. The term "CD8 transmembrane domain" as provided herein includes any of the recombinant or naturally-occurring forms of the transmembrane domain of CD8, or variants or homologs thereof that maintain CD8 transmembrane domain activity (e.g. within at least 50%, 80%, 90%, 95%, 96%, 97%, 98%, 99% or 100% activity compared to the CD8 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD8 transmembrane domain polypeptide. In embodiments, CD8 is the protein as identified by the NCBI sequence reference GI:225007534, homolog or functional fragment thereof.

In embodiments, the transmembrane domain is a CD4 transmembrane domain. The term "CD4 transmembrane domain" as provided herein includes any of the recombinant or naturally-occurring forms of the transmembrane domain of CD4, or variants or homologs thereof that maintain CD4 transmembrane domain activity (e.g. within at least 50%, 80%, 90%, 95%, 96%, 97%, 98%, 99% or 100% activity compared to the CD4 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD4 transmembrane domain polypeptide. In embodiments, CD4 is the protein as identified by the NCBI sequence reference GI:303522473, homolog or functional fragment thereof.

In embodiments, the transmembrane domain is a CD3-zeta (also known as CD247) transmembrane domain. The term "CD3-zeta transmembrane domain" as provided herein includes any of the recombinant or naturally-occurring forms of the transmembrane domain of CD3-zeta, or variants or homologs thereof that maintain CD3-zeta transmembrane domain activity (e.g. within at least 50%, 80%, 90%, 95%, 96%, 97%, 98%, 99% or 100% activity compared to the CD3-zeta transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD3-zeta transmembrane domain polypeptide. In embodiments, CD3-zeta is the protein as identified by the NCBI sequence reference GI:166362721, homolog or functional fragment thereof.

The recombinant proteins (e.g., chimeric antigen receptors) provided herein may include any of the SMC1 antibodies or fragments thereof described herein. Thus, the recombinant proteins (e.g., chimeric antigen receptors) may include any of the CDRs, heavy chain variable domains, or light chain variable domains provided herein. For example, the heavy chain variable domain may include the sequence of SEQ ID NO:29, SEQ ID NO:31, or SEQ ID NO:33. In embodiments, the heavy chain variable domain is the sequence of SEQ ID NO:29, SEQ ID NO:31, or SEQ ID NO:33. For example, the light chain variable domain may include the sequence of SEQ ID NO:28, SEQ ID NO:30 or SEQ ID NO:32. In embodiments, light chain variable domain is the sequence of SEQ ID NO:28, SEQ ID NO:30 or SEQ ID NO:32.

Thus, the recombinant protein may include a light chain of SEQ ID NO:34 or SEQ ID NO:37. In embodiments, the recombinant protein includes a light chain of SEQ ID NO:34 or SEQ ID NO:37. In embodiments, the recombinant protein includes a heavy chain of SEQ ID NO:35, SEQ ID NO:36 or SEQ ID NO:38.

In embodiments, the antibody region includes an Fc domain. In embodiments, the Fc domain is an IgG4 Fc domain. In embodiments, the antibody region includes an Fc hinge domain. In embodiments, the antibody region includes an IgG4 Fc hinge domain. In embodiments, the antibody region includes a spacer region. In embodiments, the spacer region is between the transmembrane domain and the antibody region. A "spacer region" as provided herein is a polypeptide connecting the antibody region with the transmembrane domain. In embodiments, the spacer region connects the heavy chain constant region with the transmembrane domain. In embodiments, the spacer region includes an Fc region. In embodiments, the spacer region is an Fc region. Examples of spacer regions contemplated for the recombinant protein compositions provided herein include without limitation, immunoglobulin molecules or fragments thereof (e.g., IgG1, IgG2, IgG3, IgG4) and immunoglobulin molecules or fragments thereof (e.g., IgG1, IgG2, IgG3, IgG4) including mutations affecting Fc receptor binding. In embodiments, the spacer region is a hinge region. In embodiments, the spacer region is an IgG4 hinge region. In embodiments, the spacer region is a modified IgG4 hinge region.

In embodiments, the recombinant protein as provided herein, including embodiments thereof, further includes an intracellular co-stimulatory signaling domain. An "intracellular co-stimulatory signaling domain" as provided herein includes amino acid sequences capable of providing co-stimulatory signaling in response to binding of an antigen to the antibody region provided herein including embodiments thereof. In embodiments, the signaling of the co-stimulatory signaling domain results in production of cytokines and proliferation of the T cell expressing the same. In embodiments, the intracellular co-stimulatory signaling domain is a CD28 intracellular co-stimulatory signaling domain, a 4-1BB intracellular co-stimulatory signaling domain, a ICOS intracellular co-stimulatory signaling domain, or an OX-40 intracellular co-stimulatory signaling domain. In embodiments, the intracellular co-stimulatory signaling domain is a CD28 intracellular co-stimulatory signaling domain. In embodiments, the intracellular co-stimulatory signaling domain is a 4-1BB intracellular co-stimulatory signaling domain. In embodiments, the intracellular co-stimulatory signaling domain is a ICOS intracellular co-stimulatory signaling domain. In embodiments, the intracellular co-stimulatory signaling domain is an OX-40 intracellular co-stimulatory signaling domain.

In embodiments, the recombinant protein as provided herein including embodiments thereof, further includes an intracellular T-cell signaling domain. An "intracellular T-cell signaling domain" as provided herein includes amino acid sequences capable of providing primary signaling in response to binding of an antigen to the antibody region provided herein including embodiments thereof. In embodiments, the signaling of the intracellular T-cell signaling domain results in activation of the T cell expressing the same. In embodiments, the signaling of the intracellular T-cell signaling domain results in proliferation (cell division) of the T cell expressing the same. In embodiments, the signaling of the intracellular T-cell signaling domain results in expression of proteins known in the art to be characteristic of activated T cell (e.g., CTLA-4, PD-1, CD28, CD69). In embodiments, the intracellular T-cell signaling domain includes the signaling domain of the zeta chain of the human CD3 complex. In embodiments, the intracellular T-cell signaling domain is a CD3 ζ (intracellular T-cell signaling domain.

The term "CTLA-4" as referred to herein includes any of the recombinant or naturally-occurring forms of the cytotoxic T-lymphocyte-associated protein 4 protein, also known as CD152 (cluster of differentiation 152), or variants or homologs thereof that maintain CTLA-4 activity (e.g. within at least 50%, 80%, 90%, 95%, 96%, 97%, 98%, 99% or 100% activity compared to CTLA-4). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CTLA-4 protein. In embodiments, the CTLA-4 protein is substantially identical to the protein identified by the UniProt reference number P16410 or a variant or homolog having substantial identity thereto.

The term "PD-1" as referred to herein includes any of the recombinant or naturally-occurring forms of the Programmed cell death protein 1 protein, also known as CD279 (cluster of differentiation 279), or variants or homologs thereof that maintain PD-1 activity (e.g. within at least 50%, 80%, 90%, 95%, 96%, 97%, 98%, 99% or 100% activity compared to PD-1). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PD-1 protein. In embodiments, the PD-1 protein is substantially identical to the protein identified by the UniProt reference number Q15116 or a variant or homolog having substantial identity thereto.

The term "CD28" as referred to herein includes any of the recombinant or naturally-occurring forms of the Cluster of Differentiation 28 protein, or variants or homologs thereof that maintain CD28 activity (e.g. within at least 50%, 80%, 90%, 95%, 96%, 97%, 98%, 99% or 100% activity compared to CD28). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD28 protein. In embodiments, the CD28 protein is substantially identical to the protein identified by the UniProt reference number P10747 or a variant or homolog having substantial identity thereto.

The term "CD69" as referred to herein includes any of the recombinant or naturally-occurring forms of the Cluster of Differentiation 69 protein, or variants or homologs thereof that maintain CD69 activity (e.g. within at least 50%, 80%, 90%, 95%, 96%, 97%, 98%, 99% or 100% activity compared to CD69). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD69 protein. In embodiments, the CD69 protein is substantially identical to the protein identified by the UniProt reference number Q07108 or a variant or homolog having substantial identity thereto.

The term "4-1BB" as referred to herein includes any of the recombinant or naturally-occurring forms of the 4-1BB protein, also known as tumor necrosis factor receptor superfamily member 9 (TNFRSF9), Cluster of Differentiation 137 (CD137) and induced by lymphocyte activation (ILA), or variants or homologs thereof that maintain 4-1BB activity (e.g. within at least 50%, 80%, 90%, 95%, 96%, 97%, 98%, 99% or 100% activity compared to 4-1BB). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring EGFR protein. In embodiments, the 4-1BB protein is substantially identical to the protein identified by the UniProt reference number Q07011 or a variant or homolog having substantial identity thereto.

In embodiments, the recombinant protein as provided herein including embodiments thereof, further includes a self-cleaving peptidyl sequence. In embodiments, the self-cleaving peptidyl linker sequence is a T2A sequence or a 2A sequence. In embodiments, the self-cleaving peptidyl linker sequence is a T2A sequence. In embodiments, the self-cleaving peptidyl linker sequence is a 2A sequence.

Bispecific Antibodies

The recombinant proteins provided herein may, inter alia, be chimeric antigen receptors. Thus, the second antibody region may include any of the light chain and/or heavy chain variable domains provided herein including embodiments thereof. The light chain variable (VL) domain and/or the heavy chain variable (VH) domain as provided herein may form part of a bispecific antibody. Thus, in another aspect is provided a recombinant protein including: (i) a first antibody region capable of binding an effector cell ligand; and (ii) a second antibody region, including: (a) a second light chain variable domain including a CDR L1 as set forth in SEQ ID NO:1, a CDR L2 as set forth in SEQ ID NO:2 and a CDR L3 as set forth in SEQ ID NO:3; a CDR L1 as set forth in SEQ ID NO:7, a CDR L2 as set forth in SEQ ID NO:8 and a CDR L3 as set forth in SEQ ID NO:9; a CDR L1 as set forth in SEQ ID NO: 13, a CDR L2 as set forth in SEQ ID NO:14 and a CDR L3 as set forth in SEQ ID NO:15; or a CDR L1 as set forth in SEQ ID NO:19, a CDR L2 as set forth in SEQ ID NO:20 and a CDR L3 as set forth in SEQ ID NO:21; and (b) a second heavy chain variable domain including a CDR H1 as set forth in SEQ ID NO:4, a CDR H2 as set forth in SEQ ID NO:5, and a CDR H3 as set forth in SEQ ID NO:6; a CDR H1 as set forth in SEQ ID NO:10, a CDR H2 as set forth in SEQ ID NO: 11, and a CDR H3 as set forth in SEQ ID NO: 12; a CDR H1 as set forth in SEQ ID NO:16, a CDR H2 as set forth in SEQ ID NO:17, and a CDR H3 as set forth in SEQ ID NO: 18; a CDR H1 as set forth in SEQ ID NO:22, a CDR H2 as set forth in SEQ ID NO:23, and a CDR H3 as set forth in SEQ ID NO:24; or a CDR H1 as set forth in SEQ ID NO:25, a CDR H2 as set forth in SEQ ID NO:26, and a CDR H3 as set forth in SEQ ID NO:27.

In embodiments, the second light chain variable domain includes: a CDR L1 as set forth in SEQ ID NO:1, a CDR L2 as set forth in SEQ ID NO:2 and a CDR L3 as set forth in SEQ ID NO:3; and the second heavy chain variable domain includes: a CDR H1 as set forth in SEQ ID NO:4, a CDR H2 as set forth in SEQ ID NO:5, and a CDR H3 as set forth in SEQ ID NO:6.

In embodiments, the second light chain variable domain includes: a CDR L1 as set forth in SEQ ID NO:7, a CDR L2 as set forth in SEQ ID NO:8 and a CDR L3 as set forth in SEQ ID NO:9; and the second heavy chain variable domain includes: a CDR H1 as set forth in SEQ ID NO: 10, a CDR H2 as set forth in SEQ ID NO:11, and a CDR H3 as set forth in SEQ ID NO: 12.

In embodiments, the second light chain variable domain includes: a CDR L1 as set forth in SEQ ID NO: 13, a CDR L2 as set forth in SEQ ID NO:14 and a CDR L3 as set forth in SEQ ID NO:15; and the second heavy chain variable domain includes: a CDR H1 as set forth in SEQ ID NO: 16, a CDR H2 as set forth in SEQ ID NO:17, and a CDR H3 as set forth in SEQ ID NO: 18.

In embodiments, the second light chain variable domain includes: a CDR L1 as set forth in SEQ ID NO: 19, a CDR L2 as set forth in SEQ ID NO:20 and a CDR L3 as set forth in SEQ ID NO:21; and the second heavy chain variable domain includes: a CDR H1 as set forth in SEQ ID NO:22, a CDR H2 as set forth in SEQ ID NO:23, and a CDR H3 as set forth in SEQ ID NO:24; or a CDR H1 as set forth in SEQ ID NO:25, a CDR H2 as set forth in SEQ ID NO:26, and a CDR H3 as set forth in SEQ ID NO:27.

In embodiments, the second light chain variable domain includes: a CDR L1 as set forth in SEQ ID NO:19, a CDR L2 as set forth in SEQ ID NO:20 and a CDR L3 as set forth in SEQ ID NO:21; and the second heavy chain variable domain includes: a CDR H1 as set forth in SEQ ID NO:22, a CDR H2 as set forth in SEQ ID NO:23, and a CDR H3 as set forth in SEQ ID NO: 24.

In embodiments, the second light chain variable domain includes: a CDR L1 as set forth in SEQ ID NO: 19, a CDR L2 as set forth in SEQ ID NO:20 and a CDR L3 as set forth in SEQ ID NO:21; and the second heavy chain variable domain includes: a CDR H1 as set forth in SEQ ID NO:25, a CDR H2 as set forth in SEQ ID NO:26, and a CDR H3 as set forth in SEQ ID NO:27.

In embodiments, the second light chain variable domain includes: a CDR L1 as set forth in SEQ ID NO: 39, a CDR L2 as set forth in SEQ ID NO:40 and a CDR L3 as set forth in SEQ ID NO:41; and the second heavy chain variable domain includes: a CDR H1 as set forth in SEQ ID NO:42, a CDR H2 as set forth in SEQ ID NO:43, and a CDR H3 as set forth in SEQ ID NO: 44.

The term "effector cell ligand" as provided herein refers to a cell surface molecule expressed on an effector cell of the immune system (e.g., a cytotoxic T cell, a helper T cell, a B cell, a natural killer cell). Upon binding of the first antibody region to the effector cell ligand expressed on the effector cell, the effector cell is activated and able to exert its function (e.g., selective killing or eradication of malignant, infected or otherwise unhealthy cells). In embodiments, the effector cell ligand is a CD3 protein. In embodiments, the effector cell ligand is a CD16 protein. In embodiments, the effector cell ligand is a CD32 protein. In embodiments, the effector cell ligand is a NKp46 protein. The first antibody region as provided herein may be an antibody, an antibody variant, a fragment of an antibody or a fragment of an antibody variant.

A "CD3 protein" as referred to herein includes any of the recombinant or naturally-occurring forms of the Cluster of Differentiation 3 (CD3) proteins or variants or homologs thereof that comprise the CD3 complex that mediates signal transduction and maintains CD3 complex activity (e.g. within at least 50%, 80%, 90%, 95%, 96%, 97%, 98%, 99% or 100% activity compared to the CD3 complex). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD3 proteins in the CD3 complex.

A "CD16 protein" as referred to herein includes any of the recombinant or naturally-occurring forms of the Cluster of Differentiation 16 (CD16) protein, also known as low affinity immunoglobulin gamma Fc region receptor III-A, or variants or homologs thereof that maintain CD16 activity (e.g. within at least 50%, 80%, 90%, 95%, 96%, 97%, 98%, 99% or 100% activity compared to CD16). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD16 protein. In embodiments, the CD16 protein is substantially identical to the protein identified by the UniProt reference number P08637 or a variant or homolog having substantial identity thereto.

A "CD32 protein" as referred to herein includes any of the recombinant or naturally-occurring forms of the Cluster of Differentiation 32 (CD32) protein, also known as low affinity immunoglobulin gamma Fc region receptor II-A, or variants or homologs thereof that maintain CD32 activity (e.g. within at least 50%, 80%, 90%, 95%, 96%, 97%, 98%, 99% or 100% activity compared to CD32). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD32 protein. In embodiments, the CD32 protein is substantially identical to the protein identified by the UniProt reference number P12318 or a variant or homolog having substantial identity thereto.

A "NKp46 protein" as referred to herein includes any of the recombinant or naturally-occurring forms of the NKp46 protein, also known as natural cytotoxicity triggering receptor 1, or variants or homologs thereof that maintain NKp46 activity (e.g. within at least 50%, 80%, 90%, 95%, 96%, 97%, 98%, 99% or 100% activity compared to NKp46). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring NKp46 protein. In embodiments, the NKp46 protein is substantially identical to the protein identified by the UniProt reference number 076036 or a variant or homolog having substantial identity thereto.

In embodiments, the effector cell ligand as disclosed herein is a CD3 protein.

In embodiments, the second light chain variable domain includes the sequence of SEQ ID NO:28, SEQ ID NO:30, or SEQ ID NO:32. In embodiments, the second antibody region includes a light chain having the sequence of SEQ ID NO:34. In embodiments, the second antibody region includes a light chain having the sequence of SEQ ID NO:37.

In embodiments, the second light chain variable domain includes the sequence of SEQ ID NO:29, SEQ ID NO:31, or SEQ ID NO:33. In embodiments, the second antibody region includes a heavy chain having the sequence of SEQ ID NO:35. In embodiments, the second antibody region includes a heavy chain having the sequence of SEQ ID NO:36. In embodiments, the second antibody region includes a heavy chain having the sequence of SEQ ID NO:38.

In embodiments, the first antibody region is a first Fab' fragment or the second antibody region is a second Fab' fragment. In embodiments, the first antibody region is a first Fab' fragment and the second antibody region is a second Fab' fragment.

In embodiments, the first antibody region is a single chain variable fragment (scFv) or the second antibody region is a second single chain variable fragment (scFv). In embodiments, the first antibody region is a single chain variable fragment (scFv) and the second antibody region is a second single chain variable fragment (scFv). In embodiments, the first antibody region is a single chain variable fragment (scFv). In embodiments, the second antibody region is a second single chain variable fragment (scFv).

Pharmaceutical Compositions

The antibodies and recombinant proteins provided herein including embodiments thereof may form part of a pharmaceutical compositions. Thus, in another aspect is provided a pharmaceutical composition including (i) a therapeutically effective amount of a SMC1 antibody as provided herein including embodiments thereof, or a therapeutically effective amount of a recombinant protein as provided herein including embodiments thereof and (ii) a pharmaceutically acceptable excipient.

Methods of Treatment

The compositions (e.g., the anti SMC1 antibodies and recombinant proteins) provided herein, including embodiments thereof, are contemplated as providing effective treatments for diseases such as cancer (e.g., triple negative breast cancer, lung cancer, pancreatic cancer). Thus, in an aspect is provided a method of treating cancer in a subject in need thereof, the method including administering to a subject a therapeutically effective amount of a SMC1 antibody as provided herein including embodiments thereof or a therapeutically effective amount of a recombinant protein as provided herein including embodiments thereof, thereby treating cancer in the subject.

In an aspect is provided a method of treating cancer in a subject in need thereof, the method including administering to a subject a therapeutically effective amount of a SMC1 antibody as provided herein including embodiments thereof. In embodiments, the antibody is attached to a therapeutic moiety. In embodiments, the antibody forms part of an ADC (antibody-drug conjugate).

In an aspect is provided a method of treating cancer in a subject in need thereof, the method including administering to a subject a therapeutically effective amount of a recombinant protein as provided herein including embodiments thereof, thereby treating cancer in the subject.

In embodiments, the cancer is a drug resistant cancer. In embodiments, the cancer is triple negative breast cancer (TNBC), glioblastoma, prostate cancer, pancreatic cancer, lung cancer, or metastatic cancer. In embodiments, the cancer is triple negative breast cancer (TNBC). In embodiments, the cancer is glioblastoma. In embodiments, the cancer is prostate cancer. In embodiments, the cancer is pancreatic cancer. In embodiments, the cancer is prostate cancer. In embodiments, the cancer is metastatic cancer.

The compositions provided herein, including embodiments thereof, are contemplated as diagnostic tools for monitoring treatment of cancer and detecting cells related to cancer in vivo and in vitro. Thus, in another aspect is provided a method of detecting a cancer cell the method including contacting a cancer cell with a SMC1 antibody as provided herein including embodiments thereof, thereby forming an antibody-cell conjugate and detecting the antibody-cell conjugate. In embodiments, the antibody-cell conjugate as disclosed herein is in a detection device.

Nucleic Acid Compositions

The compositions provided herein include nucleic acid molecules encoding the anti-SMC1 antibodies and recombinant proteins provided herein including embodiments thereof.

Thus, in an aspect is provided an isolated nucleic acid encoding a SMC1 antibody as provided herein including embodiments thereof.

In another aspect a cell including a SMC1 antibody as provided herein including embodiments thereof.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Structural Maintenance of Chromosome-1A (SMC1A), a component of the multi-protein complex named cohesin (SMC1A, SMC3, RAD21, SCC1) is normally found only in the nucleus, where it is required for sister chromatid cohesion, DNA repair and regulation of gene expression. However, we have found that SMC1A was located on the cell surface of many cancer cells, including triple negative breast cancer (TNBC), prostate, pancreatic and lung and cancer cells with cancer stem-like properties. Our data showed that SMC1A, a nuclear protein was present at cell membrane, cytoplasm and cytoskeleton (shown by Immuno-cytochemical studies along with flow cytometry and cell fractionation) in cancer cells while predominantly nuclear expression in normal cells. These findings were confirmed in a panel of cancer tissues of breast, prostate, and lung using the SMC1A antibodies. SMC1A showed distinct membranous and cytoplasmic localization in significant number of tumor tissues whereas predominantly nuclear localization in normal tissue sections. In the stem-cell like population sorted from breast cancer cells, SMC1A showed predominantly membranous and cytoplasmic localization. Our data showed the role of SMC1A in tumor proliferation and metastasis suggesting that the amplified product of this gene may play a role in carcinogenesis.

Although tremendous progress has been made in the field of cancer immunotherapy for both hematological and solid tumors, lack of cancer-specific cell surface markers in aggressive cancers has resulted in a death of targeted therapies and poor patient outcomes. We have developed proprietary anti-SMC1 antibodies (such as SMC1A4) which recognize SMC1A antigen on the surface of tumor cells of various histology, including breast, prostate, glioblastoma and lung cancer. Tumor cells, especially those with P53 mutations, showed strong cell surface binding whereas normal cells show only nuclear localization. SMC1A was aberrantly phosphorylated in cancer cells and its phosphorylation was shown to promote cell proliferation and migration. We developed agents targeting SMC1A including the antibodies and peptides. Utilizing SMC1A4 antibody, we will develop targeted immunotherapy agents, including antibody drug conjugates (ADCs) and bispecific antibodies (BsAbs).

TABLE 1

| Details of primary/secondary antibodies | | |
|---|---|---|
| Antibodies | Source | Identifier |
| Rabbit anti-SMC1 (IF: 1:500) | Bethyl Labs | Cat # A300-055A |
| Rabbit anti-SMC1 (IHC: 1:500) | | |
| Rabbit anti-SMC1 (WB: 1:2000) | Abcam | Cat # ab109238 |
| Rabbit anti-Vimentin (WB: 1:1000) | Cell Signaling | Cat # 5741 |
| Rabbit anti-E-cadherin (WB: 1:1000) | Cell Signaling | Cat # 3195 |
| Rabbit anti-N-cadherin (WB: 1:1000) | Cell Signaling | Cat # 13116 |
| Rabbit anti-Snail (WB: 1:1000) | Cell Signaling | Cat # 3879 |
| Rabbit anti-BRCA1 (WB: 1:500) | Cell Signaling | Cat # 14823 |
| Rabbit anti-BRCA2 (WB: 1:1000) | Cell Signaling | Cat # 10741 |
| Rabbit anti-OCT4 (WB: 1:500) | Cell Signaling | Cat # 2750 |
| Rabbit anti-RAD51 (WB: 1:1000) | Cell Signaling | Cat # 8875 |
| Rabbit anti-RAD51 (ICC: 1:500) | Santa Cruz Biotech. | Cat # sc-53428 |
| Rabbit anti-KU80 (WB: 1:1000) | Cell Signaling | Cat # 2753 |
| Rabbit anti-KU70 (WB: 1:1000) | Cell Signaling | Cat # 4588 |
| Rabbit anti-GAPDH (WB: 1:2000) | Cell Signaling | Cat # 5174 |
| Rabbit anti-ALDH1 (WB: 1:500) | Cell Signaling | Cat # 65583 |
| Rabbit yH2AX (phospho-Ser139) (ICC: 1:1000) | Cell Signaling | Cat # 9718 |
| Mouse anti-Claudin (WB: 1:200) | Santa Cruz Biotech. | Cat # sc-81796 |
| Mouse anti-CD44 (WB: 1:1000) | Novus Bio. | Cat # NBP1-47386 |
| Mouse anti-CD44 (Flow: 1:500) | BD Pharmingen | Cat # 347943 |
| Mouse AR/NR3C4 (WB: 1:500) | Novus Bio. | Cat # NBP1-47471 |
| Goat anti-Rabbit-HRP (WB: 1:10000) | Thermo Scientific | Cat # 31460 |

TABLE 1-continued

| | | |
|---|---|---|
| Details of primary/secondary antibodies | | |
| Antibodies | Source | Identifier |
| Rabbit anti-mouse-HRP (WB: 1:10000) (IHC: 1:500) | Thermo Scientific | Cat # 31452 |
| Goat anti-Rabbit-Dylight-550 conjugated (IF: 1:500) | Bethyl Labs | Cat # A50-309D3 |

Sequence of SMC1 antigen peptides used for generating antibodies provided herein including embodiments thereof:

SMC1-ALPHA4 (SMC1A4): EVKPTDEKLRELK-GAKL (SEQ ID NO:45)

SMC1A-ALPHA1 (SMC1A1): DKLKEKKERL-TEELKEQM (SEQ ID NO:46)

SMC1A(IGHV5): AAATDEKLRELKGAKAA (SEQ ID NO:47)

SMC1A(IGHV1-15): AAKKRLEFENQKTRAA (SEQ ID NO:48)

SMC1-BETA: EKVAKDCIRFLKEER (SEQ ID NO:49)

Informal Sequence Listing:

```
                                   SEQ ID NO: 1
SMC1A4 CDR L1 RSSQSIVHSNGNTYLE

SEQ ID NO: 2
SMC1A4 CDR L2 KVSNRFS

SEQ ID NO: 3
SMC1A4 CDR L3 FQGPLYT

SEQ ID NO: 4
SMC1A4 CDR H1 GFNIKDPYMH

SEQ ID NO: 5
SMC1A4 CDR H2 WITPANGNTKYDPKFQA

SEQ ID NO: 6
SMC1A4 CDR H3 SGDAYYWAWFAY

SEQ ID NO: 7
SMC1A1 CDR L1 SASSGLTYMY

SEQ ID NO: 8
SMC1A1 CDR L2 DTSNLAS

SEQ ID NO: 9
SMC1A1 CDR L3 QQWKSFPPT

SEQ ID NO: 10
SMC1A1 CDR H1 GFSLSTSGMGVG

SEQ ID NO: 11
SMC1A1 CDR H2 HIWWDDDQYSNTALRS

SEQ ID NO: 12
SMC1A1 CDR H3 VTTDAVDY

SEQ ID NO: 13
SMC1-Beta CDR L1 SASSSIGYMH

SEQ ID NO: 14
SMC1-Beta CDR L2 DRSKLAS

SEQ ID NO: 15
SMC1-Beta CDR L3 HQRSRYPYT

SEQ ID NO: 16
SMC1-Beta CDR H1KASGYTFTDFNIE

SEQ ID NO: 17
SMC1-Beta CDR H2DINPSNGETIYNKKFKG
```

```
                   -continued
                                   SEQ ID NO: 18
SMC1-Beta CDR H3DHYYGYDYDAMDY SEQ ID NO: 19
SMC1A(IGHV5) and SMC1A(IGHV1-15) CDR L1
QSLLDSDGKTY SEQ ID NO: 20
SMC1A(IGHV5) and SMC1A(IGHV1-15) CDR L2
LVS SEQ ID NO: 21
SMC1A(IGHV5) and SMC1A(IGHV1-15) CDR L3
WQGTHFPQT

SEQ ID NO: 22
SMC1A(IGHV5) CDR H1
GFTFSSYE

SEQ ID NO: 23
SMC1A(IGHV5) CDR H2
ISRGGSYT

SEQ ID NO: 24
SMC1A(IGHV5) CDR H3
VRHELSYALDY

SEQ ID NO: 25
SMC1A(IGHV1-15) CDR H1
GFNIKDYY

SEQ ID NO: 26
SMC1A(IGHV1-15) CDR H2
IDPETGGT

SEQ ID NO: 27
SMC1A(IGHV1-15) CDR H3
TRSDYSYALND

SEQ ID NO: 28
SMC1A4 variable LC
DVLMTQTPLSLTVSLGDQASISCRSSQSIVHSNGNTYLEWYLQKPGQSP

KLLIYKVSNRFSGVSDRFSGSGSGTDFTLKISRVEAEDLGVYYCFQGPL

YTFGGGTKLEIKR

SEQ ID NO: 29
SMC1A4 variable HC
VQLQQSGAELVKPGASVKLSCTASGFNIKDPYMHWVKQRPEQGLEWIGW

ITPANGNTKYDPKFQAKATITADTYSNTAYLQFSSLTSEDTAVYFCARS

GDAYYWAWFAYWGQGTLVTVSA

SEQ ID NO: 30
SMC1A1 variable LC
RGQIVLTQSPAIMSISPGERVTMTCSASSGLTYMYWYQQKPGSSPRLLI

YDTSNLASGVPVRFSGSGSGTSYSLTISRMEAEDAATYYCQQWKSFPPT

FGGGTKLEIKR
```

-continued

SEQ ID NO: 31
SMC1A1 variable HC
VTLKESGPGILQPSQTLSLTCSFSGFSLSTSGMGVGWIRQPSGKGLEWL

AHIWWDDDQYSNTALRSGLTISKDTSKNQVFLKIASVDTSDTATYYCAR

VTTDAVDYWGQGTSVTVSS

SEQ ID NO: 32
SMC1-Beta variable LC
QIVLTQSPAIMSASPGEKVTMTCSASSSIGYMHWYQQKPGTSPKRWIYD

RSKLASGVPARFSGSGSGTSFSLTISSMEAEDAATYYCHQRSRYPYTFG

GGTKLEIKR

SEQ ID NO: 33
SMC1-Beta variable HC
EVKLQESGPELVKSGASVKIPCKASGYTFTDFNIEWVKQNRGKSLEWIG

DINPSNGETIYNKKFKGKATLTVDKSSTTAFMELRSLTSEDTAVYYCAR

DHYYGYDYDAMDYWGQGTSVTVSS

SEQ ID NO: 34
SMC1A(IGHV5) and SMC1A(IGHV1-15) LC
DVVMTQTPLTLSVTIGQPASISCKSSQSLLDSDGKTYLNWLLQRPGQSP

KRLIYLVSKLDSGVPDRFTGSGSGTDFTLKISRVEAEDLGVYYCWQGTH

FPQTFGGGTKLEIKRADAAPTVSIFPPSSEQLTSGGASVVCFLNNFYPK

DINVKWKIDGSERQNGVLNSWTDQDSKDSTYSMSSTLTLTKDEYERHNS

YTCEATHKTSTSPIVKSFNRNEC

SEQ ID NO: 35
SMC1A(IGHV5) HC
AVQLVESGGGLVKPGGSLKLSCAASGFTFSSYETDWVRQTPEKRLEWVA

TISRGGSYTYYPDSVKGRFTISRDNAKNTLYLQMSSLRSEDTAMYYCVR

HELSYALDYWGQGTSVTVSSAKTTAPSVYPLAPVCGDTTGSSVTLGCLV

KGYFPEPVTLTWNSGSLSSGVHTFPAVLQSDLYTLSSSVTVPSSTWPSQ

SITCNVAHPASSTKVDKKIEPRGPTIKPCPPCKCPAPNLLGGPSVFIFP

PKIKDVLMISLSPIVTCVVVDVSEDDPDVQISWFVNNVEVHTAQTQTHR

EDYNSTLRVVSALPIQHQDWMSGKEFKCKVNNKDLPAPIERTISKPKGS

VRAPQVYVLPPPEEEMTKKQVTLTCMVTDFMPEDIYVEWTNNGKTELNY

KNTEPVLDSDGSYFMYSKLRVEKKNWVERNSYSCSVVHEGLHNHHTTKS

FSRTPGK

SEQ ID NO: 36
SMC1A(IGHV1-15) HC
EVQLQQSGAELVRPGASVKLSCTASGFNIKDYYMHWVKQTVPHGLEWIG

AIDPETGGTAYNQKFKGKATLTADKSSSTAYMELRSLTSEDSAVYYCTR

SDYSYALNDWGQGTLVTVSSAKTTAPSVYPLAPVCGDTTGSSVTLGCLV

KGYFPEPVTLTWNSGSLSSGVHTFPAVLQSDLYTLSSSVTVTSSTWPSQ

SITCNVAHPASSTKVDKKIEPRGPTIKPCPPCKCPAPNLLGGPSVFIFP

PKIKDVLMISLSPIVTCVVVDVSEDDPDVQISWFVNNVEVHTAQTQTHR

EDYNSTLRVVSALPIQHQDWMSGKEFKCKVNNKDLPAPIERTISKPKGS

VRAPQVYVLPPPEEEMTKKQVTLTCMVTDFMPEDIYVEWTNNGKTELNY

KNTEPVLDSDGSYFMYSKLRVEKKNWVERNSYSCSVVHEGLHNHHTTKS

FSRTPGK

-continued

SEQ ID NO: 37
meditope-enabled SMC1A4 LC:
DVQMTQSPILLSASVGDRVTITCRSSQSIVHSNGNTYLEWYQQRTNGSP

RLLIYKVSNRFSGVPSRFSGSGSGTDFTLTISSLQPEDIADYYCFQGPL

YTFGAGTKVEIKRTVAAPSVFIFPPSDEQLKSGTASVVCLLNNFYPREA

KVQWKVDNALQSGNSQESVTEQDSKDSTYSLSSTLTLSKADYEKHKVYA

CEVTHQGLSSPVTKSFNRGEC

SEQ ID NO: 38
meditope-enabled SMC1A4 HC:
EVQLVESGGGLVQPGGSLRLSCAASGFNIKDPYMHWVRQSPGKGLEWIG

WITPANGNTKYADSVKGRATISADTSKNTAYLQMNSLRAEDTAIYFCAR

SGDAYYWAWFAYWGQGTLVTVSSASTKGPSVFPLAPSSKSTSGGTAALG

CLVKDYFPEPVTVSWNSGALTSGVHTFPCVLQSSGLYSLSSVVTVPSSS

LGTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYT

QKSLSLSPGK

SEQ ID NO: 39
meditope-enabled SMC1A4 CDR L1
RSSQSIVHSNGNTYLE

SEQ ID NO: 40
meditope-enabled SMC1A4 CDR L2
KVSNRFS

SEQ ID NO: 41
meditope-enabled SMC1A4 CDR L3
FQGPLYT

SEQ ID NO: 42
meditope-enabled SMC1A4 CDR H1
GFNIKDPYMH

SEQ ID NO: 43
meditope-enabled SMC1A4 CDR H2
WITPANGNTKYADSVKGA

SEQ ID NO: 44
meditope-enabled SMC1A4 CDR H3
SGDAYYWAWFAY

Embodiments

Embodiment 1. A Structural Maintenance of Chromosome-1 (SMC1) antibody comprising a light chain variable domain and a heavy chain variable domain, wherein said light chain variable domain comprises: a CDR L1 as set forth in SEQ ID NO:1, a CDR L2 as set forth in SEQ ID NO:2 and a CDR L3 as set forth in SEQ ID NO:3; and wherein said heavy chain variable domain comprises: a CDR H1 as set forth in SEQ ID NO:4, a CDR H2 as set forth in SEQ ID NO:5, and a CDR H3 as set forth in SEQ ID NO:6.

Embodiment 2. A Structural Maintenance of Chromosome-1 (SMC1) antibody comprising a light chain variable domain and a heavy chain variable domain, wherein said light chain variable domain comprises: a CDR L1 as set forth in SEQ ID NO:7, a CDR L2 as set forth in SEQ ID NO:8 and a CDR L3 as set forth in SEQ ID NO:9; and

US 12,617,845 B2

57 wherein said heavy chain variable domain comprises: a CDR H1 as set forth in SEQ ID NO:10, a CDR H2 as set forth in SEQ ID NO:11, and a CDR H3 as set forth in SEQ ID NO:12.

Embodiment 3. A Structural Maintenance of Chromosome-1 (SMC1) antibody comprising a light chain variable domain and a heavy chain variable domain, wherein said light chain variable domain comprises: a CDR L1 as set forth in SEQ ID NO:13, a CDR L2 as set forth in SEQ ID NO:14 and a CDR L3 as set forth in SEQ ID NO: 15; and wherein said heavy chain variable domain comprises: a CDR H1 as set forth in SEQ ID NO:16, a CDR H2 as set forth in SEQ ID NO:17, and a CDR H3 as set forth in SEQ ID NO:18.

Embodiment 4. A Structural Maintenance of Chromosome-1 (SMC1) antibody comprising a light chain variable domain and a heavy chain variable domain, wherein said light chain variable domain comprises: a CDR L1 as set forth in SEQ ID NO:19, a CDR L2 as set forth in SEQ ID NO:20 and a CDR L3 as set forth in SEQ ID NO:21; and wherein said heavy chain variable domain comprises: a CDR H1 as set forth in SEQ ID NO:22, a CDR H2 as set forth in SEQ ID NO:23, and a CDR H3 as set forth in SEQ ID NO:24; or a CDR H1 as set forth in SEQ ID NO:25, a CDR H2 as set forth in SEQ ID NO:26, and a CDR H3 as set forth in SEQ ID NO:27.

Embodiment 5. The SMC1 antibody of any one of embodiments 1-4, wherein said antibody is a humanized antibody.

Embodiment 6. The SMC1 antibody of any one of embodiments 1-4, wherein said antibody is a chimeric antibody.

Embodiment 7. The SMC1 antibody of any one of embodiments 1-6, wherein said antibody is a Fab' fragment.

Embodiment 8. The SMC1 antibody of any one of embodiments 1-5, wherein said antibody is a single chain antibody (scFv).

Embodiment 9. The SMC1 antibody of any one of embodiments 1-8, wherein said light chain variable domain comprises the sequence of SEQ ID NO:28, SEQ ID NO:30, or SEQ ID NO:32.

Embodiment 10. The SMC1 antibody of any one of embodiments 1-9, wherein said heavy chain variable domain comprises the sequence of SEQ ID NO:29, SEQ ID NO:31, or SEQ ID NO:33.

Embodiment 11. The SMC1 antibody of any one of embodiments 1-10, wherein said antibody is bound to an SMC1 protein.

Embodiment 12. The SMC1 antibody of embodiment 11, wherein said SMC1 protein is a human SMC1 protein.

Embodiment 13. The SMC1 antibody of embodiment 11 or 12, wherein said SMC1 protein forms part of a cell.

Embodiment 14. The SMC1 antibody of embodiment 13, wherein said SMC1 protein is expressed on the surface of said cell.

Embodiment 15. The SMC1 antibody of embodiment 13 or 14, wherein said cell is a cancer cell.

Embodiment 16. The SMC1 antibody of any one of embodiments 13-15, wherein said cell is a triple negative breast cancer (TNBC) cell, a glioblastoma cell, a prostate cancer cell, a pancreatic cancer cell, a lung cancer cell, a cancer stem cell or a metastatic cancer cell.

Embodiment 17. The SMC1 antibody of any one of embodiments 1-16, wherein said antibody is bound to a therapeutic moiety or a diagnostic moiety.

58

Embodiment 18. A recombinant protein comprising:
(i) a first antibody region capable of binding an effector cell ligand; and
(ii) a second antibody region, comprising:
(a) a second light chain variable domain comprising a CDR L1 as set forth in SEQ ID NO:1, a CDR L2 as set forth in SEQ ID NO:2 and a CDR L3 as set forth in SEQ ID NO:3; a CDR L1 as set forth in SEQ ID NO:7, a CDR L2 as set forth in SEQ ID NO:8 and a CDR L3 as set forth in SEQ ID NO:9; a CDR L1 as set forth in SEQ ID NO:13, a CDR L2 as set forth in SEQ ID NO:14 and a CDR L3 as set forth in SEQ ID NO:15; or a CDR L1 as set forth in SEQ ID NO:19, a CDR L2 as set forth in SEQ ID NO:20 and a CDR L3 as set forth in SEQ ID NO:21;
and
(b) a second heavy chain variable domain comprising a CDR H1 as set forth in SEQ ID NO:4, a CDR H2 as set forth in SEQ ID NO:5, and a CDR H3 as set forth in SEQ ID NO:6; a CDR H1 as set forth in SEQ ID NO:10, a CDR H2 as set forth in SEQ ID NO:11, and a CDR H3 as set forth in SEQ ID NO: 12; a CDR H1 as set forth in SEQ ID NO:16, a CDR H2 as set forth in SEQ ID NO:17, and a CDR H3 as set forth in SEQ ID NO: 18; a CDR H1 as set forth in SEQ ID NO:22, a CDR H2 as set forth in SEQ ID NO:23, and a CDR H3 as set forth in SEQ ID NO:24; or a CDR H1 as set forth in SEQ ID NO:25, a CDR H2 as set forth in SEQ ID NO:26, and a CDR H3 as set forth in SEQ ID NO:27.

Embodiment 19. The recombinant protein of embodiment 18, wherein said second light chain variable domain comprises:
a CDR L1 as set forth in SEQ ID NO: 1, a CDR L2 as set forth in SEQ ID NO:2 and a CDR L3 as set forth in SEQ ID NO:3; and
wherein said second heavy chain variable domain comprises:
a CDR H1 as set forth in SEQ ID NO:4, a CDR H2 as set forth in SEQ ID NO:5, and a CDR H3 as set forth in SEQ ID NO:6.

Embodiment 20. The recombinant protein of embodiment 18, wherein said second light chain variable domain comprises:
a CDR L1 as set forth in SEQ ID NO: 7, a CDR L2 as set forth in SEQ ID NO:8 and a CDR L3 as set forth in SEQ ID NO:9; and
wherein said second heavy chain variable domain comprises:
a CDR H1 as set forth in SEQ ID NO: 10, a CDR H2 as set forth in SEQ ID NO:11, and a CDR H3 as set forth in SEQ ID NO:12.

Embodiment 21. The recombinant protein of embodiment 18, wherein said second light chain variable domain comprises:
a CDR L1 as set forth in SEQ ID NO: 13, a CDR L2 as set forth in SEQ ID NO:14 and a CDR L3 as set forth in SEQ ID NO:15; and
wherein said second heavy chain variable domain comprises:
a CDR H1 as set forth in SEQ ID NO: 16, a CDR H2 as set forth in SEQ ID NO: 17, and a CDR H3 as set forth in SEQ ID NO:18.

Embodiment 22. The recombinant protein of embodiment 18, wherein said second light chain variable domain comprises:

a CDR L1 as set forth in SEQ ID NO: 19, a CDR L2 as set forth in SEQ ID NO:20 and a CDR L3 as set forth in SEQ ID NO:21; and wherein said second heavy chain variable domain comprises:

a CDR H1 as set forth in SEQ ID NO:22, a CDR H2 as set forth in SEQ ID NO:23, and a CDR H3 as set forth in SEQ ID NO:24; or a CDR H1 as set forth in SEQ ID NO:25, a CDR H2 as set forth in SEQ ID NO:26, and a CDR H3 as set forth in SEQ ID NO:27.

Embodiment 23. The recombinant protein of any one of embodiments 18-22, wherein said effector cell ligand is a CD3 protein.

Embodiment 24. The recombinant protein of any one of embodiments 18-23, wherein said second light chain variable domain comprises the sequence of SEQ ID NO:28, SEQ ID NO:30 or SEQ ID NO:32.

Embodiment 25. The recombinant protein of any one of embodiments 18-24, wherein said second heavy chain variable domain comprises the sequence of SEQ ID NO:29, SEQ ID NO:31 or SEQ ID NO:33.

Embodiment 26. The recombinant protein of any one of embodiments 18-25, wherein said first antibody region is a first Fab' fragment or said second antibody region is a second Fab' fragment.

Embodiment 27. The recombinant protein of any one of embodiments 18-25, wherein said first antibody region is a single chain variable fragment (scFv) or said second antibody region is a second single chain variable fragment (scFv).

Embodiment 28. A pharmaceutical composition comprising (i) a therapeutically effective amount of a SMC1 antibody of any one of embodiments 1-17, or a therapeutically effective amount of a recombinant protein of any one of embodiments 18-27 and (ii) a pharmaceutically acceptable excipient.

Embodiment 29. A method of treating cancer in a subject in need thereof, said method comprising administering to a subject a therapeutically effective amount of a SMC1 antibody of any one of embodiments 1-17 or a therapeutically effective amount of a recombinant protein of any one of embodiments 18-27, thereby treating cancer in said subject.

Embodiment 30. The method of embodiment 29, wherein said cancer is a drug resistant cancer.

Embodiment 31. An isolated nucleic acid encoding a SMC1 antibody of any one of embodiments 1-17.

Embodiment 32. A cell comprising a SMC1 antibody of any one of embodiments 1-17.

Embodiment 33. A method of detecting a cancer cell said method comprising contacting a cancer cell with a SMC1 antibody of any one of embodiments 1-17, thereby forming an antibody-cell conjugate and detecting said antibody-cell conjugate.

Embodiment 34. The method of embodiment 33, wherein said antibody-cell conjugate is in a detection device.

---

What is claimed is:

1. A Structural Maintenance of Chromosome-1 (SMC1) antibody comprising a light chain variable domain and a heavy chain variable domain, wherein said light chain variable domain comprises:

a CDR L1 as set forth in SEQ ID NO:1, a CDR L2 as set forth in SEQ ID NO:2 and a CDR L3 as set forth in SEQ ID NO:3; and wherein said heavy chain variable domain comprises:

a CDR H1 as set forth in SEQ ID NO:4, a CDR H2 as set forth in SEQ ID NO:5, and a CDR H3 as set forth in SEQ ID NO:6.

2. A Structural Maintenance of Chromosome-1 (SMC1) antibody comprising a light chain variable domain and a heavy chain variable domain, wherein said light chain variable domain comprises:

a CDR L1 as set forth in SEQ ID NO:7, a CDR L2 as set forth in SEQ ID NO:8 and a CDR L3 as set forth in SEQ ID NO:9; and wherein said heavy chain variable domain comprises:

a CDR H1 as set forth in SEQ ID NO:10, a CDR H2 as set forth in SEQ ID NO:11, and a CDR H3 as set forth in SEQ ID NO: 12.

3. A Structural Maintenance of Chromosome-1 (SMC1) antibody comprising a light chain variable domain and a heavy chain variable domain, wherein said light chain variable domain comprises:

a CDR L1 as set forth in SEQ ID NO:13, a CDR L2 as set forth in SEQ ID NO:14 and a CDR L3 as set forth in SEQ ID NO:15; and wherein said heavy chain variable domain comprises:

a CDR H1 as set forth in SEQ ID NO:16, a CDR H2 as set forth in SEQ ID NO:17, and a CDR H3 as set forth in SEQ ID NO: 18.

4. A Structural Maintenance of Chromosome-1 (SMC1) antibody comprising a light chain variable domain and a heavy chain variable domain, wherein said light chain variable domain comprises:

a CDR L1 as set forth in SEQ ID NO:19, a CDR L2 as set forth in SEQ ID NO:20 and a CDR L3 as set forth in SEQ ID NO:21; and wherein said heavy chain variable domain comprises:

a CDR H1 as set forth in SEQ ID NO:22, a CDR H2 as set forth in SEQ ID NO:23, and a CDR H3 as set forth in SEQ ID NO:24; or a CDR H1 as set forth in SEQ ID NO:25, a CDR H2 as set forth in SEQ ID NO:26, and a CDR H3 as set forth in SEQ ID NO:27.

5. The SMC1 antibody of any one of claims 1-4, wherein said light chain variable domain comprises the sequence of SEQ ID NO:28, SEQ ID NO:30, or SEQ ID NO:32.

6. The SMC1 antibody of any one of claims 1-4, wherein said heavy chain variable domain comprises the sequence of SEQ ID NO:29, SEQ ID NO:31, or SEQ ID NO:33.

7. A recombinant protein comprising:

(i) a first antibody region capable of binding an effector cell ligand; and (ii) a second antibody region, comprising:

(a) a second light chain variable domain comprising a CDR L1 as set forth in SEQ ID NO:1, a CDR L2 as set forth in SEQ ID NO:2 and a CDR L3 as set forth in SEQ ID NO:3; a CDR L1 as set forth in SEQ ID NO:7, a CDR L2 as set forth in SEQ ID NO:8 and a CDR L3 as set forth in SEQ ID NO:9; a CDR L1 as set forth in SEQ ID NO:13, a CDR L2 as set forth in SEQ ID NO:14 and a CDR L3 as set forth in SEQ ID NO:15; or a CDR L1 as set forth in SEQ ID NO:19, a CDR L2 as set forth in SEQ ID NO:20 and a CDR L3 as set forth in SEQ ID NO:21; and (b) a second heavy chain variable domain comprising a CDR H1 as set forth in SEQ ID NO:4, a CDR H2 as set forth in SEQ ID NO:5, and a CDR H3 as set forth in SEQ ID NO:6; a CDR H1 as set forth in SEQ ID NO:10, a CDR H2 as set forth in SEQ ID NO:11, and a CDR H3 as set forth in SEQ ID NO:12; a CDR H1 as set forth in SEQ ID NO:16, a CDR H2 as set forth in SEQ ID NO:17, and a CDR H3 as set forth in SEQ ID NO:18; a CDR H1 as set forth in SEQ ID NO:22, a CDR H2 as set forth in SEQ ID NO:23, and a CDR H3 as set forth in SEQ ID NO:24; or a CDR H1 as set forth in SEQ ID NO:25, a CDR H2 as set forth in SEQ ID NO:26, and a CDR H3 as set forth in SEQ ID NO:27.

8. The recombinant protein of claim 7, wherein said second light chain variable domain comprises the sequence of SEQ ID NO:28, SEQ ID NO:30 or SEQ ID NO:32.

9. The recombinant protein of claim 7, wherein said second heavy chain variable domain comprises the sequence of SEQ ID NO:29, SEQ ID NO:31 or SEQ ID NO:33.

10. A method of detecting a cancer cell said method comprising contacting a cancer cell with a SMC1 antibody of any one of claims 1-4, thereby forming an antibody-cell conjugate and detecting said antibody-cell conjugate.

\*　\*　\*　\*　\*

SEQUENCE LISTING

```
<160> NUMBER OF SEQ ID NOS: 44

<210> SEQ ID NO 1
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 1

Arg Ser Ser Gln Ser Ile Val His Ser Asn Gly Asn Thr Tyr Leu Glu
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 2

Lys Val Ser Asn Arg Phe Ser
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 3

Phe Gln Gly Pro Leu Tyr Thr
1               5

<210> SEQ ID NO 4
```

-continued

```
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 4

Gly Phe Asn Ile Lys Asp Pro Tyr Met His
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 5

Trp Ile Thr Pro Ala Asn Gly Asn Thr Lys Tyr Asp Pro Lys Phe Gln
1               5                   10                  15

Ala

<210> SEQ ID NO 6
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 6

Ser Gly Asp Ala Tyr Tyr Trp Ala Trp Phe Ala Tyr
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 7

Ser Ala Ser Ser Gly Leu Thr Tyr Met Tyr
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 8

Asp Thr Ser Asn Leu Ala Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 9

Gln Gln Trp Lys Ser Phe Pro Pro Thr
1               5
```

-continued

```
<210> SEQ ID NO 10
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 10

Gly Phe Ser Leu Ser Thr Ser Gly Met Gly Val Gly
1               5                   10

<210> SEQ ID NO 11
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 11

His Ile Trp Trp Asp Asp Asp Gln Tyr Ser Asn Thr Ala Leu Arg Ser
1               5                   10                  15

<210> SEQ ID NO 12
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 12

Val Thr Thr Asp Ala Val Asp Tyr
1               5

<210> SEQ ID NO 13
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 13

Ser Ala Ser Ser Ser Ile Gly Tyr Met His
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 14

Asp Arg Ser Lys Leu Ala Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 15

His Gln Arg Ser Arg Tyr Pro Tyr Thr
1               5

<210> SEQ ID NO 16
```

```
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 16

Lys Ala Ser Gly Tyr Thr Phe Thr Asp Phe Asn Ile Glu
1               5                   10

<210> SEQ ID NO 17
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 17

Asp Ile Asn Pro Ser Asn Gly Glu Thr Ile Tyr Asn Lys Lys Phe Lys
1               5                   10                  15

Gly

<210> SEQ ID NO 18
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 18

Asp His Tyr Tyr Gly Tyr Asp Tyr Asp Ala Met Asp Tyr
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 19

Gln Ser Leu Leu Asp Ser Asp Gly Lys Thr Tyr
1               5                   10

<210> SEQ ID NO 20
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 20

Leu Val Ser
1

<210> SEQ ID NO 21
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 21

Trp Gln Gly Thr His Phe Pro Gln Thr
1               5
```

```
<210> SEQ ID NO 22
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 22

Gly Phe Thr Phe Ser Ser Tyr Glu
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 23

Ile Ser Arg Gly Gly Ser Tyr Thr
1               5

<210> SEQ ID NO 24
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 24

Val Arg His Glu Leu Ser Tyr Ala Leu Asp Tyr
1               5                   10

<210> SEQ ID NO 25
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 25

Gly Phe Asn Ile Lys Asp Tyr Tyr
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 26

Ile Asp Pro Glu Thr Gly Gly Thr
1               5

<210> SEQ ID NO 27
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 27

Thr Arg Ser Asp Tyr Ser Tyr Ala Leu Asn Asp
1               5                   10

<210> SEQ ID NO 28
```

<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 28

Asp Val Leu Met Thr Gln Thr Pro Leu Ser Leu Thr Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Ser
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Pro Leu Tyr Thr Phe Gly Gly Gly Thr Lys Leu Glu Ile Lys Arg
            100                 105                 110

<210> SEQ ID NO 29
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 29

Val Gln Leu Gln Gln Ser Gly Ala Glu Leu Val Lys Pro Gly Ala Ser
1               5                   10                  15

Val Lys Leu Ser Cys Thr Ala Ser Gly Phe Asn Ile Lys Asp Pro Tyr
            20                  25                  30

Met His Trp Val Lys Gln Arg Pro Glu Gln Gly Leu Glu Trp Ile Gly
        35                  40                  45

Trp Ile Thr Pro Ala Asn Gly Asn Thr Lys Tyr Asp Pro Lys Phe Gln
    50                  55                  60

Ala Lys Ala Thr Ile Thr Ala Asp Thr Tyr Ser Asn Thr Ala Tyr Leu
65                  70                  75                  80

Gln Phe Ser Ser Leu Thr Ser Glu Asp Thr Ala Val Tyr Phe Cys Ala
                85                  90                  95

Arg Ser Gly Asp Ala Tyr Tyr Trp Ala Trp Phe Ala Tyr Trp Gly Gln
            100                 105                 110

Gly Thr Leu Val Thr Val Ser Ala
        115                 120

<210> SEQ ID NO 30
<211> LENGTH: 109
<212> TYPE: PRT
<213> ORGANISM: Artificial Sequence
<220> FEATURE:
<223> OTHER INFORMATION: Synthetic polypeptide

<400> SEQUENCE: 30

Arg Gly Gln Ile Val Leu Thr Gln Ser Pro Ala Ile Met Ser Ile Ser
1               5                   10                  15

Pro Gly Glu Arg Val Thr Met Thr Cys Ser Ala Ser Ser Gly Leu Thr
            20                  25                  30

```
Tyr Met Tyr Trp Tyr Gln Gln Lys Pro Gly Ser Ser Pro Arg Leu Leu
        35                  40                  45

Ile Tyr Asp Thr Ser Asn Leu Ala Ser Gly Val Pro Val Arg Phe Ser
    50                  55                  60

Gly Ser Gly Ser Gly Thr Ser Tyr Ser Leu Thr Ile Ser Arg Met Glu
65                  70                  75                  80

Ala Glu Asp Ala Ala Thr Tyr Tyr Cys Gln Gln Trp Lys Ser Phe Pro
                85                  90                  95

Pro Thr Phe Gly Gly Gly Thr Lys Leu Glu Ile Lys Arg
            100                 105

<210> SEQ ID NO 31
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 31

Val Thr Leu Lys Glu Ser Gly Pro Gly Ile Leu Gln Pro Ser Gln Thr
1               5                   10                  15

Leu Ser Leu Thr Cys Ser Phe Ser Gly Phe Ser Leu Ser Thr Ser Gly
            20                  25                  30

Met Gly Val Gly Trp Ile Arg Gln Pro Ser Gly Lys Gly Leu Glu Trp
        35                  40                  45

Leu Ala His Ile Trp Trp Asp Asp Asp Gln Tyr Ser Asn Thr Ala Leu
    50                  55                  60

Arg Ser Gly Leu Thr Ile Ser Lys Asp Thr Ser Lys Asn Gln Val Phe
65                  70                  75                  80

Leu Lys Ile Ala Ser Val Asp Thr Ser Asp Thr Ala Thr Tyr Tyr Cys
                85                  90                  95

Ala Arg Val Thr Thr Asp Ala Val Asp Tyr Trp Gly Gln Gly Thr Ser
            100                 105                 110

Val Thr Val Ser Ser
        115

<210> SEQ ID NO 32
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 32

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Ile Gly Tyr Met
            20                  25                  30

His Trp Tyr Gln Gln Lys Pro Gly Thr Ser Pro Lys Arg Trp Ile Tyr
        35                  40                  45

Asp Arg Ser Lys Leu Ala Ser Gly Val Pro Ala Arg Phe Ser Gly Ser
    50                  55                  60

Gly Ser Gly Thr Ser Phe Ser Leu Thr Ile Ser Ser Met Glu Ala Glu
65                  70                  75                  80

Asp Ala Ala Thr Tyr Tyr Cys His Gln Arg Ser Arg Tyr Pro Tyr Thr
                85                  90                  95

Phe Gly Gly Gly Thr Lys Leu Glu Ile Lys Arg
            100                 105
```

```
<210> SEQ ID NO 33
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 33

Glu Val Lys Leu Gln Glu Ser Gly Pro Glu Leu Val Lys Ser Gly Ala
1               5                   10                  15

Ser Val Lys Ile Pro Cys Lys Ala Ser Gly Tyr Thr Phe Thr Asp Phe
            20                  25                  30

Asn Ile Glu Trp Val Lys Gln Asn Arg Gly Lys Ser Leu Glu Trp Ile
        35                  40                  45

Gly Asp Ile Asn Pro Ser Asn Gly Glu Thr Ile Tyr Asn Lys Lys Phe
    50                  55                  60

Lys Gly Lys Ala Thr Leu Thr Val Asp Lys Ser Ser Thr Thr Ala Phe
65                  70                  75                  80

Met Glu Leu Arg Ser Leu Thr Ser Glu Asp Thr Ala Val Tyr Tyr Cys
                85                  90                  95

Ala Arg Asp His Tyr Tyr Gly Tyr Asp Tyr Asp Ala Met Asp Tyr Trp
            100                 105                 110

Gly Gln Gly Thr Ser Val Thr Val Ser Ser
        115                 120

<210> SEQ ID NO 34
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 34

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
            165                 170                 175

Thr Tyr Ser Met Ser Ser Thr Leu Thr Leu Thr Lys Asp Glu Tyr Glu
```

-continued

```
                180                 185                 190
Arg His Asn Ser Tyr Thr Cys Glu Ala Thr His Lys Thr Ser Thr Ser
        195                 200                 205

Pro Ile Val Lys Ser Phe Asn Arg Asn Glu Cys
        210                 215

<210> SEQ ID NO 35
<211> LENGTH: 448
<212> TYPE: PRT
<213> ORGANISM: Artificial Sequence
<220> FEATURE:
<223> OTHER INFORMATION: Synthetic polypeptide

<400> SEQUENCE: 35

Ala Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Glu Thr Asp Trp Val Arg Gln Thr Pro Glu Lys Arg Leu Glu Trp Val
        35                  40                  45

Ala Thr Ile Ser Arg Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Val Arg His Glu Leu Ser Tyr Ala Leu Asp Tyr Trp Gly Gln Gly Thr
            100                 105                 110

Ser Val Thr Val Ser Ser Ala Lys Thr Thr Ala Pro Ser Val Tyr Pro
            115                 120                 125

Leu Ala Pro Val Cys Gly Asp Thr Thr Gly Ser Ser Val Thr Leu Gly
    130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Gln Ser Ile Thr Cys Asn Val Ala His Pro Ala Ser Ser
            195                 200                 205

Thr Lys Val Asp Lys Lys Ile Glu Pro Arg Gly Pro Thr Ile Lys Pro
        210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Val Asp Val Ser Glu Asp Asp Pro
            260                 265                 270

Asp Val Gln Ile Ser Trp Phe Val Asn Asn Val Glu Val His Thr Ala
            275                 280                 285

Gln Thr Gln Thr His Arg Glu Asp Tyr Asn Ser Thr Leu Arg Val Val
        290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
```

-continued

```
                325                 330                 335
Ile Ser Lys Pro Lys Gly Ser Val Arg Ala Pro Gln Val Tyr Val Leu
            340                 345                 350

Pro Pro Pro Glu Glu Glu Met Thr Lys Lys Gln Val Thr Leu Thr Cys
            355                 360                 365

Met Val Thr Asp Phe Met Pro Glu Asp Ile Tyr Val Glu Trp Thr Asn
        370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
            420                 425                 430

Leu His Asn His His Thr Thr Lys Ser Phe Ser Arg Thr Pro Gly Lys
            435                 440                 445

<210> SEQ ID NO 36
<211> LENGTH: 448
<212> TYPE: PRT
<213> ORGANISM: Artificial Sequence
<220> FEATURE:
<223> OTHER INFORMATION: Synthetic polypeptide

<400> SEQUENCE: 36

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Thr Val Pro His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Ser Asp Tyr Ser Tyr Ala Leu Asn Asp Trp Gly Gln Gly Thr
            100                 105                 110

Leu Val Thr Val Ser Ser Ala Lys Thr Thr Ala Pro Ser Val Tyr Pro
        115                 120                 125

Leu Ala Pro Val Cys Gly Asp Thr Thr Gly Ser Ser Val Thr Leu Gly
    130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
    210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
```

-continued

```
                    245                 250                 255
Ser Pro Ile Val Thr Cys Val Val Val Asp Val Ser Glu Asp Asp Pro
            260                 265                 270

Asp Val Gln Ile Ser Trp Phe Val Asn Asn Val Glu Val His Thr Ala
            275                 280                 285

Gln Thr Gln Thr His Arg Glu Asp Tyr Asn Ser Thr Leu Arg Val Val
            290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
                340                 345                 350

Pro Pro Pro Glu Glu Glu Met Thr Lys Lys Gln Val Thr Leu Thr Cys
                355                 360                 365

Met Val Thr Asp Phe Met Pro Glu Asp Ile Tyr Val Glu Trp Thr Asn
            370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
            420                 425                 430

Leu His Asn His His Thr Thr Lys Ser Phe Ser Arg Thr Pro Gly Lys
            435                 440                 445

<210> SEQ ID NO 37
<211> LENGTH: 217
<212> TYPE: PRT
<213> ORGANISM: Artificial Sequence
<220> FEATURE:
<223> OTHER INFORMATION: Synthetic polypeptide

<400> SEQUENCE: 37

Asp Val Gln Met Thr Gln Ser Pro Ile Leu Leu Ser Ala Ser Val Gly
1               5                   10                  15

Asp Arg Val Thr Ile Thr Cys Arg Ser Ser Gln Ser Ile Val His Ser
                20                  25                  30

Asn Gly Asn Thr Tyr Leu Glu Trp Tyr Gln Gln Arg Thr Asn Gly Ser
            35                  40                  45

Pro Arg Leu Leu Ile Tyr Lys Val Ser Asn Arg Phe Ser Gly Val Pro
        50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Ile Ala Asp Tyr Tyr Cys Phe Gln Gly
                85                  90                  95

Pro Leu Tyr Thr Phe Gly Ala Gly Thr Lys Val Glu Ile Lys Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
```

```
                    165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 38
<211> LENGTH: 451
<212> TYPE: PRT
<213> ORGANISM: Artificial Sequence
<220> FEATURE:
<223> OTHER INFORMATION: Synthetic polypeptide

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Pro
            20                  25                  30

Tyr Met His Trp Val Arg Gln Ser Pro Gly Lys Gly Leu Glu Trp Ile
        35                  40                  45

Gly Trp Ile Thr Pro Ala Asn Gly Asn Thr Lys Tyr Ala Asp Ser Val
    50                  55                  60

Lys Gly Arg Ala Thr Ile Ser Ala Asp Thr Ser Lys Asn Thr Ala Tyr
65                  70                  75                  80

Leu Gln Met Asn Ser Leu Arg Ala Glu Asp Thr Ala Ile Tyr Phe Cys
                85                  90                  95

Ala Arg Ser Gly Asp Ala Tyr Tyr Trp Ala Trp Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Cys
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
```

-continued

```
305               310               315               320

Lys Glu Tyr Lys Cys Lys Val Ser Asn Lys Ala Leu Pro Ala Pro Ile
                325               330               335

Glu Lys Thr Ile Ser Lys Ala Lys Gly Gln Pro Arg Glu Pro Gln Val
                340               345               350

Tyr Thr Leu Pro Pro Ser Arg Asp Glu Leu Thr Lys Asn Gln Val Ser
                355               360               365

Leu Thr Cys Leu Val Lys Gly Phe Tyr Pro Ser Asp Ile Ala Val Glu
                370               375               380

Trp Glu Ser Asn Gly Gln Pro Glu Asn Asn Tyr Lys Thr Thr Pro Pro
385               390               395               400

Val Leu Asp Ser Asp Gly Ser Phe Phe Leu Tyr Ser Lys Leu Thr Val
                405               410               415

Asp Lys Ser Arg Trp Gln Gln Gly Asn Val Phe Ser Cys Ser Val Met
                420               425               430

His Glu Ala Leu His Asn His Tyr Thr Gln Lys Ser Leu Ser Leu Ser
                435               440               445

Pro Gly Lys
    450

<210> SEQ ID NO 39
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 39

Arg Ser Ser Gln Ser Ile Val His Ser Asn Gly Asn Thr Tyr Leu Glu
1               5               10              15

<210> SEQ ID NO 40
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 40

Lys Val Ser Asn Arg Phe Ser
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 41

Phe Gln Gly Pro Leu Tyr Thr
1               5

<210> SEQ ID NO 42
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 42

Gly Phe Asn Ile Lys Asp Pro Tyr Met His
```

```
1               5                   10

<210> SEQ ID NO 43
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 43

Trp Ile Thr Pro Ala Asn Gly Asn Thr Lys Tyr Ala Asp Ser Val Lys
1               5                   10                  15

Gly Ala

<210> SEQ ID NO 44
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 44

Ser Gly Asp Ala Tyr Tyr Trp Ala Trp Phe Ala Tyr
1               5                   10
```